United States Patent
Ben Rubi

(10) Patent No.: US 9,050,078 B2
(45) Date of Patent: Jun. 9, 2015

(54) IMPLANTED MEDICAL DEVICE USEFUL FOR COSMETIC SURGERY

(75) Inventor: Yaniv Ben Rubi, Shimshit (IL)

(73) Assignee: AESTHETICS POINT LTD., Sderot (IL)

( * ) Notice: Subject to any disclaimer, the term of this patent is extended or adjusted under 35 U.S.C. 154(b) by 403 days.

(21) Appl. No.: 13/379,360

(22) PCT Filed: Jun. 21, 2010

(86) PCT No.: PCT/IL2010/000485
§ 371 (c)(1),
(2), (4) Date: Feb. 6, 2012

(87) PCT Pub. No.: WO2010/150244
PCT Pub. Date: Dec. 29, 2010

(65) Prior Publication Data
US 2012/0172931 A1    Jul. 5, 2012

Related U.S. Application Data

(60) Provisional application No. 61/218,958, filed on Jun. 21, 2009.

(51) Int. Cl.
*A61B 17/08* (2006.01)
*A61B 17/04* (2006.01)

(52) U.S. Cl.
CPC ..... *A61B 17/0401* (2013.01); *A61B 2017/0409* (2013.01); *A61B 2017/0412* (2013.01); *A61B 2017/0414* (2013.01); *A61B 2017/0417* (2013.01); *A61B 2017/042* (2013.01); *A61B 2017/0464* (2013.01)

(58) Field of Classification Search
USPC ......... 606/151, 157, 158, 213, 215–218, 228, 606/232
See application file for complete search history.

(56) References Cited

U.S. PATENT DOCUMENTS

| | | | |
|---|---|---|---|
| 5,147,373 A | | 9/1992 | Ferzli |
| 5,269,809 A | * | 12/1993 | Hayhurst et al. ............ 606/232 |
| 5,511,564 A | | 4/1996 | Wilk |
| 5,520,691 A | * | 5/1996 | Branch ......................... 606/301 |

(Continued)

FOREIGN PATENT DOCUMENTS

WO    WO2006065837 A2    6/2006

OTHER PUBLICATIONS

International Search Report in Corresponding International Application No. PCT/IL2010/000485 dated Oct. 25, 2010.

*Primary Examiner* — Ryan Severson
(74) *Attorney, Agent, or Firm* — Paul D. Bianco; Martin Fleit; Fleit Gibbons Gutman Bongini & Bianco PL

(57) ABSTRACT

The present invention discloses a minimally invasive multi-point fixation device adapted to laparoscopically locally reposition body tissues. The device comprises: a distal anchor, a proximal anchor and an elongated connecting element, adapted to interconnect between the distal anchor and the proximal anchor. The distal and the proximal anchors are characterized by two configurations: (i) a FOLDED CONFIGURATION; and, (ii) a DEPLOYED CONFIGURATION. The fixation device further comprises deployment means adapted to deploy the distal and the proximal anchors by reconfiguring the same from the FOLDED CONFIGURATION to the DEPLOYED CONFIGURATION.

28 Claims, 44 Drawing Sheets

(56) References Cited

U.S. PATENT DOCUMENTS

| | | | |
|---|---|---|---|
| 5,928,267 A * | 7/1999 | Bonutti et al. | 606/216 |
| 5,984,933 A * | 11/1999 | Yoon | 606/148 |
| 6,368,326 B1 * | 4/2002 | Dakin et al. | 606/103 |
| 6,436,088 B2 * | 8/2002 | Frazier et al. | 604/508 |
| 6,464,713 B2 | 10/2002 | Bonutti | 606/232 |
| 6,503,267 B2 * | 1/2003 | Bonutti et al. | 606/232 |
| 6,582,453 B1 * | 6/2003 | Tran et al. | 606/232 |
| 6,699,263 B2 * | 3/2004 | Cope | 606/232 |
| 6,702,835 B2 * | 3/2004 | Ginn | 606/215 |
| 6,712,804 B2 * | 3/2004 | Roue et al. | 604/500 |
| 6,730,112 B2 * | 5/2004 | Levinson | 606/232 |
| 6,746,472 B2 * | 6/2004 | Frazier et al. | 606/232 |
| 6,837,894 B2 * | 1/2005 | Pugsley et al. | 606/139 |
| 6,994,717 B2 * | 2/2006 | Konya et al. | 606/200 |
| 6,997,189 B2 * | 2/2006 | Biggs et al. | 128/898 |
| 7,152,605 B2 * | 12/2006 | Khairkhahan et al. | 128/887 |
| 7,160,314 B2 * | 1/2007 | Sgro et al. | 606/220 |
| 7,316,706 B2 * | 1/2008 | Bloom et al. | 606/232 |
| 7,338,514 B2 * | 3/2008 | Wahr et al. | 606/213 |
| 7,410,489 B2 * | 8/2008 | Dakin et al. | 606/103 |
| 7,431,729 B2 * | 10/2008 | Chanduszko | 606/213 |
| 7,563,267 B2 * | 7/2009 | Goldfarb et al. | 606/151 |
| 7,651,509 B2 * | 1/2010 | Bojarski et al. | 606/139 |
| 7,655,015 B2 * | 2/2010 | Goldfarb et al. | 606/151 |
| 7,678,135 B2 * | 3/2010 | Maahs et al. | 606/232 |
| 7,736,378 B2 * | 6/2010 | Maahs et al. | 606/232 |
| 7,736,379 B2 * | 6/2010 | Ewers et al. | 606/232 |
| 7,740,647 B2 * | 6/2010 | Mueller | 606/232 |
| 7,819,897 B2 * | 10/2010 | Sgro et al. | 606/220 |
| 7,833,233 B2 * | 11/2010 | Mueller et al. | 606/139 |
| 7,842,052 B2 * | 11/2010 | Mueller et al. | 606/148 |
| 7,867,250 B2 * | 1/2011 | Ryan et al. | 606/215 |
| 7,871,425 B2 * | 1/2011 | Jones et al. | 606/224 |
| 7,967,843 B2 * | 6/2011 | Kaiser et al. | 606/232 |
| 8,062,363 B2 * | 11/2011 | Hirpara et al. | 623/13.14 |
| 8,070,826 B2 * | 12/2011 | Ginn | 623/23.72 |
| 8,157,836 B2 * | 4/2012 | Adams | 606/213 |
| 8,162,974 B2 * | 4/2012 | Eskuri et al. | 606/213 |
| 8,206,417 B2 * | 6/2012 | Maahs et al. | 606/232 |
| 8,236,027 B2 * | 8/2012 | Wu | 606/228 |
| 8,246,652 B2 * | 8/2012 | Ruff | 606/216 |
| 8,257,389 B2 * | 9/2012 | Chanduszko et al. | 606/213 |
| 8,257,394 B2 * | 9/2012 | Saadat et al. | 606/232 |
| 8,308,765 B2 * | 11/2012 | Saadat et al. | 606/232 |
| 8,333,777 B2 * | 12/2012 | Schaller et al. | 606/157 |
| 8,372,112 B2 * | 2/2013 | Christianson et al. | 606/213 |
| 8,480,706 B2 * | 7/2013 | Chanduszko et al. | 606/213 |
| 8,500,761 B2 * | 8/2013 | Goldfarb et al. | 606/151 |
| 8,506,595 B2 * | 8/2013 | Houard et al. | 606/232 |
| 8,529,601 B2 * | 9/2013 | Green et al. | 606/232 |
| 2001/0002439 A1 * | 5/2001 | Bonutti et al. | 606/232 |
| 2001/0014814 A1 * | 8/2001 | Bonutti et al. | 606/232 |
| 2001/0039434 A1 * | 11/2001 | Frazier et al. | 606/213 |
| 2001/0039435 A1 * | 11/2001 | Roue et al. | 606/216 |
| 2001/0044639 A1 * | 11/2001 | Levinson | 606/228 |
| 2002/0156499 A1 * | 10/2002 | Konya et al. | 606/213 |
| 2002/0161381 A1 * | 10/2002 | Pugsley et al. | 606/151 |
| 2002/0183787 A1 * | 12/2002 | Wahr et al. | 606/213 |
| 2003/0050665 A1 * | 3/2003 | Ginn | 606/215 |
| 2003/0139819 A1 * | 7/2003 | Beer et al. | 623/23.71 |
| 2003/0181928 A1 * | 9/2003 | Vidlund et al. | 606/151 |
| 2003/0191495 A1 * | 10/2003 | Ryan et al. | 606/213 |
| 2003/0191497 A1 * | 10/2003 | Cope | 606/215 |
| 2003/0199923 A1 * | 10/2003 | Khairkhahan et al. | 606/213 |
| 2004/0073242 A1 * | 4/2004 | Chanduszko | 606/157 |
| 2004/0078054 A1 * | 4/2004 | Biggs et al. | 606/232 |
| 2004/0097986 A1 * | 5/2004 | Adams | 606/151 |
| 2004/0122456 A1 * | 6/2004 | Saadat et al. | 606/157 |
| 2004/0127907 A1 * | 7/2004 | Dakin et al. | 606/72 |
| 2004/0127917 A1 * | 7/2004 | Ginn | 606/151 |
| 2004/0225304 A1 * | 11/2004 | Vidlund et al. | 606/151 |
| 2004/0260317 A1 * | 12/2004 | Bloom et al. | 606/151 |
| 2005/0137450 A1 | 6/2005 | Aronson et al. | |
| 2005/0177180 A1 * | 8/2005 | Kaganov et al. | 606/151 |
| 2005/0251209 A1 * | 11/2005 | Saadat et al. | 606/232 |
| 2005/0267531 A1 * | 12/2005 | Ruff et al. | 606/228 |
| 2005/0273124 A1 | 12/2005 | Chanduszko | |
| 2005/0273135 A1 * | 12/2005 | Chanduszko et al. | 606/213 |
| 2005/0277981 A1 * | 12/2005 | Maahs et al. | 606/213 |
| 2006/0009800 A1 * | 1/2006 | Christianson et al. | 606/213 |
| 2006/0190042 A1 | 8/2006 | Stone et al. | |
| 2006/0217762 A1 * | 9/2006 | Maahs et al. | 606/213 |
| 2006/0241648 A1 | 10/2006 | Bleich et al. | |
| 2006/0259074 A1 * | 11/2006 | Kelleher et al. | 606/213 |
| 2007/0010851 A1 * | 1/2007 | Chanduszko et al. | 606/213 |
| 2007/0010852 A1 * | 1/2007 | Blaeser et al. | 606/213 |
| 2007/0067045 A1 | 3/2007 | Phan et al. | |
| 2007/0073316 A1 * | 3/2007 | Sgro et al. | 606/151 |
| 2007/0073337 A1 * | 3/2007 | Abbott et al. | 606/213 |
| 2007/0129755 A1 * | 6/2007 | Abbott et al. | 606/213 |
| 2007/0167950 A1 | 7/2007 | Tauro et al. | |
| 2007/0198038 A1 * | 8/2007 | Cohen et al. | 606/150 |
| 2007/0203391 A1 * | 8/2007 | Bloom et al. | 600/37 |
| 2007/0225755 A1 * | 9/2007 | Preinitz et al. | 606/213 |
| 2007/0293892 A1 | 12/2007 | Takasu | |
| 2008/0082113 A1 * | 4/2008 | Bishop et al. | 606/151 |
| 2008/0086155 A1 * | 4/2008 | Rothe et al. | 606/153 |
| 2008/0097489 A1 * | 4/2008 | Goldfarb et al. | 606/151 |
| 2008/0132916 A1 * | 6/2008 | Mueller et al. | 606/139 |
| 2008/0132921 A1 * | 6/2008 | Mueller et al. | 606/148 |
| 2008/0132942 A1 * | 6/2008 | Mueller | 606/228 |
| 2008/0132945 A1 * | 6/2008 | Mueller | 606/232 |
| 2008/0147115 A1 * | 6/2008 | O'Malley et al. | 606/216 |
| 2009/0030450 A1 * | 1/2009 | Preinitz et al. | 606/213 |
| 2009/0248066 A1 * | 10/2009 | Wilkie | 606/228 |
| 2009/0318966 A1 * | 12/2009 | Green et al. | 606/232 |
| 2009/0326578 A1 * | 12/2009 | Ewers et al. | 606/213 |
| 2010/0016894 A1 * | 1/2010 | Houard et al. | 606/232 |
| 2010/0094317 A1 * | 4/2010 | Goldfarb et al. | 606/151 |
| 2010/0234947 A1 * | 9/2010 | Ben Rubi et al. | 623/11.11 |
| 2012/0172931 A1 * | 7/2012 | Ben Rubi | 606/228 |

\* cited by examiner

| Pig Identification | Integra ID | Site | Device Implanted | Implant Location | Marking | Measurements | Marking Distance Before Implantation (cm) | Marking Distance After Implantation (cm) | 12/4/09 | 12/5/09 | 12/6/09 | 12/7/09 | 12/9/09 | 12/15/09 | 12/18/09 | 12/22/09 | 12/28/09 | 12/31/09 | 1/4/10 |
|---|---|---|---|---|---|---|---|---|---|---|---|---|---|---|---|---|---|---|---|
| 1 | | | Sihoutte | Left Ear | After Implantation | Only After Implantation | | 7.8 | 6.5 | 5.7 | 6.54 | 6.4 | 6.5 | 6.5 | 6.8 | 6.5 | 6 | 6.5 | 6.5 |
| | | | Juvence | Right Ear | After Implantation | Only After Implantation | | 4.8 | 3.8 | 3.8 | 3.8 | 4.8 | 4.5 | 4.5 | 4.8 | 5 | 5.2 | 5.2 |
| | | | Juvence | Left Ear Base | After Implantation | Only After Implantation | | 4.4 | 5.2 | 4.7 | 4.5 | 4.4 | 4.9 | 4.7 | 4.9 | 4.5 | 4.5 | 4.9 |
| | 10P28 | | Juvence | Right Ear Base | After Implantation | Only After Implantation | | 3.7 | 3.8 | 3.7 | 3.8 | 3.5 | 3.8 | 3.5 | 3.8 | 3.9 | 4.3 | 4 | 4.2 |
| | | | Juvence | Left Ear | Before Implantation | Before and After Implantation | 6.1 | 6.0 | 5.8 | 6.3 | 6.5 | 6.5 | 6.5 | 6.8 | 6.9 | 6.5 | 6.5 | 6.6 |
| | | | Juvence | Right Ear | Before Implantation | Before and After Implantation | 7.0 | 5.1 | 6.5 | 6.5 | 6.5 | 6.5 | 5.8 | 7.2 | 6.5 | 7.1 | 6.5 | 6.7 | 6.6 |
| | | | Juvence | Left Ear Base | Before Implantation | Before and After Implantation | 6.1 | 5.8 | 6.5 | 6.5 | 6.5 | 6.7 | 7.2 | 7 | 6.9 | 7.2 | 6.5 | 6.5 |
| | | | Non-absorbable Polypropylene | Right Ear Base | Before Implantation | Before and After Implantation | 5.8 | 5.8 | 5.8 | 6.2 | 7.5 | 4.5 | 4.8 | 4.8 | 5.4 | 5.5 | 5.3 | 5.8 | 6.8 |
| 2 | 10P29 | | Endotine | Dorsal Neck | Before Implantation | Before and After Implantation | | | | | | | | | | | | | |
| | | | Juvence | Left Ear | Before Implantation | Before and After Implantation | 6.1 | 4.9 | 4.9 | 4.5 | 5.2 | 5.5 | 5.2 | 5.5 | 5.5 | 5 | 5.5 | 4.7 | 5 |
| | | | Juvence | Right Ear | Before Implantation | Before and After Implantation | 6.1 | 4.9 | 6 | 5.5 | 5.5 | 5.5 | 5.9 | 6 | 6.3 | 6 | 4.9 | 5.3 | 6 |
| | | | Sihoutte | Left Ear Base | Before Implantation | Before and After Implantation | 5.4 | 5.4 | 6 | 5.8 | 5.9 | 6.1 | 6.5 | 6.5 | 6.2 | 5.8 | 6.5 | 6.5 | 6.5 |
| | | | Non-absorbable Polypropylene | Right Ear Base | Before Implantation | Before and After Implantation | 6.1 | 5 | 5.5 | 5.4 | 5.9 | 6.5 | 6.5 | 6.7 | 6.5 | 6.5 | 6.5 | 6.4 | 6.5 |
| 3 | 10P30 | | Endotine | Dorsal Neck | Before Implantation | Before and After Implantation | | | | | | | | | | | | | |

FIG. 24

| Pig Identification | Integra ID | Site | Device Implanted | Implant Location | Marking | Measurements | Marking Distance Before Implantation (cm) | Marking Distance After Implantation (cm) | 1/7/10 | 1/14/10 | 1/19/10 | 1/22/10 | 1/27/10 | 1/29/10 | 2/5/10 | 2/12/10 | 2/22/10 | 2/26/10 |
|---|---|---|---|---|---|---|---|---|---|---|---|---|---|---|---|---|---|---|
| 1 | 10P28 | | Silhouette | Left Ear | After Implantation | Only After Implantation | - | 7.8 | 6.3 | 6.8 | 6.5 | 5.9 | 6.5 | 6.1 | 6.5 | 6.2 | 5.8 | 5.5 |
| | | | Juvence | Right Ear | After Implantation | Only After Implantation | - | 4.8 | 4.9 | 5 | 4.8 | 5 | 5.2 | 5.3 | 5.5 | 5 | 5.6 | 5.9 |
| | | | Juvence | Left Ear Base | After Implantation | Only After Implantation | - | 4.4 | 5.1 | 5.1 | 5 | 4.5 | 5 | 4.9 | 4.5 | 4.5 | 4.9 | 4.5 |
| | | | Juvence | Right Ear Base | After Implantation | Only After Implantation | - | 3.7 | 4 | 4 | 4.5 | 4.5 | 4.5 | 4.5 | 4.5 | 4.7 | 5 | 5 |
| | | | Juvence | Left Ear | Before Implantation | Before and After Implantation | 6.1 | 6.0 | 6.5 | 6.3 | 6.1 | 6.5 | 6.5 | 6.6 | 6.5 | 6.5 | 6.9 | 5.2 |
| | | | Juvence | Right Ear | Before Implantation | Before and After Implantation | 7.0 | 5.1 | 6.5 | 7 | 6.9 | 5.9 | 6.9 | 6.9 | 7.1 | 6.9 | 6.6 | 5.2 |
| | | | Juvence | Left Ear Base | Before Implantation | Before and After Implantation | 6.1 | 5.8 | 6.1 | 6.5 | 6 | 6.2 | 6.5 | 6.3 | 6.5 | 6.5 | 6 | 6.5 |
| | | | Non-absorbable Polypropylene | Right Ear Base | Before Implantation | Before and After Implantation | 5.8 | 5.8 | 6 | 5.8 | 5.8 | 6 | 6 | 6.4 | 6.2 | 5.5 | 6 |
| | | | Endotine | Dorsal Neck | Before Implantation | Before and After Implantation | - | | | | | | | | | | | |
| 2 | 10P29 | | Juvence | Left Ear | Before Implantation | Before and After Implantation | 6.1 | 4.9 | 4.8 | 5.5 | 5 | 4.9 | 5 | 5.4 | 5.7 | 5.5 | 5.8 | 5.8 |
| | | | Juvence | Right Ear | Before Implantation | Before and After Implantation | 6.1 | 4.9 | 6.2 | 5.9 | 5.9 | 6.3 | 6 | 6 | 5.7 | 5.9 | 6.2 | 6.5 |
| | | | Silhouette | Left Ear Base | Before Implantation | Before and After Implantation | 5.4 | 5.4 | 6.5 | 6.2 | 6.5 | 6.2 | 6.3 | 5.5 | 5.8 | 5.8 | 6.5 | 6.5 |
| | | | Non-absorbable Polypropylene | Right Ear Base | Before Implantation | Before and After Implantation | 6.1 | 5 | 6.3 | 6.3 | 5.8 | 6.3 | 6.4 | 5.9 | 5.5 | 5.4 | 5.5 |
| 3 | 10P30 | | Endotine | Dorsal Neck | Before Implantation | Before and After Implantation | - | | | | | | | | | | | |

FIG. 25

IMPLANTED MEDICAL DEVICE USEFUL FOR COSMETIC SURGERY

CROSS-REFERENCE TO RELATED APPLICATIONS

This application claims priority from U.S. Provisional Application 61/218,958 dated Jun. 21, 2009 and PCT application no. PCT/IL10/00485 dated Jun. 21, 2010.

FIELD OF THE INVENTION

The present invention relates to innovations for minimally invasive plastic and/or cosmetic surgery. More specifically the present invention relates to methods for manipulating tissue placement using anchors and sutures. Conducting tools are also described, for delivering these elements through the tissue and fixing them as desired. The system and method arc useful for smoothing wrinkles, reconstructive purposes, and the like.

BACKGROUND OF THE INVENTION

US patent application US20070293892 discloses a surgical thread for plastic surgery which effectively removes sagging and wrinkling of skin. The device comprises a thread shaped member comprised of a thread body, to be implanted in the inside layers of the skin, partially formed in its longitudinal direction with projections for anchoring in the inside skin layers, wherein at least the thread body is comprised of an absorbable thread, and the thread body or the projections are formed with residual film parts which will not be absorbed by the inside skin layers, and a method of imparting tension to the skin using the same. In FIGS. 1*a-b* this device is depicted. However the system is somewhat primitive in its capabilities. For example, it cannot provide independent control over tension between successive anchoring projections. Nor does it allow for both tension and compression to be provided by the same device. Finally the device does not allow for certain operations such as gathering tissue together.

US patent application 2007/067045 discloses an implant that reduces wrinkles, in the shape of a cylinder with a constant or varying cross-section and length. The implant contains a gel of limited flow capability. The implant can also be a balloon that may or may not have multiple compartments optionally filled with fluid. However the system cannot provide independent control over tension between given points. Nor does it allow for both tension and compression to be provided by the same device. Finally the device does not allow for certain operations such as gathering tissue together.

PCT application WO06065837 provides a cosmetic implant comprising a filament made from a biocompatible elastomer. The elastomeric filament can be injected or pulled under one or more wrinkles. Once implanted under the wrinkle(s), the filament lifts and supports the tissue above it. Such lifting lessens (and possibly removes altogether) the appearance of the wrinkle(s). Again however the system cannot provide independent control over tension between given anchoring points. Nor does it allow for both tension and compression to be provided by the same device. Finally the system does not allow for certain operations such as gathering tissue together at a point.

Other known implants are the cosmetic implants provided by silhouette-lift (shown in FIG. 1B). The cosmetic implants are sutures are made from polypropylene and contain cones located along the suture. The suture is inserted via an incision, deployed, anchored via the cones and then the suture is fixated to the fascia thereby a tension is produced which lifts the sagging tissue.

However, such a suture provides a single point fixation. In other words, the fixation of the cones to the tissue is merely along the suture's curve. Therefore, in order, for example, to lift an eyebrow several incisions will have to be made. Each incision increases the patient's healing time and increases the scars caused to the patient.

Therefore, there is still a long felt need for an implantable medical device adapted for repositioning tissues and/or other structures with independently controllable multiple tensioning means which will be a multi point fixation that will require a single incision.

SUMMARY OF THE INVENTION

It is one object of the present invention to provide a minimally invasive multipoint fixation device adapted to laparoscopically locally reposition body tissues. The device comprises:
  a. At least one distal anchor reversibly connectable to a first tissue location;
  b. At least one proximal anchor reversibly connectable to a second tissue location;
  c. An elongated connecting element, having a main longitudinal axis, adapted to interconnect between the distal anchor and the proximal anchor;

It is within the scope of the present invention that the distal and proximal anchors are characterized by at least two configurations: (i) a FOLDED CONFIGURATION, in which the distal and proximal anchors are substantially parallel to the main longitudinal axis; and, (ii) a DEPLOYED CONFIGURATION, in which the distal anchor is positioned at an angle A with respect to the main longitudinal axis, and the proximal anchor is positioned at an angle B with respect to the main longitudinal axis. The fixation device further comprises deployment means adapted to deploy the distal and proximal anchors by reconfiguring the same from the FOLDED CONFIGURATION to the DEPLOYED CONFIGURATION.

It is another object of the present invention to provide the fixation device as defined above, wherein the fixation device further comprises tension varying means connectable to the distal and proximal anchors, adapted to alter parameters selected from a group consisting of: the length of the elongated connecting element; and, the tension applied on the elongated connecting element, such that the first and the second tissue locations are repositioned with respect to each other according to the parameters.

It is another object of the present invention to provide the fixation device as defined above, wherein each of the distal and the proximal anchors comprises at least two hinged wings; each of the hinged wing being characterized by at least two configurations: (i) a FOLDED CONFIGURATION, in which the wings are substantially parallel to the main longitudinal axis, such that the anchor is folded and, (ii) a DEPLOYED CONFIGURATION, in which the wings are positioned at angles selected from a group consisting of the angles A or B, such that the anchor is deployed.

It is another object of the present invention to provide the fixation device as defined above, wherein the deployment mechanism comprises at least one deployment tool, reversible coupled to at least one of the wings, such that application of a mechanical force by the at least one deployment tool to the wings is adapted to reconfigure at least one of the wings from the FOLDED CONFIGURATION into the DEPLOYED CONFIGURATION so as to deploy the anchors.

It is another object of the present invention to provide the fixation device as defined above, wherein the deployment tool is adapted to be coupled to at least one of the wings, when the wings are in the DEPLOYED CONFIGURATION, so as to increase the mechanical strength of the same.

It is another object of the present invention to provide the fixation device as defined above, wherein at least one of the wings comprises at least one groove adapted to incorporate the at least one deployment tool.

It is another object of the present invention to provide the fixation device as defined above, wherein the at least one deployment tool is selected from a group consisting of: a rod, a stick, a shaft, a needle, a pin, a wire, a thread, a suture, a string, a cord, a fiber, a rope, or any combination thereof.

It is another object of the present invention to provide the fixation device as defined above, wherein the mechanical force is selected from a group consisting of: pushing forces, pulling forces, shearing forces, bending forces, torque, or any combination thereof.

It is another object of the present invention to provide the fixation device as defined above, wherein the elongated connecting element is selected from a group consisting of: a rigid element or a non-rigid element.

It is another object of the present invention to provide the fixation device as defined above, wherein the elongated connecting element is selected from a group consisting of: a thread, a suture, a string, a cord, a fiber, a rope, a wire, a rod, a stick, a shaft, or any combination thereof.

It is another object of the present invention to provide the fixation device as defined above, wherein each of the distal and the proximal anchors are convertible from the FOLDED CONFIGURATION to the DEPLOYED CONFIGURATION by rotation of the same relatively to the longitudinal axis.

It is another object of the present invention to provide the fixation device as defined above, wherein the distal and the proximal anchors comprise at least one attachment element selected from a group consisting of: barbs, cogs, spikes, or any combination thereof; the attachment elements adapted to connect the distal and the proximal anchors to the first and second tissue locations.

It is another object of the present invention to provide the fixation device as defined above, wherein the fixation device further comprises a conducting tool adapted to keep the distal and proximal anchors in the FOLDED CONFIGURATION, and to facilitate the conduction of the distal and proximal anchors to the first and second tissue locations.

It is another object of the present invention to provide the fixation device as defined above, wherein the angles A and B are in a range of about 0.1 degrees and about 180 degrees.

It is another object of the present invention to provide the fixation device as defined above, wherein the angles A and B are about 90 degrees.

It is another object of the present invention to provide the fixation device as defined above, wherein the tension varying means is further adapted to alter the parameters by a locking means adapted to affix the proximal anchor to the elongated connecting element.

It is another object of the present invention to provide the fixation device as defined above, wherein the elongated connecting element is adapted to deploy at least one of the distal anchor or the proximal anchor.

It is another object of the present invention to provide the fixation device as defined above, wherein the first and second tissue locations are located between the dermis and the muscle.

It is another object of the present invention to provide the fixation device as defined above, wherein the distal and proximal anchors are comprised of materials selected from the group consisting of: polyethylene, polypropylene, polyurethanes, poly (methyl methacrylate), polycarbonates, silicone rubber, biodegradable polymers, synthetic and natural occurring materials including polyalkylene esters, polylactic acid and its co-polymers, polyvinyl esters, polyvinyl alcohol, polyanhydrides, and polycarbonates, Polydioxanone (PDO), Polycaprolactone (PCL), Polylactic acid (PLA), Polyglycolic acid (PGA), Adipic acid, PEG, glutamic acid, polymers, metals, metal alloys, ceramics, shape memory alloys, hydroxyapaptite, and glass.

It is another object of the present invention to provide the fixation device as defined above, wherein the distal and proximal anchors, the elongated connecting element, and the conducting tool comprise bioactive coatings selected from the group consisting of: proteins, growth factors, antigens, carbon-like diamond, carbon, hyaluronic acid, collagen, silver, gold, or any combination thereof.

It is another object of the present invention to provide the fixation device as defined above, wherein the distal elongated connecting element is made of an elastic material.

It is another object of the present invention to provide the fixation device as defined above, wherein the fixation device is adapted to create a network of anchors.

It is another object of the present invention to provide a minimally invasive multipoint fixation method for laparoscopically locally repositioning bodily tissues. The method comprises steps of:
a. providing a minimally invasive multipoint fixation device adapted to laparoscopically locally reposition body tissues, the device comprising: (i) at least one distal anchor reversibly connectable to a first tissue location; (ii) at least one proximal anchor reversibly connectable to a second tissue location; (iii) an elongated connecting element, having a main longitudinal axis, adapted to interconnect between the distal anchor and the proximal anchor;
b. connecting the distal anchor to the proximal anchor via the elongated connecting element;
c. anchoring the distal anchor at the first tissue location;
d. anchoring the proximal anchor at the second tissue location;

It is within the scope of the present invention that step (a) is performed by providing a fixation device with distal and proximal anchors which are characterized by at least two configurations: (i) a FOLDED CONFIGURATION, in which the distal and proximal anchors arc substantially parallel to the main longitudinal axis; and, (ii) a DEPLOYED CONFIGURATION, in which the distal anchor is positioned at an angle A with respect to the main longitudinal axis, and the proximal anchor is positioned at an angle B with respect to the main longitudinal axis. Steps (c)-(d) comprise additional steps of reconfiguring the distal and proximal anchors from the FOLDED CONFIGURATION to the DEPLOYED CONFIGURATION via a deployment means.

It is another object of the present invention to provide the fixation method as defined above, which further comprises steps of: (e) providing the fixation device with tension varying means connectable to the distal and proximal anchors; (f) altering the parameters selected from a group consisting of: the length of the elongated connecting element; and, the tension applied on the elongated connecting element; (g) repositioning the first and the second tissue locations with respect to each other according to the parameters; (h) securing the proximal anchor to the elongated connecting element.

It is another object of the present invention to provide the fixation method as defined above, which further comprises steps of: (e) providing the fixation device with distal and the proximal anchors comprises at least two hinged wings; each of the hinged wing being characterized by at least two configurations: (i) a FOLDED CONFIGURATION, in which the wings are substantially parallel to the main longitudinal axis, such that the anchor is folded and, (ii) a DEPLOYED CONFIGURATION, in which the wings are positioned at angles selected from a group consisting of the angles A or B, such that the anchor is deployed.

It is another object of the present invention to provide the fixation method as defined above, which further comprises step of deploying the distal and proximal anchors by deploying the wings.

It is another object of the present invention to provide the fixation method as defined above, which further comprises steps of: providing the fixation device with a deployment mechanism which comprises at least one deployment tool reversible coupled to at least one of the wings; and, applying a mechanical force by the at least one deployment tool to the wings, and thereby reconfiguring the at least one of the wings from the FOLDED CONFIGURATION into the DEPLOYED CONFIGURATION.

It is another object of the present invention to provide the fixation method as defined above, which further comprises step of coupling the deployment tool to at least one of the wings, when the wings are in the DEPLOYED CONFIGURATION, and thereby increasing the mechanical strength of the wings.

It is another object of the present invention to provide the fixation method as defined above, which further comprises step of incorporating the at least one deployment tool in at least one groove located within at least one of the wings.

It is another object of the present invention to provide the fixation method as defined above, wherein the mechanical force is selected from a group consisting of: pushing forces, pulling forces, shearing forces, bending forces, torque, or any combination thereof.

It is another object of the present invention to provide the fixation method as defined above, wherein the wherein the elongated connecting element is selected from a group consisting of: a rigid element or a non-rigid element.

It is another object of the present invention to provide the fixation method as defined above, wherein the elongated connecting element is selected from a group consisting of: a thread, a suture, a string, a cord, a fiber, a rope, a wire, a rod, a stick, a shaft, or any combination thereof.

It is another object of the present invention to provide the fixation method as defined above, wherein the steps (c) and (d) are performed by rotating the distal and proximal anchors relatively to the longitudinal axis.

It is another object of the present invention to provide the fixation method as defined above, wherein the distal and the proximal anchors comprise at least one attachment elements selected from a group consisting of: barbs, cogs, spikes, or any combination thereof; the attachment elements adapted to connect the distal and the proximal anchors to the first and second tissue locations.

It is another object of the present invention to provide the fixation method as defined above, which further comprises steps of: providing the fixation device with a conducting tool for keeping the distal and proximal anchors in the FOLDED CONFIGURATION; and, facilitating the insertion of the distal and proximal anchors to the first and second tissue locations via the conducting tool while performing the steps (c)-(d).

It is another object of the present invention to provide the fixation method as defined above, which further comprises steps of inserting the distal and proximal anchors to the conducting tool before the steps (c)-(d).

It is another object of the present invention to provide the fixation method as defined above, wherein the angles A and B are in a range of about 0.1 degrees and about 180 degrees.

It is another object of the present invention to provide the fixation method as defined above, wherein the angles A and B are about 90 degrees.

It is another object of the present invention to provide the fixation method as defined above, wherein the step of altering the parameters is performed by affixing the proximal anchor to the elongated connecting element via a locking means.

It is another object of the present invention to provide the fixation method as defined above, which further comprises step of deploying at least one of the distal anchor or the proximal anchor via the elongated connecting element.

It is another object of the present invention to provide the fixation method as defined above, wherein the steps (c) and (e) are performed such that the first and second tissue locations are located between the dermis and the muscle;

It is another object of the present invention to provide the fixation method as defined above, which further comprises step of selecting the materials of the distal and proximal anchors from the group consisting of: polyethylene, polypropylene, polyurethanes, poly (methyl methacrylate), polycarbonates, silicone rubber, biodegradable polymers, synthetic and natural occurring materials including polyalkylene esters, polylactic acid and its co-polymers, polyvinyl esters, polyvinyl alcohol, polyanhydrides, and polycarbonates, Polydioxanone (PDO), Polycaprolactone (PCL), Polylactic acid (PLA), Polyglycolic acid (PGA), Adipic acid, PEG, glutamic acid, polymers, metals, metal alloys, ceramics, shape memory alloys, hydroxyapaptite, and glass.

It is another object of the present invention to provide the fixation method as defined above, which further comprises step of coating the distal and proximal anchors, the elongated connecting element, and the conducting tool with a material selected from the group consisting of: proteins, growth factors, antigens, carbon-like diamond, carbon, hyaluronic acid, collagen, silver, gold, or any combination thereof.

It is another object of the present invention to provide the fixation method as defined above, which further comprises step of repeating the steps (a)-(f) for creating a network of anchors interconnected between each other by a plurality of elongated connecting elements, and thereby setting the tension of the elongated connecting elements independently.

It is another object of the present invention to provide the fixation method as defined above, which further comprises step of providing the elongated connecting element which is made from an elastic material.

It is another object of the present invention to provide the fixation method as defined above, which further comprises step of sensing the tension of the elongated connecting element via a sensing means.

It is another object of the present invention to provide the fixation method as defined above, which further comprises steps of: removing at least part of the deployment mechanism from the fixation device; and, leaving the distal and proximal anchors in the DEPLOYED CONFIGURATION with a predetermined tension in the elongated connecting element therebetween.

It is another object of the present invention to provide the fixation method as defined above, which further comprises step of cutting at least one unused part of the elongated connecting element.

It is another object of the present invention to provide the fixation method as defined above, which further comprises steps of implanting the distal and proximal anchors at the first and second tissue locations.

BRIEF DESCRIPTION OF THE DRAWINGS

The present invention will be understood and appreciated more fully from the following detailed description taken in conjunction with the appended drawings in which:

FIG. 24 shows the implant measurements raw data.

FIG. 25 shows the implant measurements raw data.

Figure 1A:
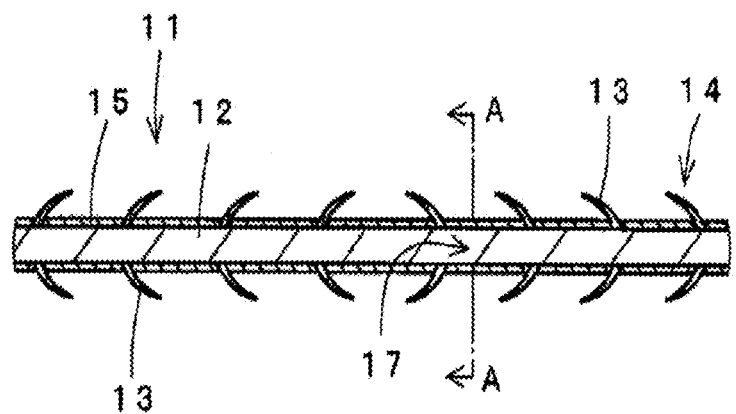
FIGS. 1A-1B shows prior art concerning contour Threads™.

While the invention is susceptible to various modifications and alternative forms, specific embodiments thereof have been shown by way of example in the drawings. The components in the drawings are not necessarily to scale, emphasis instead being placed upon clearly illustrating the principles of the present invention. It should be understood, however, that the description herein of specific embodiments is not intended to limit the invention to the particular forms disclosed, but on the contrary, the intention is to cover all modifications, equivalents, and alternatives falling within the spirit and scope of the invention.

DETAILED DESCRIPTION OF THE PRESENT INVENTION

The following description is provided in order to enable any person skilled in the art to make use of said invention and sets forth the best modes contemplated by the inventor of carrying out this invention. Various modifications, however, will be apparent to those skilled in the art, since the generic principles of the present invention have been defined specifically to provide an implantable medical device and a method of using the same, and therefore the invention is not limited by that which is illustrated in the figures and described in the specification, but only as indicated in the accompanying claims, with the proper scope determined only by the broadest interpretation of said claims.

The present invention discloses a minimally invasive multipoint fixation device adapted to laparoscopically locally reposition body tissues. The device comprises:

a. At least one distal anchor reversibly connectable to a first tissue location;

b. At least one proximal anchor reversibly connectable to a second tissue location;

c. An elongated connecting element, having a main longitudinal axis, adapted to interconnect between the distal anchor and the proximal anchor;

It is within the scope of the present invention that the distal and proximal anchors are characterized by at least two configurations: (i) a FOLDED CONFIGURATION, in which the distal and proximal anchors are substantially parallel to the main longitudinal axis; and, (ii) a DEPLOYED CONFIGURATION, in which the distal anchor is positioned at an angle A with respect to the main longitudinal axis, and the proximal anchor is positioned at an angle B with respect to the main longitudinal axis. The fixation device further comprises deployment means adapted to deploy the distal and proximal anchors by reconfiguring the same from the FOLDED CONFIGURATION to the DEPLOYED CONFIGURATION.

The term 'conducting tool' refers hereinafter to a generally long thin hollow cylindrical or oval device adapted to be inserted within a small incision, in a fashion similar to a catheter/canula or laparoscopic/endoscopic tool.

The term 'anchor' refers hereinafter to a barbed structure adapted to be embedded irreversibly within bodily tissues, being rigidly held in place due to its barbs which are penetrating the surrounding tissue.

The term 'deployed' refers hereinafter to a fully extended state of an anchor.

The term "biocompatible materials" refers hereinafter to materials that have the ability to perform with an appropriate host response in a specific application. Biocompatible materials have the quality of not having toxic or injurious effects on biological systems.

The term "biodegradable materials" refers hereinafter to materials that are degraded by the body's enzymatic pathways through a reaction against "foreign" material; or simply by hydrolysis. Examples of biodegradable materials are polymers such as Polydioxanone (PDO), Polycaprolactone (PCL), Polylactic acid (PLA), Polyglycolic acid (PGA), Adipic acid, PEG and glutamic acid.

The term 'implantable' refers to the property of an object which can be introduced into the human body at a distance from the location wherein the implanting device enters the body.

The term "repositioning" or 'repositioned' refers hereinafter to any surgical operations possible including cosmetic surgeries selected from remolding and/or reconstructing both soft and/or hard tissues; repairing tears, holes, or apertures in soft biological tissue; organ repositioning and/or reconstruction; wrinkle removal; face lifting; intensive and/or immediate care for repairing ruptures of blood vessels, skin, or other tissue; repair of lacerations; orthopedic surgeries; dental surgeries; soft and hard tissue reattachment; and others that will be obvious to one skilled in the art.

The term "remolding" refers to a process of reshaping, in particular reshaping skin, organ, and/or muscle. Thus cosmetic surgery for instance often involves a process of remolding the face tissue and/or muscle.

Figure 1B:

The term "single point fixation" refers to a fixation made by anchors for repositioning of tissues in a single point (an example of a single point fixation can be seen in FIGS. 1A and 1B). It should be pointed out that there might be multiple anchors along the suture; however, if the fixation is made along the path/curve of the suture, it will be regarded as single point fixation.

The term "multi-point fixation" refers to a fixation made by anchors for repositioning of tissues in multiple number of points. In a multi point fixation, the fixation to the tissue is provided at an angle A relatively to the suture. Angle A can be in the range of above 0 and below 180 degrees, preferably 90 degrees. An example of multi point fixation device can be seen in FIG. 2, in which the fixation to the tissue is provided at an angle A relatively to the suture.

The term "locally" refers herein after to a procedure that is carried out locally without having a need to be attached to the fascia layer and/or to the bone.

The term "minimally invasive procedure" refers hereinafter to any procedure (surgical or otherwise) that is less invasive than open surgery used for the same purpose. During minimally invasive procedures the physician enters body of a patient through an incision made to the skin or through a body cavity or anatomical opening, but with the smallest damage possible.

According to the present invention, the incision made is big enough to enable a working port to perform the procedure but small enough to provide a short healing time and a short downtime.

The term 'pushing' is a mechanical operation in which a mechanical force is actuated in a direction which is distal to the operator.

The term 'pulling' is a mechanical operation in which a mechanical force is actuated in a direction which is proximal to the operator.

In accordance with the present invention, a device and method for tissues and skin manipulation is provided. For example, according to one embodiment of the present invention, the device is provided with ability to smooth skin by stretching or compressing the same. This procedure may also be used reduce wrinkles and achieve other aesthetic results.

According to other embodiments of the present invention, the device may also be used to lift tissue and reposition it.

In general any esthetic procedure, in which a skin is reposition from on point to another point is performed, can be achieved via the device of the present invention.

One of the main advantages of the device provided by the present invention is the fact that the achieved esthetic outcome is provided via a minimally invasive method (e.g., a laparoscopic procedure).

More specifically, the following features are the main advantages and the core concepts provided by the present invention:

1. A multi-point fixation (the term will be explained in the following description);
2. Single entrance incision enabling a fast recovering and a minimal scar;
3. Local procedure—while other known in the art procedures (such as the implant provided by silhouette lift) is fixated to the temporal fascia and/or bone, the present invention is not attached to the fascia and/or bone and hence can be carried out locally. Since sometimes the tissues to be repositioned are located far away from the fascia, there is major advantage to a device that can enable a local procedure.
4. The reposition of the tissues may be easily and precisely controlled via a tension varying means (as described below).
5. A network of anchoring elements interconnected by elongated connecting elements may be created whilst the tension between each of pair of said anchoring elements (created by fixing the anchoring elements to the tissues) may be set independently.

The present invention is intended in one embodiment for facial rejuvenation by lifting and repositioning sagging face tissues using a laparoscopic technique. According to another embodiment, the device is intended for breast lifting, posterior (buttocks) lifting, etc.

According to some embodiments, the main target audiences of the present invention are women and men aged 35-70.

According to some embodiments, the present invention may be utilized for facial nerve paralysis. Facial nerve paralysis is a common problem that involves the paralysis of any structures innervated by the facial nerve. The pathway of the facial nerve is long and relatively convoluted, so there are a number of causes that may result in facial nerve paralysis. The most common is Bell's palsy, an idiopathic disease that may only be diagnosed by exclusion.

The device of the current invention may be beneficially employed for stretching a wrinkle or reposition tissues in the following manner: an anchor as described above is affixed to the facial muscle tissue and to the skin at one side of the wrinkle. According to another embodiment, the anchor can be affixed underneath the muscles above the bones.

Figure 2:
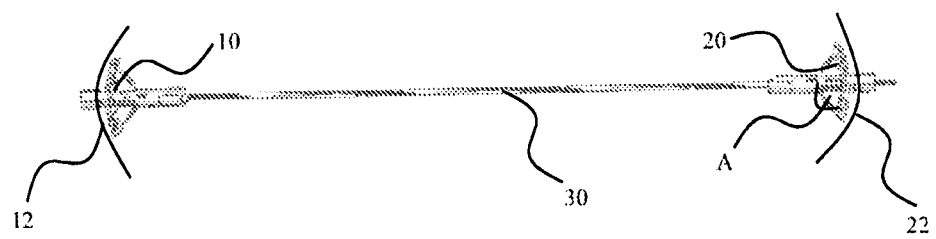
FIG. 2 schematically illustrates specific embodiment of the distal anchor according to the present invention.

Reference is now made to FIG. 2 which schematically illustrates a specific embodiment of a distal anchor 10; and, a proximal anchor 20 interconnected therebetween. This figure illustrates the final result of the anchoring process of distal and proximal anchors 10 and 20 by using the fixation device of the present invention which is discloses below. Each of the anchors comprises attachment elements which may be example: barbs, cogs, spikes, etc. The attachment elements are adapted to connect distal anchor 10 to a first tissue location 12, and to connect proximal anchor 20 to second tissue location 22. The connection of the attachment elements may be performed by hooking into the surrounding tissue and becoming entrenched (as in FIGS. 11a-c). Once distal and proximal anchors 10 and 20 are anchored and entrenched at first and second tissue locations 12 and 22, they serve as anchors. This means that they can be used for pulling and repositioning first and the second tissue location 12 and 22 with respect to each other by means of an elongated connecting element 30 (e.g., a thread, a suture, a string, a cord, a fiber, a rope, a wire, a rod, a stick, a shaft, etc.).

According to different embodiments of the present invention, the elongated connecting element may be selected from a group consisting of: a rigid element or a non-rigid element.

It should be pointed out that according to one embodiment of the present invention, the distal and the proximal anchors may comprise attachment elements on both sides of the anchors. According to another embodiment, the anchors may comprise the attachment elements on only one side of the anchors.

According to some embodiments, the distal and the proximal anchors 10 and 20 are useful for being anchored in tissue layers under muscle layers (e.g., between the dermis and the muscle).

Figure 3A:
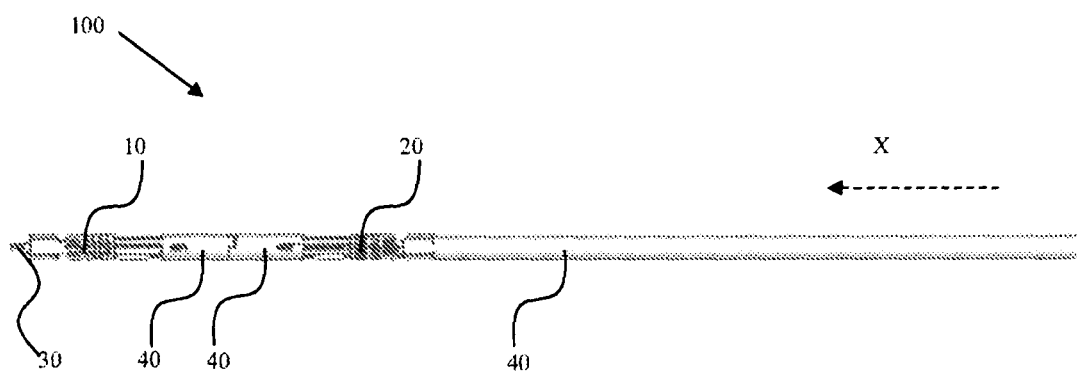
FIGS. 3a-b schematically illustrates the anchors of the present invention with two hinges wings.
Figure 3B:
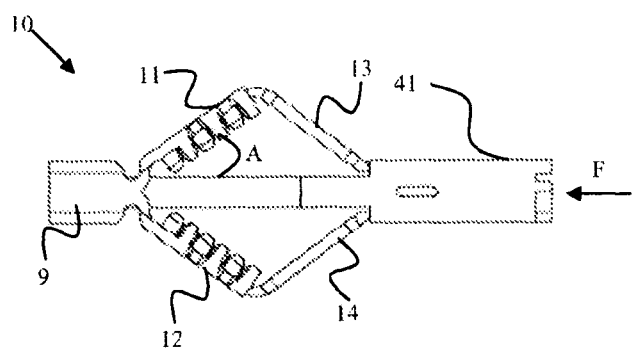

Reference is now made to FIGS. 3a-b which schematically illustrate a specific embodiment of a minimally invasive multipoint fixation device 100 according to the present invention. Fixation device 100 of FIGS. 3a-b is adapted to laparoscopically locally reposition body tissues. Fixation device 100 comprises the following main components:

a. Distal anchor 10 reversibly connectable to first tissue location 12 (not shown);
b. Proximal anchor 20 reversibly connectable to a second tissue location (not shown);
c. Elongated connecting element 30, having a main longitudinal axis X, adapted to interconnect between distal anchor 10 and proximal anchor 20;

A main novel feature of the present invention is the ability of distal and proximal anchors 10 and 20 to be deployed. For their deployment, distal and proximal anchors 10 and 20 are characterized by two configurations: (i) a FOLDED CONFIGURATION (as illustrated in FIG. 3a), in which distal and proximal anchors 10 and 20 are substantially parallel to axis X; and, (ii) a DEPLOYED CONFIGURATION (shown in FIG. 4c and in FIG. 5c), in which distal anchor 10 is positioned at an angle A with respect to axis X, and proximal anchor 20 is positioned at an angle B with respect to axis X.

According to different embodiment of the present invention, angles A and B may be in a range of about 0.1 degrees and about 180 degrees. Preferably, said angles A and B are about 90 degrees.

An additional novel feature of fixation device 100 of the present invention is a deployment means 40 which is adapted to deploy distal and proximal anchors 10 and 20 by reconfiguring the same from the FOLDED CONFIGURATION to the DEPLOYED CONFIGURATION.

According to different embodiments of the present invention, elongated connecting element 30 is selected from a group consisting of: a thread, a suture, a string, a cord, a fiber, a rope, a wire, a rod, a stick, a shaft, or any combination thereof.

According to the specific embodiment of fixation device 100, elongated connecting element 30 is a suture.

FIG. 3b schematically illustrates distal anchor 10 which comprises two hinged wings 11 and 12 each of which is characterized by two configurations: (i) a FOLDED CONFIGURATION, in which said wings are substantially parallel to axis X, such that distal anchor 10 is folded; and, (ii) a DEPLOYED CONFIGURATION, in which hinged wings 11 and 12 are positioned at an angle A relatively to axis X, such that distal anchor 10 is deployed.

According to the embodiment of the present invention illustrated in FIG. 2, it can be seen that distal and proximal anchors 10 and 20 are similar to each other by means of their geometrical structure. Therefore, proximal anchor 20 also comprises two hinged wings each of which is characterized by two configurations: (i) a FOLDED CONFIGURATION, in which said wings are substantially parallel to axis X, such that proximal anchor 20 is folded; and, (ii) a DEPLOYED CONFIGURATION, in which the hinged wings are positioned at an angle B (not shown) relatively to axis X, such that proximal anchor 20 is deployed.

For the deployment of distal anchor 10, deployment mechanism 40 comprises a deployment tool 41, reversible coupled to wings 10 and 11 via rigid rods 13 and 14. Deployment tool 41 is adapted to reconfigure wings 11 and 12 from the FOLDED CONFIGURATION into the DEPLOYED CONFIGURATION by applying a mechanical pulling force F on the same, and thereby to deploy distal anchor 10. The mechanical pulling force F which deploys distal anchor 10 is applied on deployment tool 41 via a pushing rod (not shown) which is an additional element of deployment mechanism 40. This deployment is performed while the left end 9 of distal anchor 10 is held by the operator and/or via other means (e.g., an elongated connecting element). Alternatively, the deployment of distal anchor 10 may be performed by pulling left end 9 towards the proximal direction.

According to different embodiments, the mechanical forces which may activate the deployment of distal and proximal anchors 10 and 20 may be for example: pushing forces, pulling forces, shearing forces, bending forces, torque, or any combination thereof.

Figure 4A:
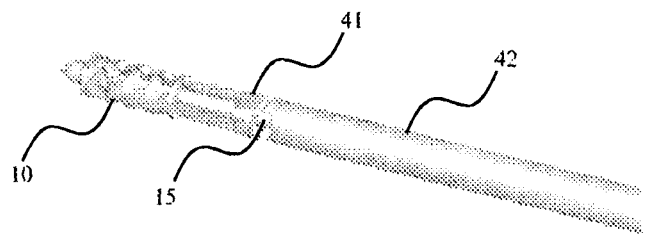
FIGS. 4a-c schematically illustrate a possible method for the reconfiguration of a distal anchor from the FOLDED CONFIGURATION into the DEPLOYED CONFIGURATION.
Figure 4B:
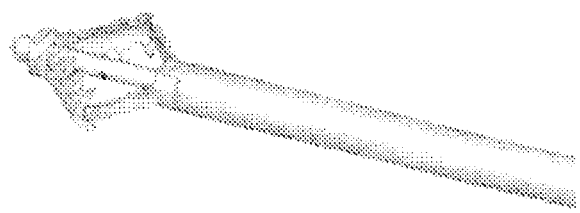
Figure 4C:
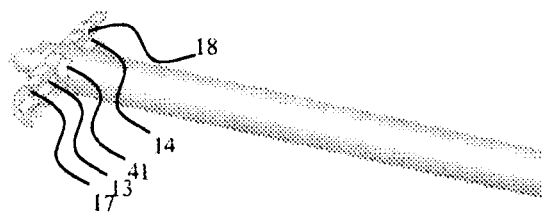

FIGS. 4a-c illustrate a possible method for the reconfiguration of distal anchor 10 from the FOLDED CONFIGURATION into the DEPLOYED CONFIGURATION.

In FIG. 4a, distal anchor 10 is illustrated in the FOLDED CONFIGURATION. In this figure illustrated a pushing rod 42 which is adapted to actuate a pushing mechanical force F on deployment tool 41 to deploy distal anchor 10. In the process of deployment of distal anchor 10, deployment tool 41 slides on rigid rod 15 when pushed by pushing rod 42.

In FIG. 4b illustrated distal anchor 10 in the process of its deployment between the FOLDED CONFIGURATION and the DEPLOYED CONFIGURATION. In this process, pushing rod 42 has begun to push deployment tool 41, and as a result of that, wings 11 and 12 are deployed.

In FIG. 4c illustrated distal anchor 10 in the DEPLOYED CONFIGURATION. In this configuration, deployment tool 41 is coupled to wings 11 and 12, so as to increase the mechanical strength of the distal anchor in the DEPLOYED CONFIGURATION. The increase of the mechanical strength is performed by fixation of rigid rods 13 and 14 in grooves 17 and 18 located within wings 11 and 12.

Figure 5A:
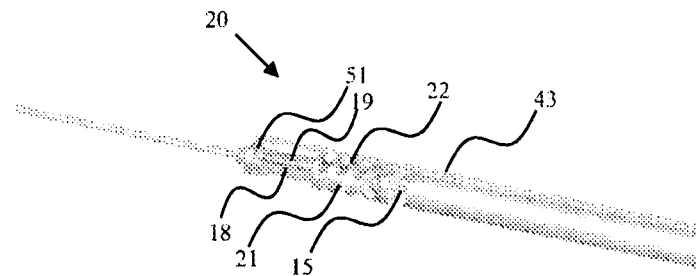
FIGS. 5a-c schematically illustrate a possible method for the reconfiguration of a proximal anchor from the FOLDED CONFIGURATION into the DEPLOYED CONFIGURATION.
Figure 5B:
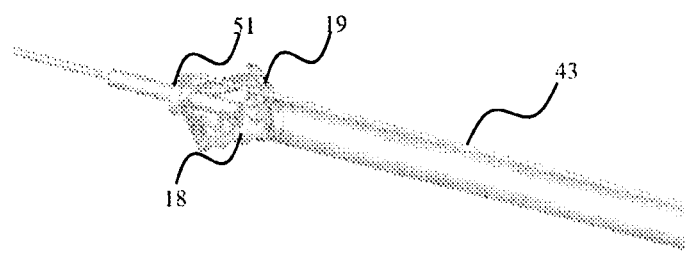
Figure 5C:
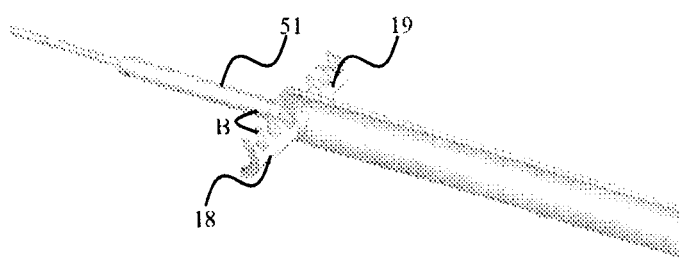

FIGS. 5a-c illustrate a possible method for the reconfiguration of proximal anchor 20 from the FOLDED CONFIGURATION into the DEPLOYED CONFIGURATION.

In FIG. 5a, proximal anchor 20 is illustrated in the FOLDED CONFIGURATION. In this figure illustrated a pulling suture 43 which is adapted to actuate a pushing force F on deployment tool 51 (which is part of deployment mechanism 40) to deploy proximal anchor 20. When pushing force F is actuated on deployment tool 51, rigid rods 18 and 19 deliver said force F to wings 21 and 22 of proximal anchor 20, and a result of that, proximal anchor is deployed. In the process of deployment of proximal anchor 20, deployment tool 40 slides on rigid rod 15 when pulled by pulling suture 43.

In FIG. 5b illustrated proximal anchor 20 in the process of its deployment, between the FOLDED CONFIGURATION and the DEPLOYED CONFIGURATION. In this process, pulling suture 43 has begun to pull deployment tool 51, and as a result of that, wings 18 and 19 are deployed.

In FIG. 5c illustrated proximal anchor 20 in the DEPLOYED CONFIGURATION. In this configuration, deployment tool 51 is coupled to wings 18 and 19, so as to increase the mechanical strength of proximal anchor 20 in the DEPLOYED CONFIGURATION. The increase of the mechanical strength is performed by fixation of rigid rods (not shown) in grooves (not shown) located within wings 18 and 19.

According to different embodiments of the present invention, the deployment tool may be for example: a rod, a stick, a shaft, a needle, a pin, a wire, a thread, a suture, a string, a cord, a fiber, a rope, or any combination thereof.

According to different embodiments of the present invention, the deployment tool may be connected to an element (as the pushing rod and the pulling suture) which is adapted to actuate the deployment tool for the deployment of an anchor. This element can be for example: a rod, a stick, a shaft, a needle, a pin, a wire, a thread, a suture, a string, a cord, a fiber, a rope, or any combination thereof.

In FIG. 5c also illustrated angle B which is the angle the deployed proximal anchor 20 with respect to axis X.

Figure 6:
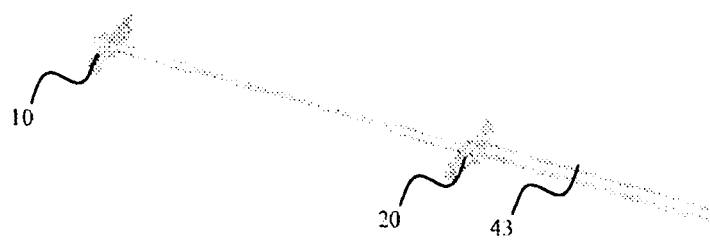
FIG. 6 schematically illustrates distal anchor 10 and proximal anchor 20 in their DEPLOYED CONFIGURATION.

FIG. 6 schematically illustrates distal anchor 10 and proximal anchor 20 in their DEPLOYED CONFIGURATION. In this figure, it can be seen that the pushing rod which deployed distal anchor 10 has been removed, and pulling suture 43 which deployed proximal anchor 20 is illustrated.

Figure 7:
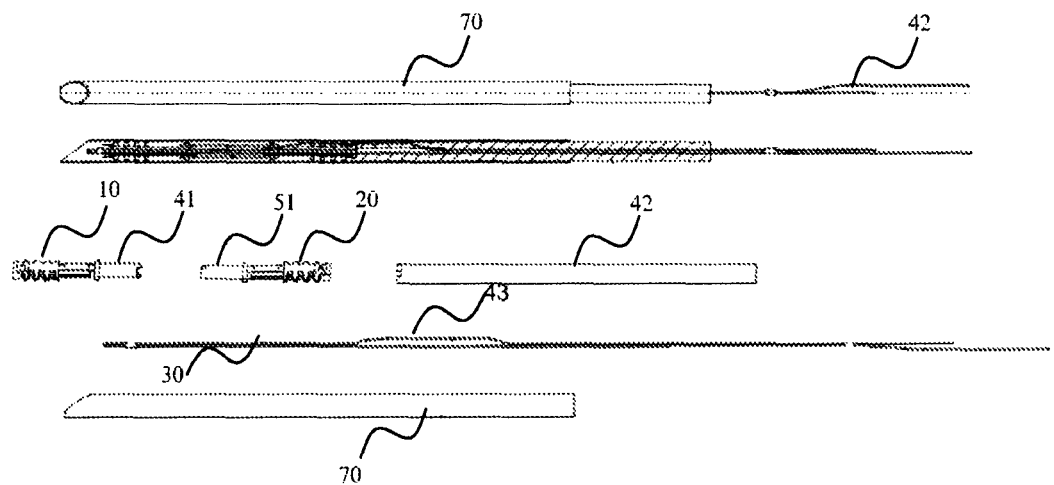
FIG. 7 schematically illustrates a specific embodiment of all the elements of the fixation device with a conducting tool.

FIG. 7 schematically illustrates a specific embodiment of all the elements of the fixation device 100 with a conducting tool 70 (e.g., a delivery catheter). Conducting tool 70 is adapted to keep distal and proximal anchors 10 and 20 in the FOLDED CONFIGURATION, and to facilitate the conduction of distal and proximal anchors 10 and 20 to the first and the second tissue locations (not shown) through an incision within the patient's skin.

In this figure, illustrated all the elements of fixation device 100: distal and proximal anchors 10 and 20, deployment tools 41 and 51, pushing rod 42, pulling suture 43, and elongated connecting element 30.

According to some embodiments, the repositioning of first and second tissue locations with respect to each other, is performed in the following method steps:
1. Inserting at least of the device to an incision;
2. Anchoring a distal anchor at a first desired tissue location;
3. Anchoring a proximal anchor threaded by a suture (in general—an elongated connecting element) at a second desired tissue location;
4. Pulling the suture through said anchor until a desired degree of tension is reached between the distal anchor and the proximal anchor; and,
5. Securing the proximal anchor to the suture by means of a suture lock (which may be part of tention varying means); thereby creating tension between a pairs of anchors and repositioning bodily tissues. By altering the tension—one can determine the esthetic outcome.

Once the proximal anchor is in place, the suture is pulled through the conducting tool until a desired tension in the suture between the two anchors is reached. This tension is preferably detected by means of a force or pressure meter attached to the proximal end of the suture, as will be clear by one skilled in the art. Alternatively, the desired tension will be visually noticed by the physician according to the esthetic result. As described above, the tension created on the tissues and in between the two anchors is highly important since it determines the esthetic outcome that will be obtained.

Once a desired tension between the proximal and the distal anchor is achieved via a tension varying means, the suture is affixed to the proximal anchor using locking means (or other tension varying means) that will be detailed in the following. This locking of the suture establishes a fixed tension between the anchor and its distal locked neighbor (the 'previous' anchor) that will not be affected by the possibly different tension imparted to other anchor pairs. The subsequent pair of anchors has its own tension. In this way the tension between any two successive anchors can be independently set. By this method an arbitrarily complex geometric remolding of subcutaneous tissue can be accomplished, the anchors being able to form web or network of points inter linked together The invention comprises a conducting tool and a set of linked anchoring elements. The conducting tool doubles as a magazine holding the anchoring elements. The anchoring elements are barbed devices adapted to be implanted in tissues of a patient and to be embedded therein. These elements are linked, for example by sutures or threads, along which the anchoring elements can slide until they are positioned in the patient's desired tissue location and then they are locked onto said tissue. By means of this locking action onto the tissues, a tension between each anchor element and its neighbors is created and can be independently fixed. A tension is also created on the tissues onto which the anchors are affixed.

The tubular part of the conduction tool of the invention is introduced under the skin surface. The introduction is preferably but not necessarily made just before the hairline, to conceal the point of entry. The distal end of the conducting tool is advanced under the skin surface to the targeted site.

FIGS. 8a-g schematically illustrate a specific embodiment of steps for the operation of fixation device 100 for anchoring distal and proximal anchors 10 and 20.

Figure 8A:
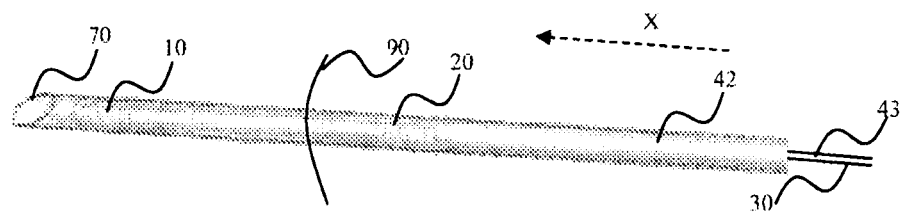
FIGS. 8a-g schematically illustrate the steps for the operation of the fixation device in the process of anchoring distal and proximal anchors.

Reference in now made to FIG. 8a which illustrates the initial position of fixation device 100. In this figure, all the elements are located within conducting tool 70 and on a rigid rod (not shown) which is adapted to provide an ability of the elements to slide over the same in a predetermined direction parallel to axis X. The rigid rod is also adapted to prevent distal and proximal anchors 10 and 20 to move to undesired locations before and during the process of anchoring. Elongated connecting element (e.g., suture) 30 passes through pushing rod 42, and proximal anchor 20, and is connected to distal anchor 10. Pulling suture 43 is connected to proximal anchor 20 and will be used for the deployed of the same.

At the first step, conducting tool 70 is moved through incision 90 into the patient's skin.

Figure 8B:
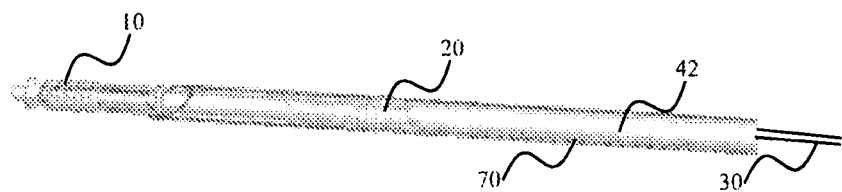

In FIG. 8b, distal anchor 10 is pushed by proximal anchor 20 which is pushed by pushing rod 42. During this process, conducting tool 70 is held by the operator, and elongated connecting element (e.g., suture) 30 which is connected to distal anchor 10, is moved together with proximal anchor 20 and pushing rod 42. It should be mentioned that, at this step, elongated connecting element (e.g., suture) 30 does not move with respect to proximal anchor 20 and pushing rod 42.

Figure 8C:
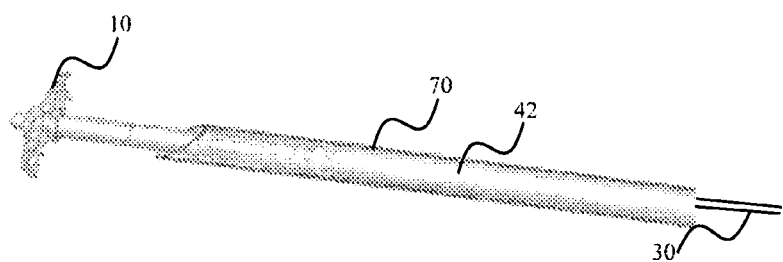

In FIG. 8c, illustrated the deployment of distal anchor 10. The deployment of distal anchor 10 may be performed in the two following ways (depends whether distal anchor should be moved from its initial location or not):
a. By pulling the elongated connecting element (e.g., suture) 30 while holding conducting tool 70 and pushing rod 42. As a result of that, elongated connecting element 30 which is connected to distal anchor 10, is adapted to cause the wings of distal anchor 10 to be reconfigures from the FOLDED CONFIGURATION to the DEPLOYED CONFIGURATION.
b. By holding elongated connecting element (e.g., suture) 30 and conducting tool 70, and at the same time, pushing the pushing rod 42. This will cause the wings of distal anchor 10 to be reconfigures from the FOLDED CONFIGURATION to the DEPLOYED CONFIGURATION.

Following the deployment of distal anchor 10, said anchor is anchored at a first tissue location (not shown).

Figure 8D:
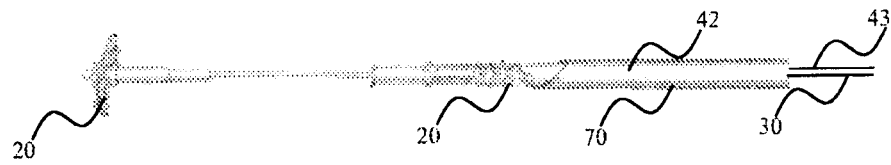

In FIG. 8d, conducting tool 70, pushing rod 42, and proximal anchor 20 with pulling suture 43 connected to it, are pulled back to the proximal direction, while distal anchor 10 is anchored, and elongated connecting element (e.g., suture) 30 is connected to it. An additional step which is performed is that conducting tool 70 is pulled with respect to proximal anchor 20, so that proximal anchor 20 is exposed out of conduction tool 70.

Figure 8E:
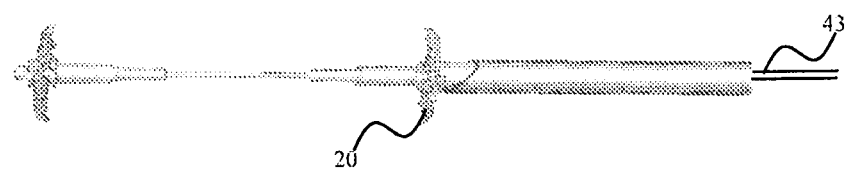

In FIG. 8e, proximal anchor 20 is deployed by a pulling force actuated on pulling suture 43, while holding all other elements, and preventing them to move. Following this step, proximal anchor 20 is anchored at the second tissue location (not shown).

Figure 8F:
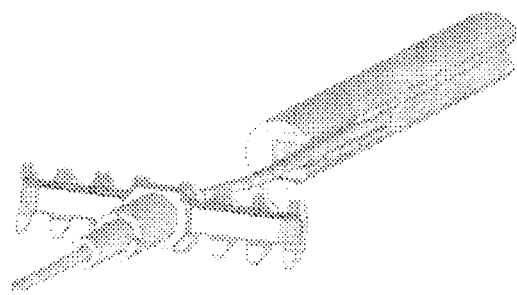
Figure 8G:
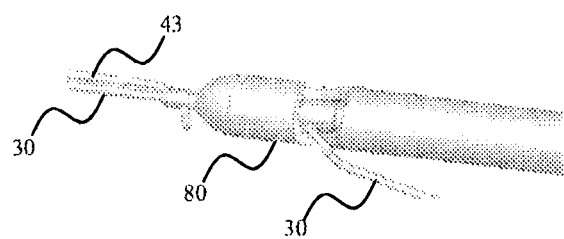

As illustrated in FIG. 8f, following the anchoring of distal and proximal anchors 10 and 20, as illustrated in FIGS. 8a-e, conducting tool 70 and pushing rod 42 are removed.

The final and the most important step of the anchoring method is generation of a predetermined tension between distal and proximal anchors 10 and 20. This final step is performed via tension varying means 80 connectable to distal and proximal anchors 10 and 20 through elongated connecting element 30 and pulling suture 43. Tension varying means 80 is adapted to alter parameters such as: the length of said elongated connecting element 30; and, the tension applied on elongated connecting element 30, such that first and second tissue locations (in which distal and proximal anchors are anchored) are repositioned with respect to each other according to these parameters.

According to a specific embodiment, tension varying means 80 performs its operation by pushing proximal anchor 20 and at the same time allowing elongated connecting element 30 and pulling suture 43 to pass through it. At the final step, when the predetermined tension between distal and proximal anchors 10 and 20 is achieved, elongated connecting element 30 and pulling suture 43 are secured to each other (e.g., via a securing knot), and the unneeded parts of them are removed (e.g. cut).

According to other embodiments, tension varying means 80 is adapted to alter the parameters by any other known in the art locking means adapted to affix (or secure) proximal anchor 20 to elongated connecting element 30.

It should be mentioned that fixation device 100 may comprise marks on it and on its elements, which are adapted to inform the operator how much the move the elements with respect to each other.

Once a pair of anchors is deployed and affixed to the first and second tissue locations, the tension which is created between said pair of anchors and the tissues, causes the skin to be in a stretched or compressed state, thus for example smoothing wrinkles, modifying the skin's surface appearance, repositioning tissues, fixing internal organs into particular locations, restricting internal lumen diameters, or the like. This may be accomplished by attaching the anchors to tissues surrounding internal organs, fascia, bones, etc. instead of attaching the anchors to skin tissue. By fixing a series of these anchors in place, complex webs of anchors, in which each pair of such anchors is characterized by tension which is independently set can be effected. The anchors can provide compression in some embodiments. The elongated connecting member connecting each anchor and its neighboring anchor can be pulled by the positioning of tension varying means or associated means to reach a desired level of tension between the two anchors. The tension created has high importance in determining the esthetic outcome.

Reference is now made to FIGS. 9a-9j which schematically illustrate a specific embodiment of a fixation device 200 of the present invention. The specific embodiment of the present invention illustrated in FIGS. 9a-j is a combination of fixation device 100 (from FIGS. 8a-8f) with a controlling mechanism 105, which is part of the deployment means disclosed above. In the light of that, the method step disclosed above, according to FIGS. 8a-f, are relevant for fixation device 200.

According to FIGS. 9a-j, controlling mechanism 105 is adapted to control the movement of the elements comprised in fixation device 100. For example, controlling mechanism 105 is adapted to move the following components: the elongated connecting member, the pushing rod, the pulling suture, etc.

Figure 9A:
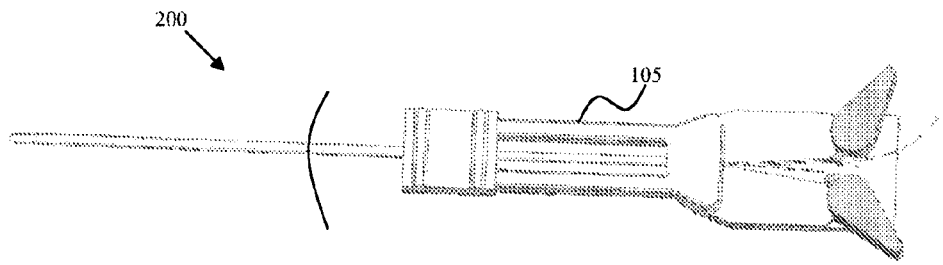
FIGS. 9a-9j schematically illustrate a specific embodiment of the fixation device of the present invention.
Figure 9B:
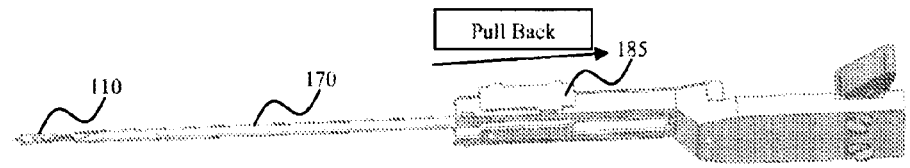
Figure 9B:
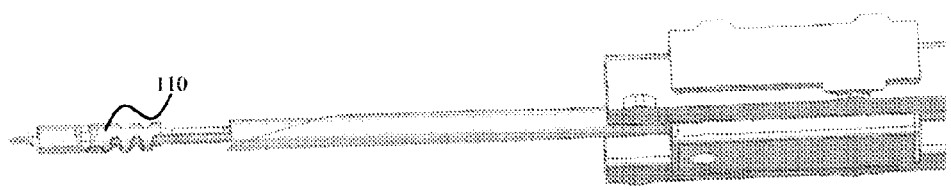

Reference is now made to FIG. 9b, which schematically illustrates the exposure of distal anchor 110 via a sliding block 185. As can be seen in this figure, sliding block 185 has at least two states: a first state in which distal anchor 10 is inside a conduction tool 170 (as illustrated in FIG. 9a); and, a second state in which distal anchor is ready for deployment (as illustrated in FIG. 9b).

Figure 9C:
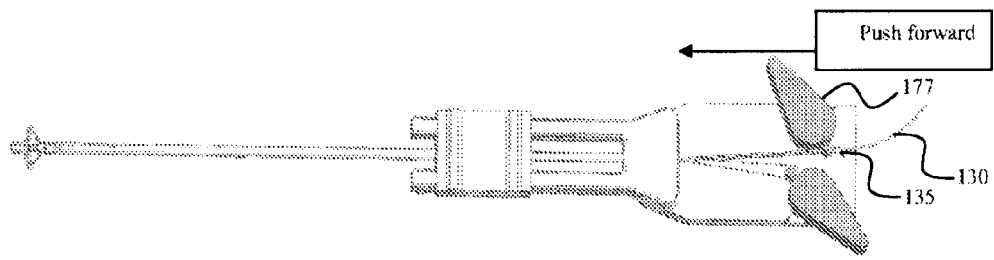

Reference is now made to FIG. 9c, which schematically illustrates the deployment of distal anchor 10 via a first deploy lever 177. First deploy lever 177 is configured to pull elongated connecting element (e.g., suture) 130, such that distal anchor 110 is deployed (similar FIG. 8c). The pulling of elongated connecting element (e.g., suture) 130 is performed by pushing forward first deploy lever 177 via a knot 135.

Figure 9D:
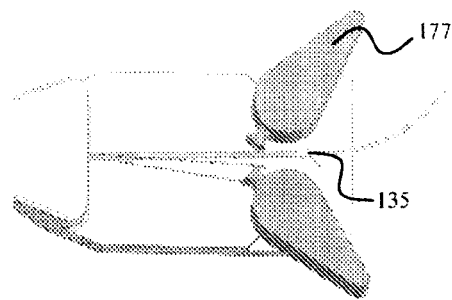

In FIG. 9d, first deploy lever 177 is pulled backwards to its initial state, while leaving distal anchor 110 in the DEPLOYED CONFIGURATION.

Figure 9E:
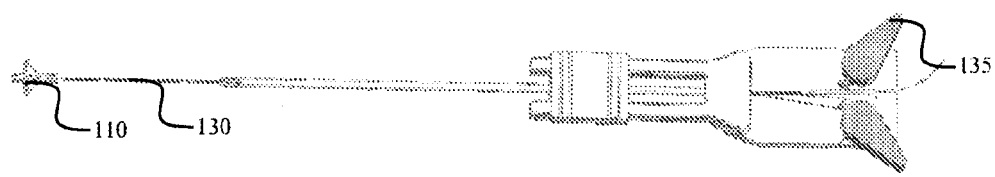

In FIG. 9e, sliding block 185 is pulled backwards in order to elongate the elongated connecting element (e.g., suture) 130 between distal anchor 110 and the proximal anchor (not shown). Proximal anchor 120 is exposed when sliding block 185 is moved backwards to its third position step in order to expose proximal anchor 120.

Figure 9F:
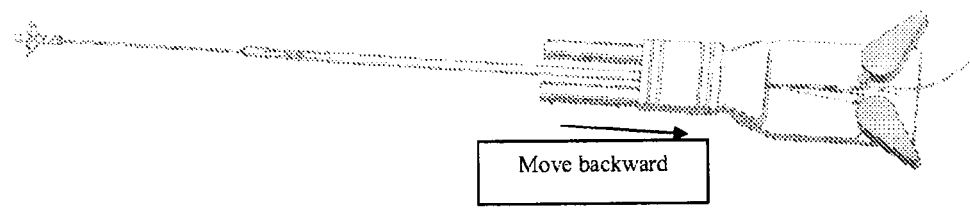
Figure 9F:
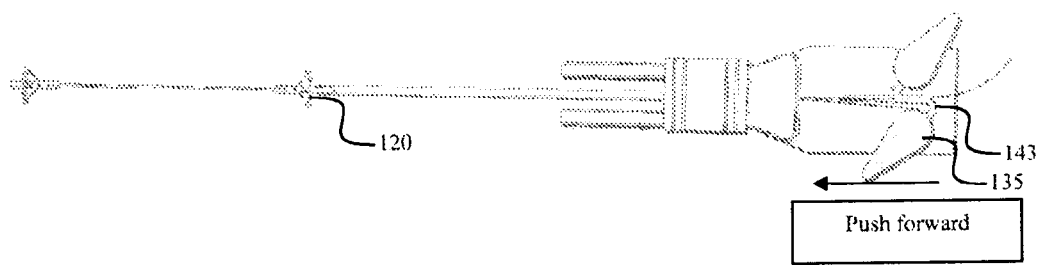

In FIG. 9f, a second deploy lever 177 is pushed forward in order to deploy proximal anchor 120 by actuating a pulling force of pulling suture 143.

Figure 9G:
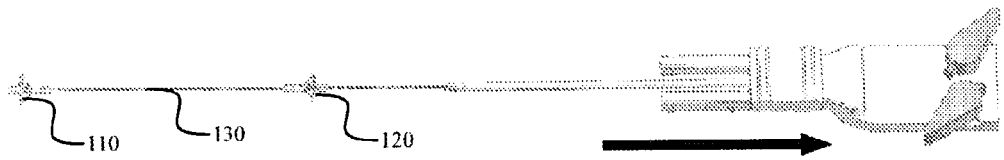

In FIG. 9g, pulling suture 143 is cut by the operator, and controlling mechanism 105 is removed. Following this step, the elements which are left are distal and proximal anchors 110 and 120, and elongated connecting element 130.

Figure 9H:
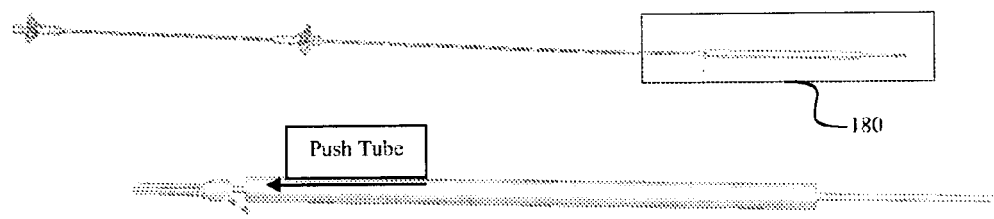
Figure 9I:
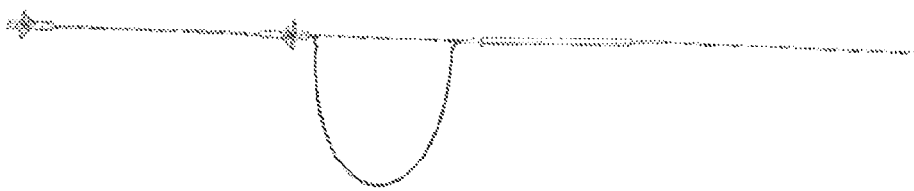
Figure 9J:
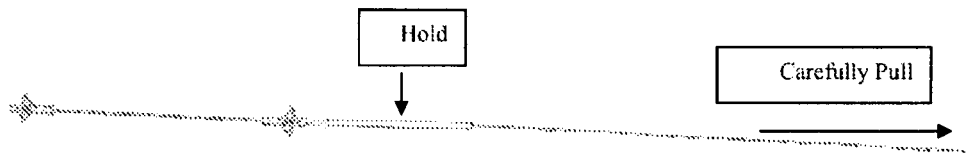

The following FIGS. 9h-j illustrate method steps for generating a predetermined tension between the distal and the proximal anchors, via tension varying means 180 (e.g. a tube with openings, etc.).

In FIGS. 9h-j illustrated how tension varying means 180 approaches proximal anchor 120 while elongated connecting element 130 passes within the same.

Following the creation of a predetermined tension within elongated connecting element 130 and between distal and proximal anchors 110 and 120, elongated connecting element 130 is secured to proximal anchor 120 (e.g., via a locking mechanism, via a knot, etc.), and tension varying means 180 is removed.

Figure 10A:
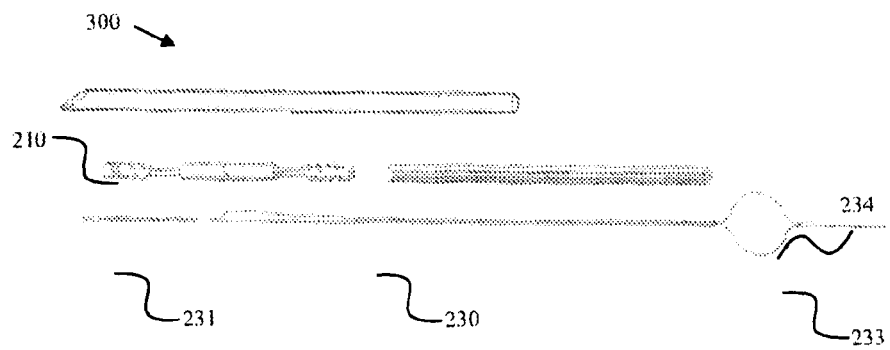
FIGS. 10a-10o schematically illustrate another embodiment of the present invention, and another method for performing the implantation according to the present invention.
Figure 10B:
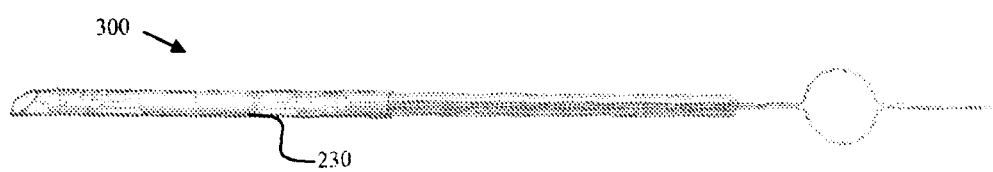
Figure 10C:
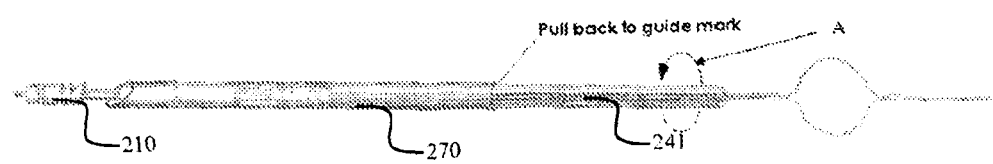
Figure 10D:
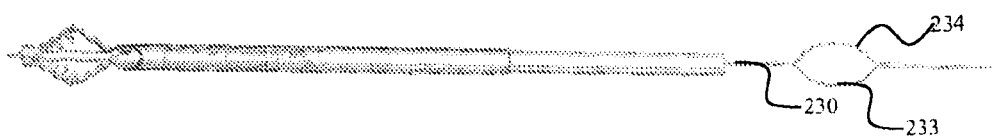
Figure 10E:
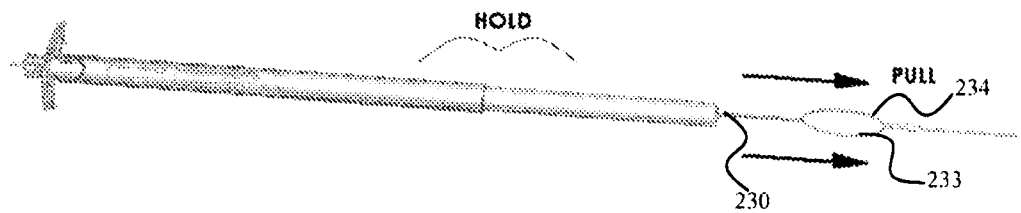
Figure 10F:
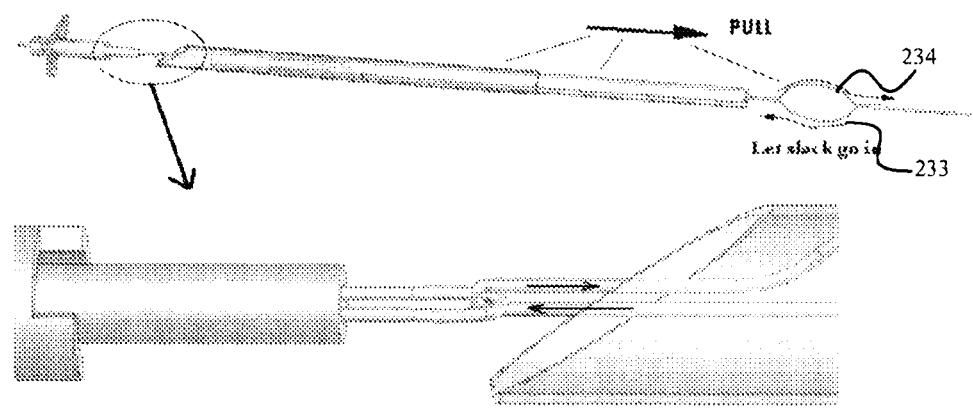
Figure 10G:
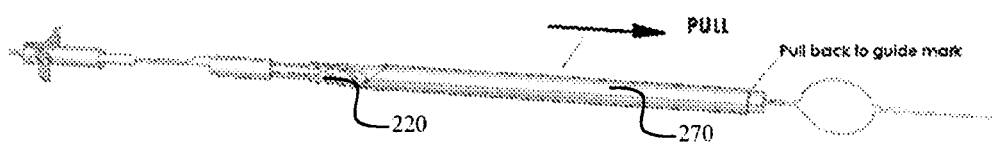
Figure 10H:
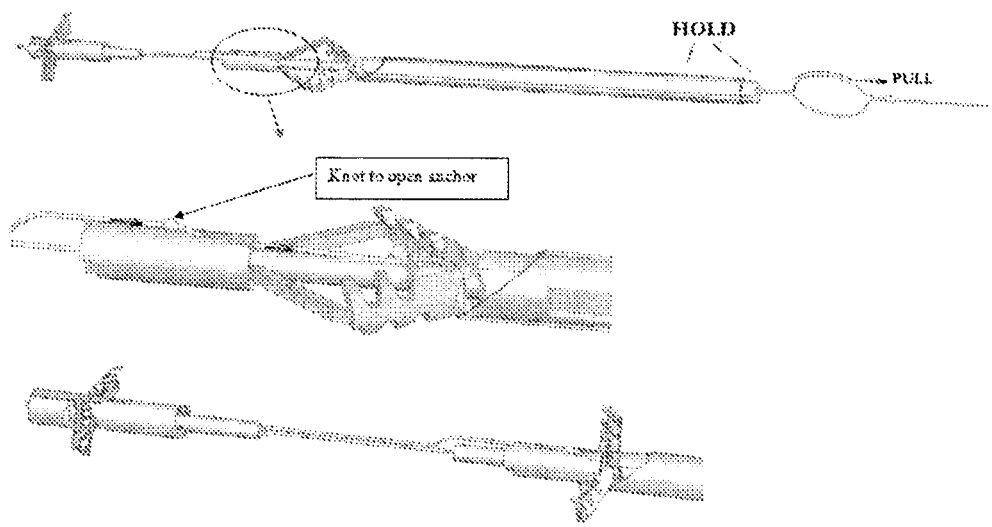
Figure 10I:
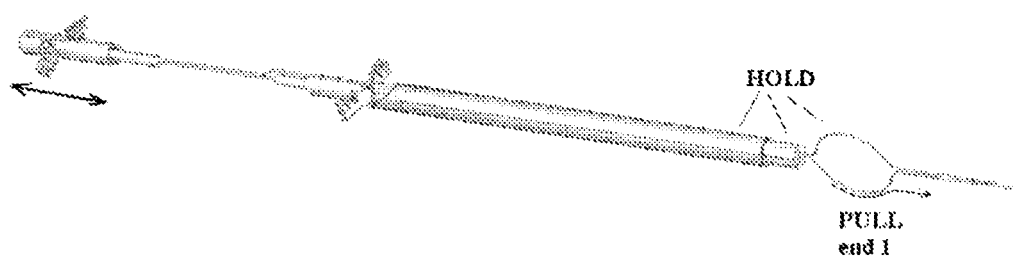
Figure 10J:
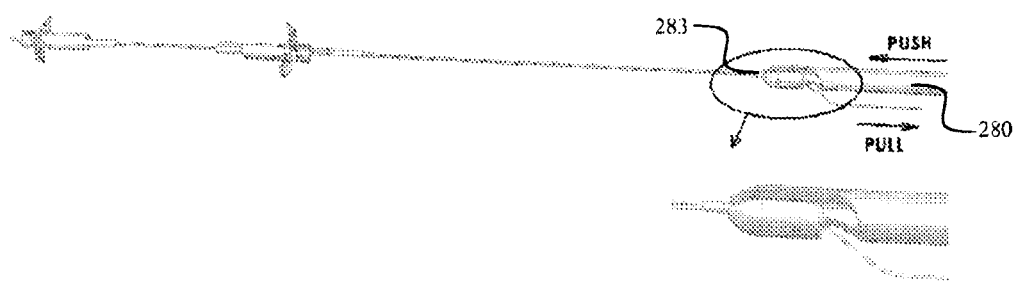
Figure 10K:
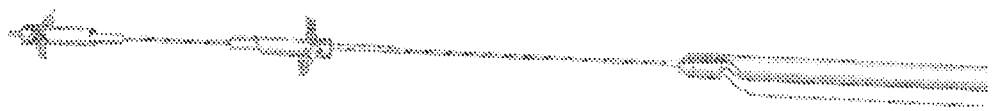
Figure 10L:
Figure 10M:
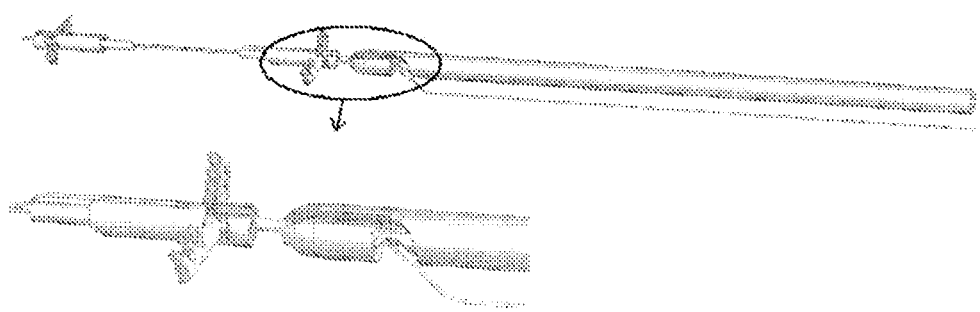
Figure 10N:
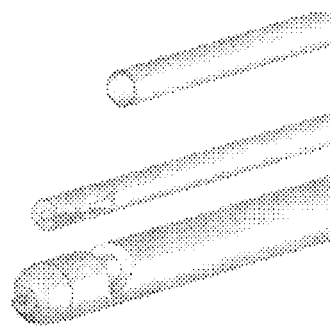
Figure 10O:
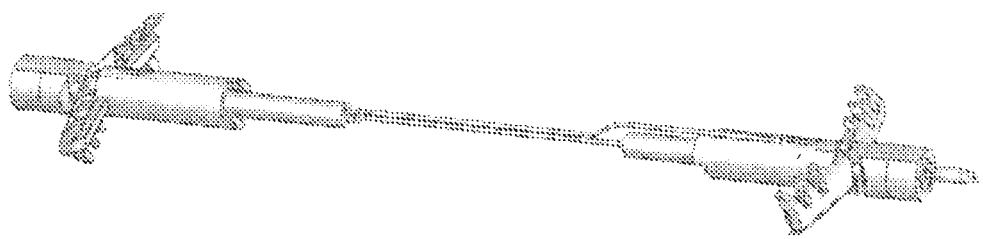

Reference is now made to FIGS. 10a-10o which illustrate another embodiment of the present invention, and another method for performing the implantation according to the present invention.

According to these figures, a fixation device 300 is illustrated. According to this embodiment, the elongated connecting element and the pulling suture are the same element. This change in the mechanical structure of fixation device 300 (relatively to fixation device 200), also changes the method steps for the operation of the device.

FIG. 10*a* illustrates the main elements of the fixation device 300. The difference between fixation device 100 and fixation device 300 is the structure of elongated connecting element 230, and the pulling suture 243, which are now unified. A new element which is added to this embodiment of the present invention is a holding suture 231 which is adapted to connect distal and anchor 210 to elongated connecting element 230. Elongated connecting element 230 has two ends: a first end 233; and a second end 234.

The entire system is shown in FIG. 10B.

Reference is now made to FIG. 10C. In order to extract distal anchor 210 out of the conducting tool 270, pushing rod 241 is held fixed, while the conducting tool 270 is pulled back.

The conducting tool 270 is pulled back to a guide mark located on pushing rod 241. Pushing rod 241 is also used to control the angular position of distal and proximal anchors 210 and 220 (marked in FIG. 10*c* as A).

Reference is now made to FIGS. 10*d* and 10*e* which illustrate the next step. Both first end 233 and second end 234 of elongated connecting element 230 are pulled in order to deploy distal anchor 210. In this step, pushing rod 241 and conducting tool 270 are held fixed.

Reference is now made to FIG. 10*f* which illustrates the next step. The end of conducting tool 270 is retracted to the position where proximal anchor 220 will be deployed whilst the conducting tool 270, pushing rod 241, and second suture end 244 are held in fixed position relative to one another. While these elements are being pulled back, first suture end 233 is allowed to move forward, and thereby lengthen the distance between distal and the proximal anchors 210 and 220.

Reference is now made to FIG. 10 *g* which illustrates the next step. At this step, both the pushing rod 241 and first and second suture ends 233 and 234 are held fixed. The conducting tool 270 is pulled back to second guide mark on the pushing rod. At this step proximal anchor 220 is exposed.

Reference is now made to FIG. 10*h* which illustrates the next step. The pushing rod 241 is held fixed while second suture end 234 is pulled to open the wings of the proximal anchor 220.

Reference is now made to FIG. 10*i* which illustrates the next step. First suture end 233 is pulled and relaxed to test aesthetic effect of the anchors. This is performed while the pushing rod and second suture end 234 are held fix.

Reference is now made to FIG. 10*j-o* which illustrate the next steps. According to these steps, after the pushing rod and the conducting tool are removed, tension varying means (e.g., a knot pusher) 280 is put over first suture end 233 behind a knot 283. According to another embodiment, the conducting tool is remained and only the push rod is removed.

Next (see FIGS. 10*k-36o*), using tension varying means (e.g., a knot pusher) 280, knot 283 is pushed down while first suture end 233 is pulled. Knot 283 is pushed until the aesthetic outcome is obtained by proper tension between the two anchors is achieved. In other words, knot 283 secures proximal anchor 220 to elongated connecting element and hence it eventually provides the desired aesthetic result. At final step illustrated in FIG. 10*o*, tension varying means (e.g., a knot pusher) 280 is removed and first and second suture ends 233 and 234 are trimmed off.

Furthermore, in this embodiment a step for testing the aesthetic effect is added.

Figure 11A:
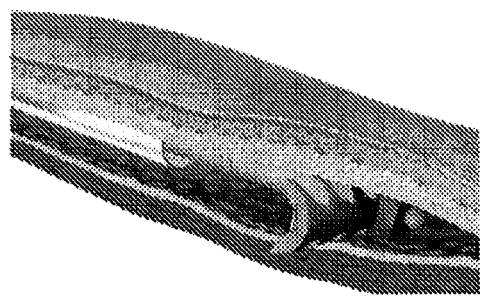
FIGS. 11a-c schematically illustrate the way an anchor is anchored at a predetermined tissue location.
Figure 11B:
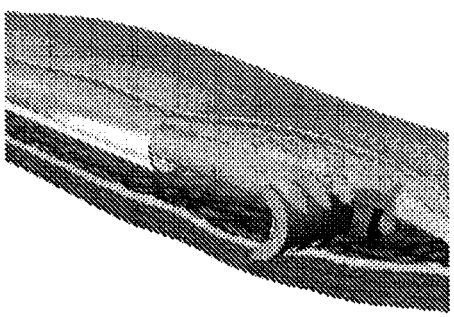
Figure 11C:
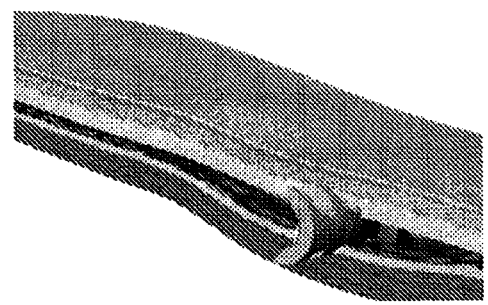

Reference is now made FIGS. 11*a-c* which schematically illustrate the way an anchor is anchored at a predetermined tissue location. According to these figures, since an anchor is characterized by prongs/spikes, by gently (if any) pressing on the tissue, it is anchored. The anchoring of an anchor may be between the dermis and the muscle.

It should be emphasized that according to another embodiment of the present invention, each of the above described embodiments and systems/devices can be incorporated with an elastic suture to provide elasticity to the device such that when said device is used on a facial tissues, facial expression could be obtained.

Figure 12:
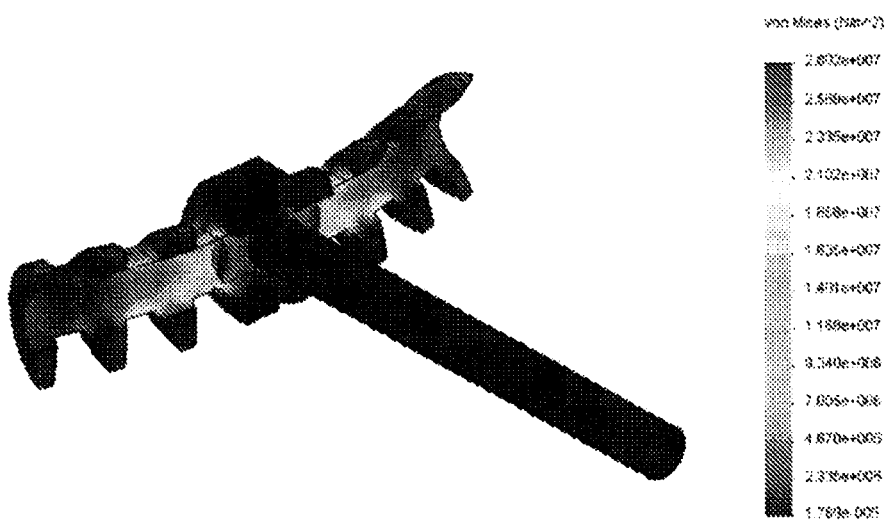
FIG. 12 is a finite element analysis of an anchor.

In FIG. 12 a finite element analysis of an anchor element (while being anchored) is shown. The rigid rod of the anchor is visible as is the stress field due to a 50 g load upon the device.

Figure 13A:
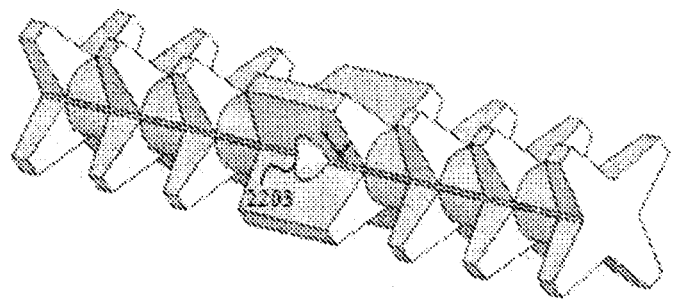
FIGS. 13a-b illustrate another embodiment of an anchor according to the present invention.
Figure 13B:
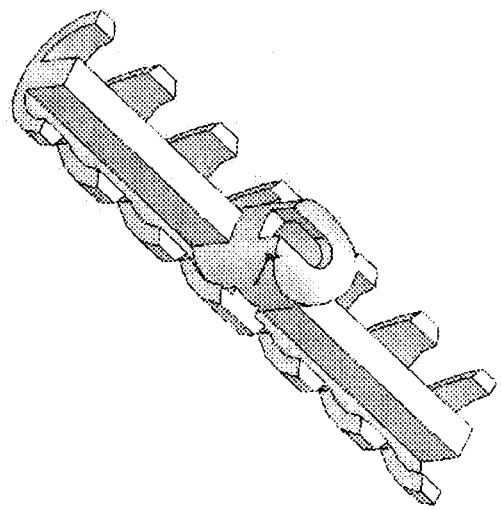

In FIGS. 13*a-b*, illustrated another embodiment of an anchor of the present invention. According to this embodiment, the distal and the proximal anchors are convertible from the FOLDED CONFIGURATION to the DEPLOYED CONFIGURATION by rotation of the same relatively to axis X (defined above).

Figure 14A:
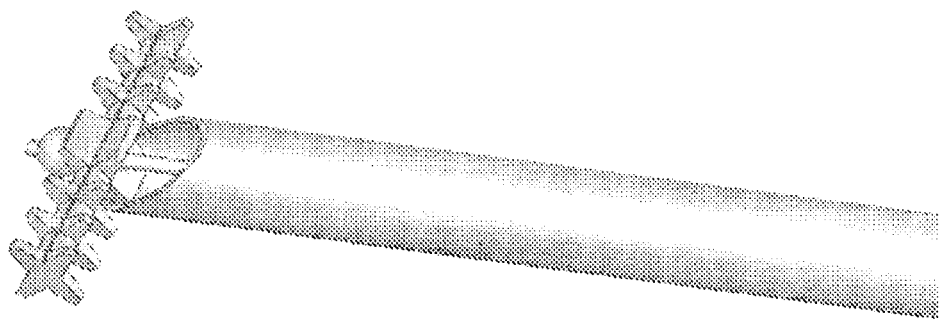
FIGS. 14a-b illustrate distal and proximal anchors which are rotatable.
Figure 14B:
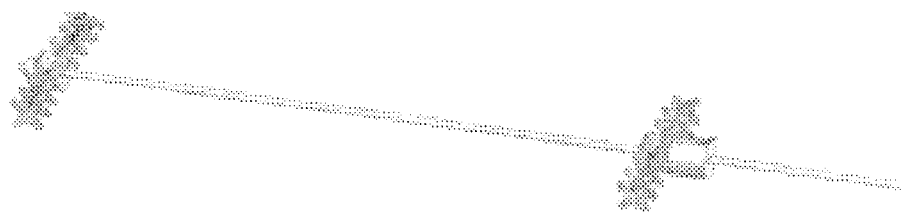

In FIGS. 14*a-b*, rotatable distal and proximal anchors 310 and 320 are illustrated.

In FIGS. 15*a-g* illustrated method steps for the operation of a fixation device 400 with rotatable anchors. Here a proximal anchor 2004, conducting tool 2000, incision 2008, pushing rod 2006, elongated connecting element 2003, distal anchor 2001, tension varying means 2009, and distal suture lock 2010 are visible. Several steps for using fixation device 400 are depicted. The objects to the left of the incision 2008 lie under one or more layers of skin and are seen as through the skin were transparent, while the objects to the right of the incision 2008 lie outside the body.

Figure 15A:
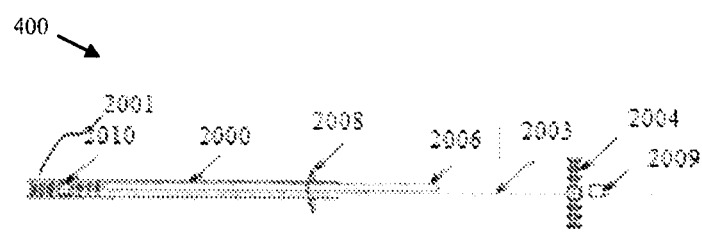
FIGS. 15a-g illustrate method steps for the operation of a fixation device with rotatable anchors.

In FIG. 15*a* the device is shown with conducting tool 2000 inserted into the incision 2008. The distal anchor 2001 is contained within the conducting tool 2000. The pushing rod 2006 is at the ready to deploy the distal anchor 2001.

Figure 15B:
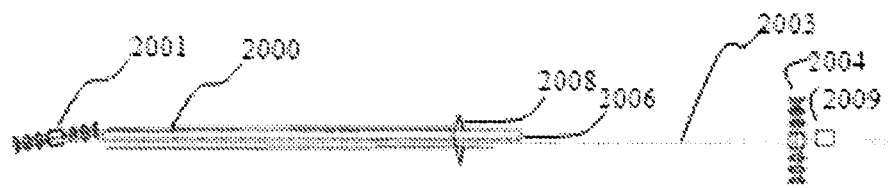

In FIG. 15*b* the distal anchor 2001 has been partially pushed out of the conducting tool 2000 by means of the pushing rod 2006.

Figure 15C:
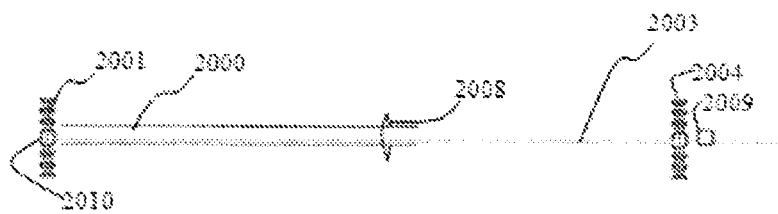

In FIG. 15*c* the distal anchor 2001 has been entirely pushed out of the conducting tool 2000 by means of the push rod 2006. It should be emphasized that the conducting tool 2000 is centralized with respect to the distal anchor 2001 and by that causes the distal anchor 2001 90 degrees rotation.

Figure 15D:
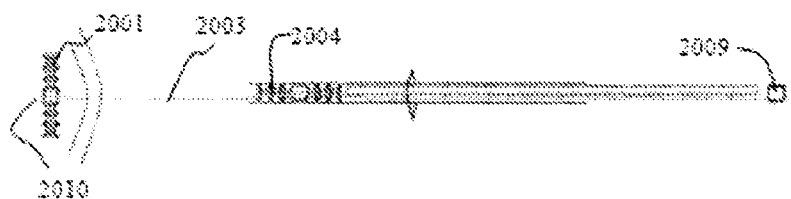

In FIG. 15*d* the distal anchor (which is pre-affixed to suture lock 2010) has been deployed and locked into a first tissue location on the elongated connecting element (e.g., suture) 2003 by means of suture lock 2010. Meanwhile the proximal anchor 2004 has been loaded into the conducting tool.

Figure 15E:
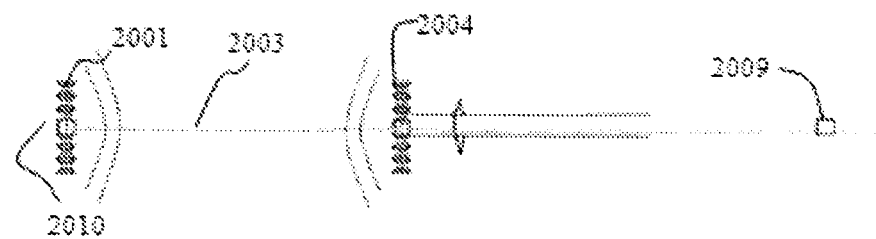

In FIG. 15*e* the proximal anchor 2004 has been deployed by means of the pushing rod which has subsequently been withdrawn.

It should be emphasized that the conducting tool 2000 is centralized with respect to the proximal anchor 2004 and by that causes the proximal anchor 2004 to cause 90 degrees rotation.

However the proximal anchor is not yet locked onto the suture. This will be accomplished in the next step.

Figure 15F:
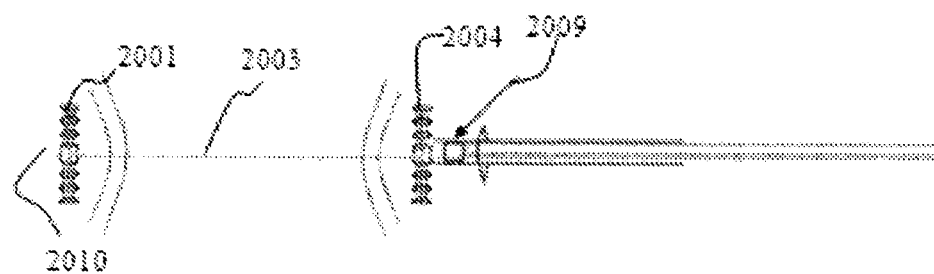

In FIG. 15*f* the tension varying means 2009 is pushed through the conducting tool by means of the push rod 2006 or any other especially dedicated tool. The elongated connecting element (e.g., suture) 2003 is pulled to the desired tension level between proximal and distal anchors, and the proximal anchor 2004 is now locked to the elongated connecting element (e.g., suture) 2003 by means of the tension varying means 2009.

Figure 15G:
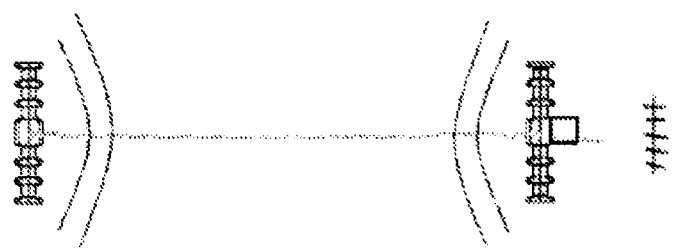

In FIG. 15g the incision is shown after being stitched closed.

Figure 16:
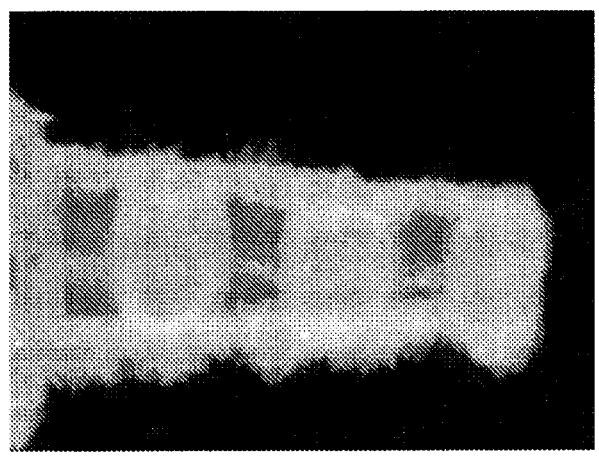
FIG. 16 illustrates a photo of an example prototype of the device.

In FIG. 16 illustrated a photo of an example prototype of the device. In this figure, a toothed anchor is illustrated. The anchor is a stereolithography apparatus. A stereolithography apparatus is a common rapid manufacturing and rapid prototyping technology for producing parts with high accuracy and good surface finish.

FIGS. 17a-c illustrate trials which were undertaken by using the device of the present invention in a chicken breast. The conducting tool 2300 is inserted into incision 2308. The distal anchor 2301 is implanted under the tissue and over the muscle, and is therefore visible only as a bump in the surface of the skin. As in actual surgery, the operator is shown pressing down upon the anchor to affix it into place.

In FIG. 17b the tension on the suture 2303 is being tested with a 200 gram load, which is measured using a load tester 2311.

In FIG. 17C the loaded anchor 2301 is shown in closeup, causing the skin to be pulled proximally towards the load tester.

It is within the scope of the present invention that the implantable medical devices be made of any ductile materials, such as stainless steel, plastic resins et cetera that are biocompatible and/or are coated with biocompatible materials, or materials typically used for producing stents or cogs typically providing for anchoring sutures. Materials capable of changing their elasticity or ductile properties by an internal molecular restructuring such as by externally heating them are applicable as well (e.g. shape memory materials). The implantable medical devices are attachable to the tissues of a patient due to their geometrical shape, their elasticity/ductile, and/or optional spikes or cogs extending from their surfaces. Optionally the implantable medical devices are coated with suitable chemicals or drugs, such as botulinum toxin, antibiotic agents and/or growth factors, prior to their disposal within a patient tissue.

The implantable medical devices can be prepared form a variety of biocompatible materials which can serve as either a constructive material or as a coating layer, or as components of a composite. These biocompatible materials may include the following types: polymers (which may be bioabsorbable, durable, synthetic, or naturally derived), metals (and different metals alloys), and ceramics. The polymer can be selected from a group consisting durable polymers, both synthetic and natural occurring materials including polyethylene, polypropylene, polyurethanes, poly (methyl methacrylate), polycarbonates, silicone rubber, biodegradable polymers, synthetic and natural occurring materials including polyalkylene esters, polylactic acid and its co-polymers, polyvinyl esters, polyvinyl alcohol, polyanhydrides, and polycarbonates, shape memory polymers, Polyglycolic acid and its co-polymers.

The implantable medical devices can be prepared from metals such as stainless steel, CoCr, titanium, shape memory alloys, hydroxyapaptite, bioactive glass, alumina, zirconia, and others that will be apparent to those skilled in the art. Materials capable of changing their elasticity/ductile properties by an internal molecular restructuring such as by externally heating them are applicable as well.

The implantable medical devices can be prepared with bioactive coatings such as proteins, growth factors, antigens, carbon-like diamond, carbon, hyaluronic acid, collagen, silver, gold, and others known to those skilled in the art. Optionally the implantable medical devices can be coated with suitable chemicals or drugs, such as botulinum toxin, antibiotic agents and/or growth factors, prior to their disposal within a patient tissue.

It should be emphasized that the anchors can be anchored into place in the body simply by applying pressure from outside the skin upon the anchoring means. The pressure can be applied for example by the surgeon pressing down upon the anchor. Alternatively, the anchors, once spread out are affixed to the tissue without any external pressure.

According to another embodiment the surgical operations possible using the devices described above include cosmetic surgeries; remolding and/or reconstructing both soft and/or hard tissues; repairing tears, holes, or apertures in soft biological tissue; organ repositioning and/or reconstruction; wrinkle removal; face lifting; intensive and/or immediate care for repairing ruptures of blood vessels, skin, or other tissue; repair of lacerations; orthopedic surgeries; dental surgeries; soft and hard tissue reattachment; and others that will be obvious to one skilled in the art.

According to some embodiments, the conducting tool used in the present invention is preferably diagonal (oval-like) or made rounded. The conducting tool's tip can be formulated in 90 degrees, or made at an angle of less than 90 degrees. According to one embodiment, the conducting tool additionally comprises an additional element which is used to create the path for the anchors. The main advantage of this element is the reduction in the chances of damaging nerves or blood vassals.

Load Capability

The factors that influence the load capability are:
1. The subcutaneous tissue (between the bottom layer of the skin and above the muscle) and its strength/density/integrity will affect the grip between the spikes on the wings of the anchor and the tissue. Also how well the device is positioned in the proper location within the skin-muscle structure will impact this load transfer.
2. The height of the spikes number of spikes and width of the wings of the anchor.
3. The bending strength of the wings of the anchor and hinge section prior to buckling.
4. The grip power between the tension element and the sliding gripper on the proximal wing device.

The elongated connecting element, which according to some embodiments is a suture, preferably provided with some degree of elasticity and bioabsorbability. In one embodiment of the invention, the elasticity is such that 10% elongation is provided at a load of 120 grams. The suture may be composed of suitable material such as those known in the art, including Ethibond (Ethicon, Somerville, N.J.), No. 2 Fiberwire (Arthrex, Naples, Fla.), SMC 7 (Glycoprene II), surgical gut, dexon (polyglycolic acid), chromic suture material, and possibly non-absorbable sutures such as nylon or prolene.

According to another embodiment, the suture has no elasticity at all.

In a preferred embodiment of the device, the anchor elements are implanted from 3 cm to 12 cm apart.

In another embodiment of the invention, the implants may be removed after implantation.

In one particular embodiment, the device is inserted through a micro-incision in the temporal region above the hairline.

The anchors of the device are preferably inserted under the bottom layer of skin, just above the topmost muscle layer.

According to another embodiment, the anchors of the device are inserted under the muscle layers.

It has been estimated that an estimated tension of 120 grams of tension is necessary in the suture connecting two anchoring elements.

The method of surgery and operation of the device are relatively easy to learn. The procedure is physically easy to perform, and is in fact possible with use of one hand, if desired, leaving the surgeon's other hand free.

It is estimated that the procedure is quite rapid, requiring less than ten minutes for performing the entire procedure (i.e., performing an incision, embedding the distal anchor, the proximal anchor, reaching the desired tension, locking the proximal anchor and closing the incision).

The introducer of the device can be prepared as a sterilized, one-use disposable device.

The implant will generally be about 9 mm at its widest point, although variations from about 0.1 mm to about 10 cm are technically possible and in some cases may prove beneficial.

It is within provision of one embodiment of the invention that the anchors and/or sutures may be comprised of biodegradable material, with the expectation that fibrosis buildup around these components will eventually replace the degrading materials.

In one embodiment of the device, the thread, tension element, or suture connecting anchoring elements of the device is smooth and not barbed, to prevent damage to tissue insofar as possible.

In a preferred embodiment of the device, the tension between neighboring anchoring elements of the device is individually adjustable.

In one embodiment of the device, the tension element is transparent such that it will not be visible through translucent areas of skin.

In one embodiment of the invention the tension elements are removable.

In the preferred embodiment of the invention, the anchoring elements have multiple points of contact with the surrounding tissue, to better distribute the mechanical load caused by the tension of the neighboring tension elements pulling on the anchor.

In most embodiment of the invention, the anchors are not fixed to bone or fascia, but in certain embodiments such attachment may prove beneficial.

By careful selection of the materials involved, discomfort caused by the devices can be ameliorated by changing the degree of plasticity of the elements and their rate of biodegradation. Similarly, the duration of results can be controlled to be about 2-3 years, while the degradation of the device materials themselves will occur over a period of about 9 to about 12 months or less.

In a preferred embodiment of the device, the conducting tool creates its own path between the bottom-most layer of skin and topmost layer of muscle.

In one embodiment of the device the outside diameter of the conducting tool is about 2.3 mm, although it is possible that devices with smaller and larger diameters may be found beneficial.

In certain embodiments of the design, a sliding knot as utilized in endoscopic surgery may be employed to lock the elongated connecting element to the proximal anchor. Such sliding and locking knots are well known in the art. Knots such as the Roeder knot, Tayside knot, Weston knot, preformed loop, Nicky's knot, SMC knot, Tennessee slider, Duncan loop, surgeon's knot may be found appropriate for use with the invention.

In such embodiments, two "tails" of suture from the proximal anchor are used, a first that creates the tension between anchors and a second that is used to open the wings of the anchor. A sliding knot such as the "Roeder's knot" may be used to maintain tension between the two anchors. Then the knot can be slid down towards the proximal anchor to secure and maintain the tension in between the two anchors. The tension is maintained in order to provide the desired esthetic outcome. This proves to be a highly reliable method for securing the suture tension.

In other embodiments of the invention, one may employ a method of melting the suture into a small ball of bioabsorbable material using a small electrical resistance wire. Also, simple friction devices can be utilized.

EXAMPLES

Examples are given in order to prove the embodiments claimed in the present invention. The example, which is a clinical test, describes the manner and process of the present invention and set forth the best mode contemplated by the inventors for carrying out the invention, but are not to be construed as limiting the invention.

Example 1

1.1 Overview, Background, and Purpose

Surgical correction of facial asymmetry or deformity is a commonly performed reconstructive procedure. Nevertheless, following facial trauma and repair with open reduction and internal fixation techniques, the soft tissue may be weakened and often falls as a result of gravity, resulting in facial asymmetries. This loss of support by soft tissues or ptosis, is also observed in patients with cranial nerve VII dysfunction, as in Bell's palsy, neoplasm or trauma patients, and in patients undergoing extirpative procedures for cancer. Therefore, facial ptosis appears in various clinical scenarios where loss of facial mimetic tone, either through facial nerve dysfunction or facial nerve sacrifice, prevents the skin and soft tissues from remaining in their correct anatomical position. In the setting of facial nerve dysfunction, this is most commonly demonstrated by inadequate eye closure and oral commissure incompetence. Loss of tissue support and ptosis is also observed in the aging population and interventions to ameliorate quality of life have become an increasing need.

Many different surgical techniques such as sutures, grafts and facial reanimation are available to correct these deformities. However, it is necessary to select the appropriate surgical procedure that will provide the optimal results for each individual patient and each facial area (i.e.: forehead, eyebrow, eyelids, midface, etc) and reduce the need for further corrective procedures on these patients. For example, the direct brow lift, though effective in correcting the ptosis, often results in noticeable scars and damage to the supraorbital nerve, which may lead to paraesthesiae or numbness over the forehead region. The endoscopic brow suspension technique can avoid the visible scar but requires greater technical expertise, specialized endoscopic equipment, increased operating room time, and decreased suspension durability and symmetry. Suture techniques have proved useful. However, sutures often pull out or suture material becomes infected, requiring a repeated surgery. Botulinum toxin injection, an easy, non-invasive technique, has also been tried in this setting but with a limited success and unpredictable results. Therefore, there is a clear need for new methods or devices to address this broad clinical need of soft tissue lifting.

The present invention is a device for soft tissue lifting that can overcome many of the drawbacks of existing techniques. As such, the device can be quickly introduced in the desired area through a minimally invasive procedure, in an outpatient setting and with a minimal recovery period. The device is made of FDA-approved biocompatible, biodegradable material and has strong anchoring points to prevent release and movement. Furthermore, at the time of introduction the position and degree of lift can be readjusted to ensure symmetric results.

1.2 Objectives

To demonstrate substantial equivalence of performance, safety, degradation and efficacy for the JUVENCE device as compared to the commercially-available Silhouette®, Endotine® devices and non-absorbable polypropylene control devices.

1.3 Study Endpoints

1. Stretching measurements of the ear implants at implant, post-op days 1-3, then at least once a week (beginning post-op day 4) until termination via Indian Ink tattoos.
2. Clinical observations post-op days 1-3, then at least once a week (beginning post-op day 4) until termination including, but not limited to:
3. Behavior
4. Skin condition, including incisions
5. Respiration
6. Recumbence
7. Body Weight, recorded prior to implant and weekly until termination
8. Device weights prior to implant and at termination
9. Histopathology 2 Test System 2.1 Species Selection Species/Strain: Swine/Yucatan
Weight/Age: 80-120 kg/Age specific to weight
Number/Sex: 3/Female Porcine skin is very similar to human skin, and this study seeks to evaluate a subdermal device. Porcine skin is widely used in wound healing studies and should serve as a close approximation to human skin. In addition, the Yucatan swine growth rate is much slower than Yorkshire-cross swine, therefore not altering the implant sites throughout the 12-week survival period.

2.2 Animal Health Requirements

All animals were verified to be in good health by a research facility veterinarian via physical exam. All animals were received and conditioned per The Integra Group SOPs.

Any animal showing signs of disease, which may affect the outcome of the study, were excluded from the study according to The Integra Group SOPs.

2.3 Number

The study was completed with a total of three (3) swine 2.4 Identification

Upon receipt each study animal had a unique alphanumeric identification assigned by the Integra Group per Integra Group SOP. This unique study designation is traceable to a unique vendor ear tattoo/ear tag on each animal. All records and specimens pertaining to each animal refer to this unique designation.

2.5 Housing

Animals were housed and quarantined from other study animals for a minimum of three days prior to entering into the study. All animals were housed in accordance with criteria outlined in the "Guide for the Care and Use of Laboratory Animals" (National Academy Press, 1996), including but not limited to space, illumination, noise, temperature and humidity recommendations. Animals were provided food and water ad libitum except prior to any anesthetized procedure. Housing for all animals was per Integra Group large animal housing SOP (30-026).

2.6 Feed and Water

Feed and water were provided as per Integra Group SOP (30-026).

2.7 Handling and Care

Animal health and behavioral observations were noted in animal records and veterinary observation form. Handling and care were per Integra Group large animal handling SOP (30-026).

2.8 Source

Animals were acquired from the test facility approved animal supplier:
Sinclair Research
PO Box 658
Columbia Mo. 65205

3 Test and Control Articles 3.1 Test Article
Juvence Device (Aesthetics Point)
3.2 Control Articles
Silhouette Device (Silhouette-Lift)
Endotine Device (Coapt Systems)
Polypropylene Juvence Device (Aesthetics Point)
3.3 Test and Control Article handling by the testing facility Test article handling was per the Integra Group SOP (30-036). Briefly, test articles arrived with documentation of size and type of article.

4 General Study Administration 4.1 Scheduling of Procedures

Detailed scheduling of the procedures was coordinated by Integra Group staff and sponsor and depended upon facility, staff and procedural list availability.

4.2 Test Material Location and Handling

Test materials and samples were provided by the study sponsor before the procedure and were stored in a secure area at the test facility according to Integra SOP's.

4.3 Location of Study Records and Tissues

During the course of the study all raw data related to the study is stored in the study file located in a secure area of the testing facility. After the completion of the final report (signature and date of Study Director) the original raw data, original protocol, original final report will be transferred to the Sponsor for GLP retention requirements and copies of the original data will be retained by the Integra Group for twenty years.

During the course of the study the fixed tissues were also retained in a secured location at the testing facility and will be transferred to the Sponsor (or designee at the sponsor's request) for storage after completion of the study.

5 Good Laboratory Practice Compliance

This study was not conducted in accordance with FDA Regulations on Good Laboratory Practices (GLP) for Non-clinical Laboratory Studies CFR Title 21 Part 58. It was conducted under applicable Integra Group Standard Operating Procedures (SOP). All study data were recorded and protocol deviations and amendments were documented.

6 Study Design

This was a prospective, non-randomized, controlled, and intent to treat study.

Three Sinclair Yucatan Mini-swine weighing 99-107 kg were entered into the study once verified healthy by the attending veterinarian. All three animals had a bilateral subdermal implants placed on the ear pinnae (auricular surface) and cervical neck (base) areas (12 implants). Animal Weights, photographs and measurements were obtained of the skin above the implants on the surgery day and at least weekly thereafter. After 12 weeks of implantation the animals were euthanized and the implants removed en bloc and preserved with 10% buffered formalin solution. After fixation, a sample of the implant and surrounding tissue was cut and stained for histological reading. The retrievable portions of the device were salvaged for degradation analysis by weight.

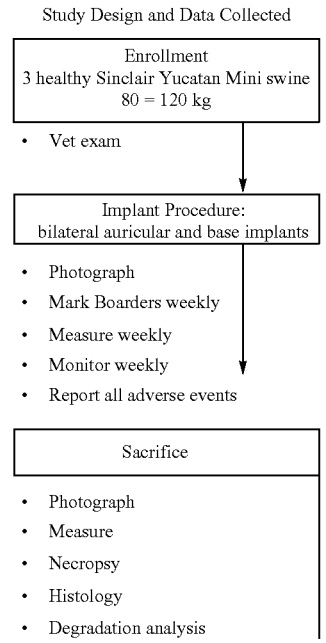

Study Design and Data Collected 6.1 Control of Bias

This study compared to control devices implanted in the same test animals: the Silhouette Device (Silhouette-Lift), the Endotine Device (Coapt Systems) and a non-absorbable polypropylene Juvence Device (Aesthetics Point)

7 Study Procedures 7.1 Acclimation

An acclimation period of a minimum of three days was provided for the animals prior to study activity per Integra group SOP (30-028).

7.2 Pre-Procedure Fast

Solid food was withheld for approximately 12-36 hours, prior to any anesthetized procedure.

7.3 Preoperative Medications

No preoperative medications were given for this study.

7.4 Skin Preparation

The right and left axillary regions were shaved, as well as the dorsal surfaces of the ears and neck. These areas were then draped with a sterile surgical drape or towels.

7.5 Anesthesia

Animals were sedated by IM injection (Telazol, 2-8 mg/kg or to effect and/or Buprenorphine, 0.01 mg/kg or to effect). If further anesthetized by IV injection (Propofol, 2-6 mg/kg or to effect), doses were recorded. Atropine (0.04 mg/kg) IM was given to control mucosal secretions.

An endotracheal tube was placed to ensure proper ventilation.

Eye lubricant was applied to maintain moisture throughout the procedure.

The animals were secured to the table in the dorsally recumbent position for primary access to the right and left axillary regions.

IV fluids were administered as needed to correct pressures and volumes of the animal.

A pulse oximeter, temperature probe and ECG leads were placed for periprocedural animal monitoring.

Anesthesia effects were monitored throughout the procedure via ECG, pulse oximeter, blood pressure, respiration, palpebral response, jaw tone, and/or response to other stimuli.

Mechanical ventilation was initiated (approximately 12-16 breaths/min, adjusted as needed) and maintained throughout the procedure.

7.6 Animal Monitoring During Procedure

Physiologic monitoring equipment including an ECG monitor, temperature monitor, and a pulse oximeter were placed for periprocedural monitoring.

7.7 Body Heat Maintenance during Procedure

A heating pad was placed under each animal to assist in maintaining body temperature during the procedure.

7.8 Periprocedural Medications

Additional medications and the dose administered during the study were documented on the Animal Procedure Medication and Anesthesia Record.

7.9 Implant Procedure

The animals were kept under general anesthesia (inhalation isoflorane) through an endotracheal tube.

An approximately 5 mm incision was made on the dorsal side of the base of the ear, using a scalpel blade. Each device was inserted through the incision to the subcutaneous layer, 6 cm away from the insertion point (or more, to allow noticeable stretching). The distal anchor was released and anchored to the muscle layer and to the skin. Then, the introducer was retracted and the same procedure repeated for the proximal anchor. After both anchors of the device were secured in place, the connecting thread was shortened to a degree of noticeable stretching to cause a ruffled compression of the skin between the anchors but without causing damage to the tissue.

The same procedure was performed on both ears and at the cervical ear base, bilaterally.

Figure 17:
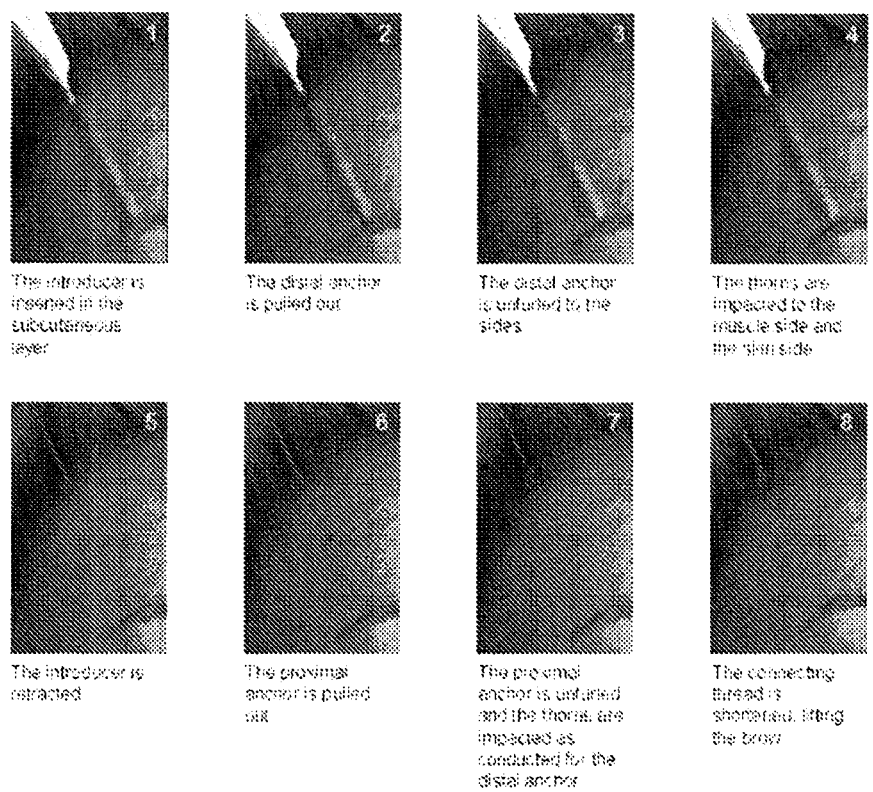
FIG. 17 illustrates the device of the present invention in the experiments of Example 1.
Figure 18A:
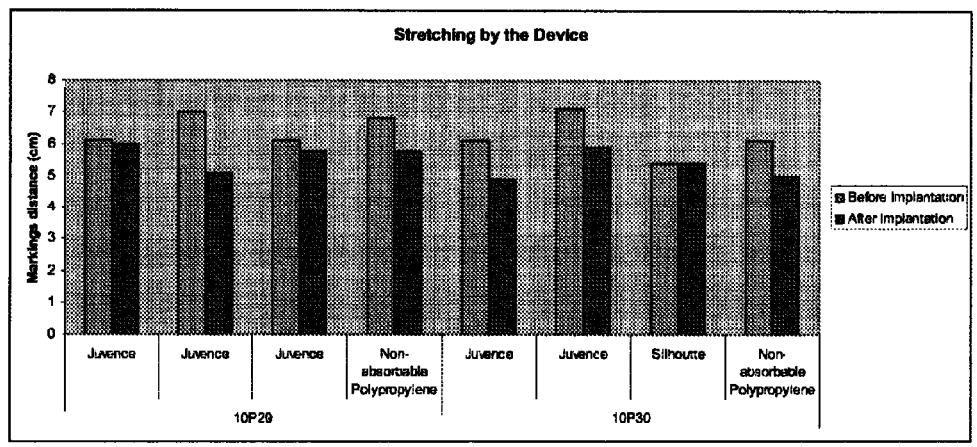
FIGS. 18a-d illustrates graphs according to the result of the experiments of Example 1.
Figure 18B:
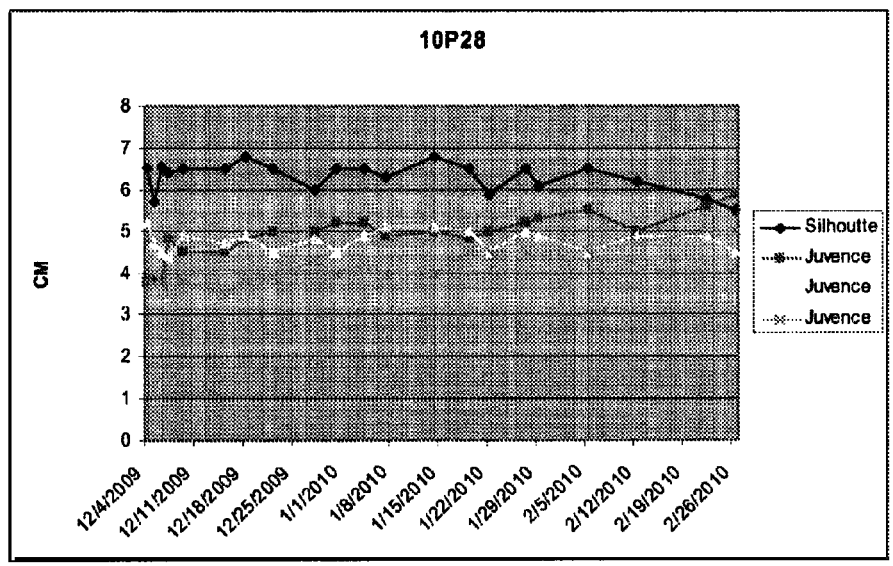
Figure 18C:
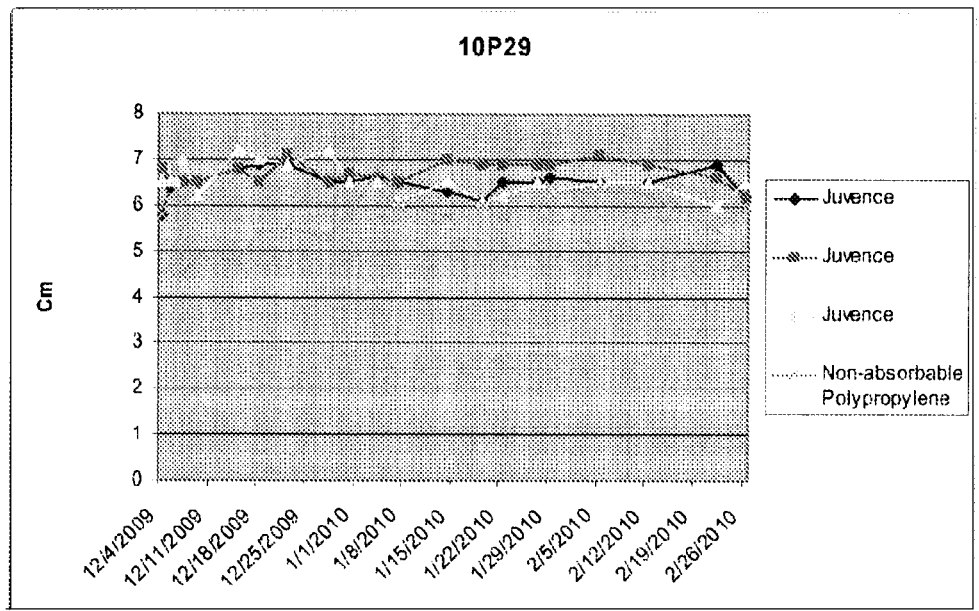
Figure 18D:
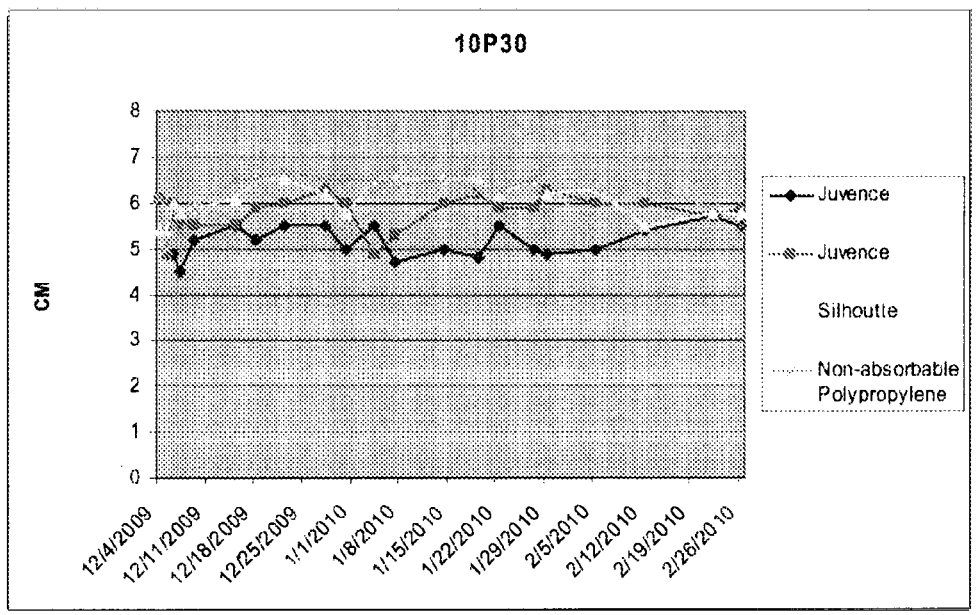

The device insertion procedure is described in FIG. 17. Juvence device implantation was performed or supervised by an experienced veterinary surgeon in the same manner as planned for clinical use. Control devices were inserted according to their established current clinical procedure. The origins and insertion of all implants were marked by tattoo at implant and weekly by Sharpie indelible markers.

7.10 Postoperative Care

The animals received analgesia medication (buprenorphine, 0.01 mg/kg SQ/IM) in the immediate post procedural period. Additional analgesic medication could be administered at the discretion of a testing facility veterinarian.

If the animals received postoperative antibiotic therapy (cephalexin or equivalent, 250-500 mg, Oral) at the discretion of a testing facility veterinarian, administered doses were recorded.

7.11 Daily Observations

Clinical observations including measurement of the implant origin and insertion of the implant was performed for the first three (3) days after implantation and then at least once a week until study termination. Particular attention will be directed to behavior, skin, respiratory and recumbence. Any abnormal findings were recorded and reported to the study director. There were no abnormalities.

If an animal showed severe abnormalities or signs of suffering following implantation, it could be humanely sacrificed in order to reduce pain and suffering, at the discretion of the study director and after informing the sponsor. This did not occur in this study.

At least weekly after implantation, each animal was anesthetized with 4-6 mg/kg Telazol and the implants careful measured, palpated and photographed.

7.12 Euthanasia

Following completion of a 12-week survival period, the animals were heparinized ($300u$/kg IV—allowed to circulate for at least 3 minutes), then humanely euthanized with an IV overdose of a barbiturate-based euthanasia solution (Beuthanasia-D or equivalent).

The implant sites were then grossly examined.

7.13 Pathology

A limited necropsy was performed by a testing facility veterinarian. This involved a description of the implants, photographs and an en block removal of the devices and surrounding tissues. After fixation in 10% Buffered Neutral formalin, a section of the implant and surrounding tissue was removed and fixed for histological evaluation.

7.14 Histology

Collected tissues were processed at a minimum as Hematoxolin and Eosin (H and E) histology slides. Processing was performed by:
Twin Cities Histology
4129 85th Ave N
Brooklyn Park, Minn. 55443

8 Changes in Conduct of the Study 8.1 Protocol Amendments

There were two amendments to this study:

Amendment 1 modified the procedures and objectives based on experiences learned during the implantation procedure on Jan. 22, 2010.

Amendment 2 modified the study objectives to clarify that safety and degradation would be assessed on Mar. 26, 2010

8.2 Protocol Deviations

Biweekly ear measurements were discontinued because it was determined that ear, head and neck movements could vary the measurement length by 25% or more. The animals were sedated and head and ears placed consistently for measurements and this could only be done once weekly for humane reasons.

One of the silhouette devices (implanted in 10P30) was successfully implanted but failed to stretch. Post-surgical analysis was still performed on the implantation sites of both devices.

Although passively implanted, neither of the two Endotine devices were explanted for analysis.

8.3 Exclusions

There were no animals excluded from this study.

8.4 Deviations Due to Animal Condition or Disease

There were no deviations due to animal condition or disease.

9 Results

The following results summarize the findings of all test animals throughout the duration of this study.

9.1 Test Animal Demographics 9.2 Daily Observations

Animals were observed daily by animal care staff. Any abnormal observations were recorded in the daily observation form. No abnormalities were reported in daily observations for any animal in this study.

9.3 Implant Measurements Raw Data FIGS. 24 and 25 show implant measurements raw data.

9.4 Implant Measurements Trends

Measurements of the distance between the palpatable device ends were performed at least once a week. Initially, tattoos were placed at each end to mark the general implant sites. These tattoos were completely invisible within 3 weeks. Indelible Sharpee markers were utilized at least weekly to mark the edges and this worked quite well. The markings needed to be refreshed at least weekly because the skin completely sloughed these markings within 1 week. As the study progressed, the compressions (i.e. the wave-like ruffle pattern in the skin caused by the implantations) reduced and became impossible to visualize. Stretching was maintained.

Generally, the animals were anesthetized to make the measurements of the implant ends. This was required because the implants needed to be palpated to find the ends. Implants in the neck or ears that extended beyond the base were difficult to interpret because positioning of the head or ears could influence the distance measurements by up to 1 cm difference. The anesthetized animals were positioned in the same way each time to allow palpation and minimize measurement variation. In addition, ear palpation was much easier and so may provide for a preferred implant site.

FIGS. 18a-d illustrate the measurements for all animals in which the device was implanted during the implantation procedure.

Due to the difficult interpretation of measurements, there is a large variance in the recorded measurements making the distance measurement stability inconclusive. Indeed, this can be seen most dramatically in the failed Silhouette device (10P30). A summary of the distance measurement stability is provided in table:

TABLE 1

Animal Demographics

| Total Days Implanted | Necropsy Date Necropsy Weight | Implant Date Weight at Implantation | Date of Birth Age at Implantation | Sex Species/ Breed | Animal |
|---|---|---|---|---|---|
| 90 days | Feb. 24, 2010 100.0 | Dec. 3, 2009 100.5 | Sep. 23, 2003 7 years | Female Swine Yukatan | 10P28 |
| 90 days | Feb. 24, 2010 103.0 | Dec. 3, 2009 106.5 | Mar. 5, 2004 6 years | Female Swine Yukatan | 10P29 |
| 90 days | Feb. 24, 2010 110 | Dec. 3, 2009 103 | Jul. 18, 2006 4 years | Female Swine Yukatan | 10P30 |
| | 82 kg | 81 kg | 2 years, 2 months | Ovine/ Suffolk | |

TABLE 2

Skin Measurements

| Recorded Length Over Time | Implant | Site | Animal |
|---|---|---|---|
| Lengthened slightly | Juvence | Right ear | 10P28 |
| flat | Juvence | Right Base | 10P28 |
| flat | Silhouette | Left ear | 10P28 |
| flat | Juvence | Left Base | 10P28 |
| flat | Juvence | Right ear base | 10P29 |
| Lengthened | Polypropylene | Right ear | 10P29 |
| flat | Juvence | Left ear | 10P29 |

TABLE 2-continued

Skin Measurements

| Recorded Length Over Time | Implant | Site | Animal |
|---|---|---|---|
| flat | Juvence | Left Base | 10P29 |
| flat | Juvence | Right ear | 10P30 |
| flat | Polypropylene | Right Base | 10P30 |
| flat | Juvence | Left ear | 10P30 |
| flat | Silhouette | Left Base | 10P30 |

9.5 Weekly Weights

All study animals were weighed at least weekly. All animal weights were stable in this study.

TABLE 3

Animal Weights

| 10P30 | 10P29 | 10P28 | Date |
|---|---|---|---|
| 100.5 Kg | 106.5 Kg | 99.5 kg | Nov. 23, 2009 |
| 104 | 104.5 | 102.5 | Dec. 23, 2009 |
| 105 | 99.5 | 100.5 | Dec. 30, 2009 |
| 108 | 103.0 | 104.5 | Jan. 6, 2010 |
| 108 | 102.0 | 102.5 | Jan. 13, 2010 |
| 107.5 | 101.0 | 105 | Jan. 20, 2010 |
| 108.5 | 101.0 | 102 | Jan. 27, 2010 |
| 108 | 101.0 | 102 | Feb. 3, 2010 |
| 107.5 | 100.5 | 102 | Feb. 10, 2010 |
| 108 | 100.5 | 100.5 | Feb. 17, 2010 |
| 110 | 103 | 100 | Feb. 24, 2010 |

9.6 Implant Photographs

Figure 19A:
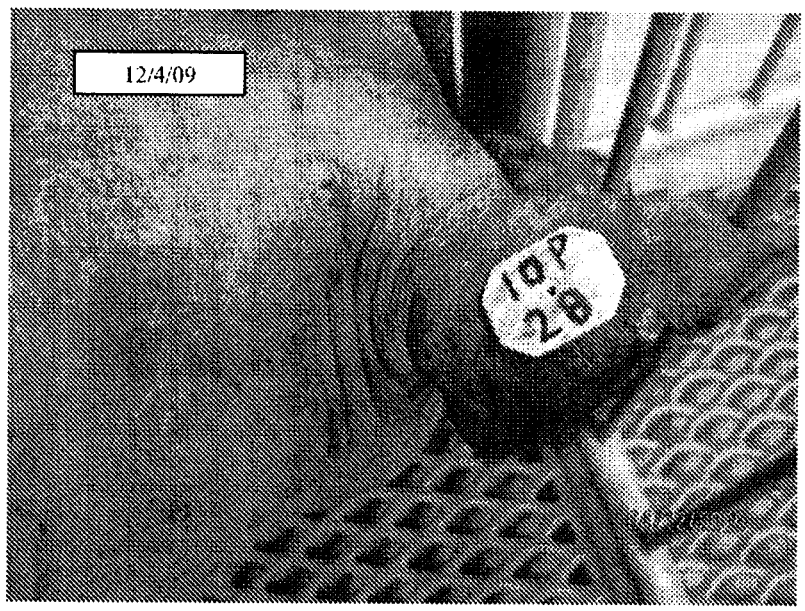
FIGS. 19a-o. illustrate photographs of pigs according to the experiments of Example 1.
Figure 19B:
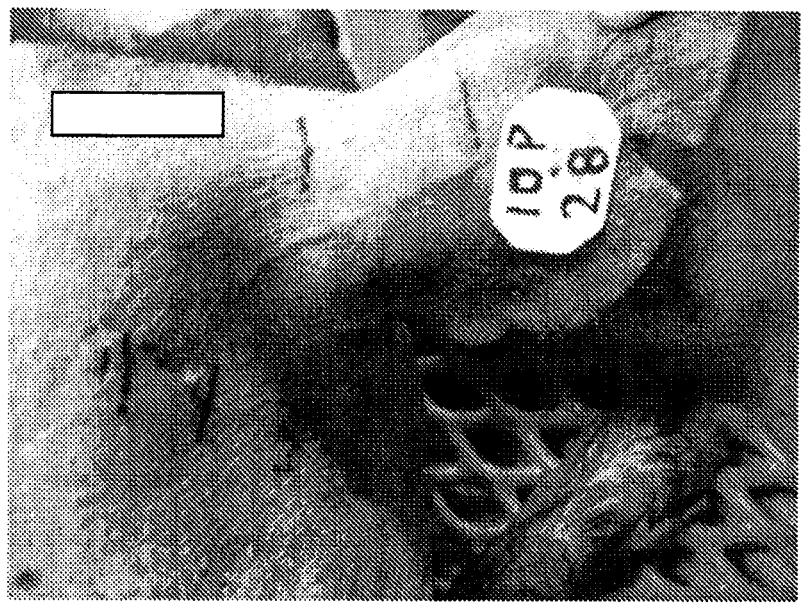
Figure 19C:
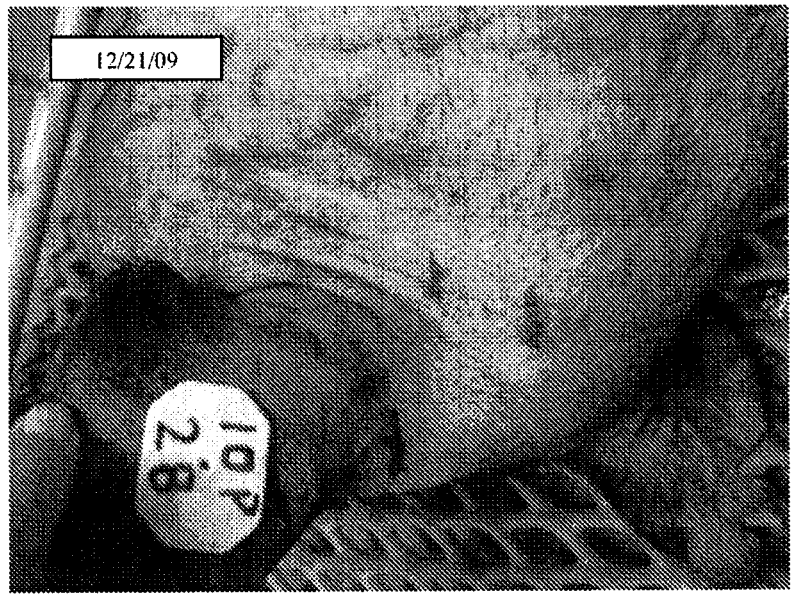
Figure 19D:
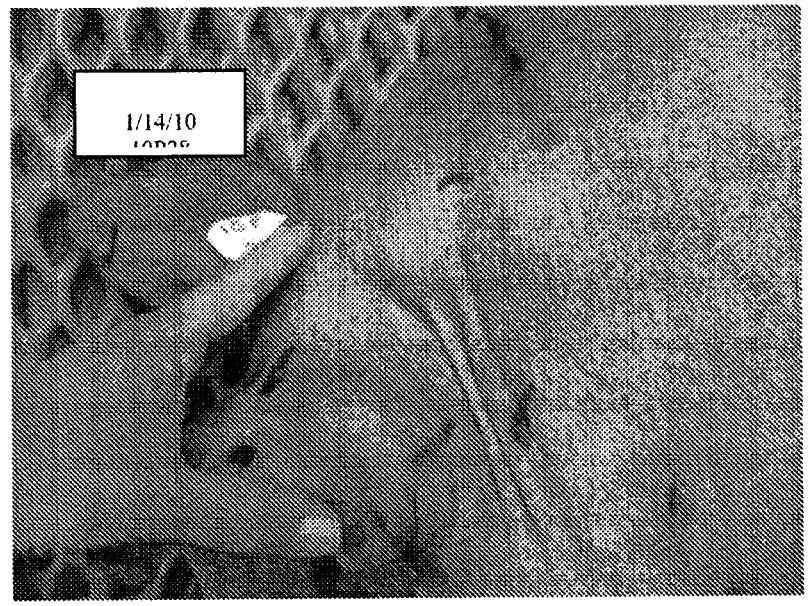
Figure 19E:
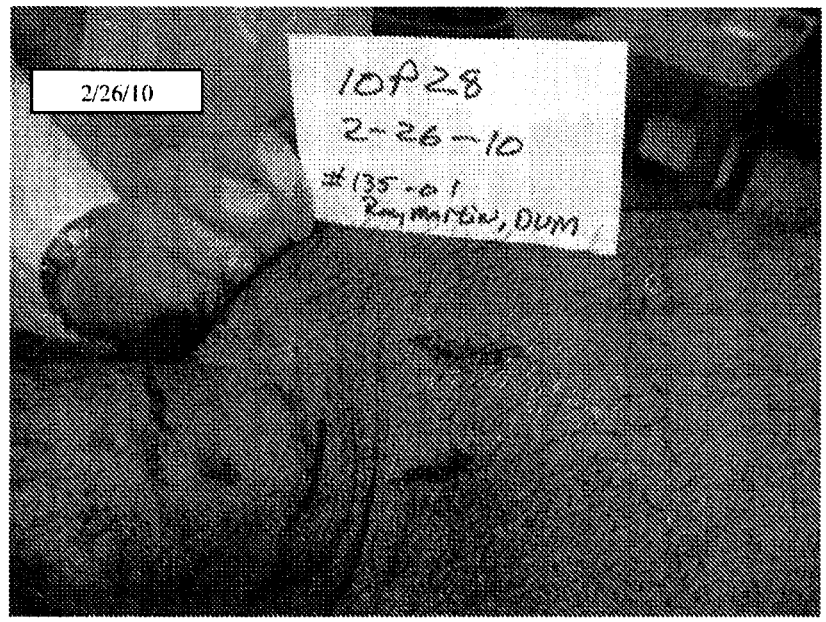
Figure 19F:
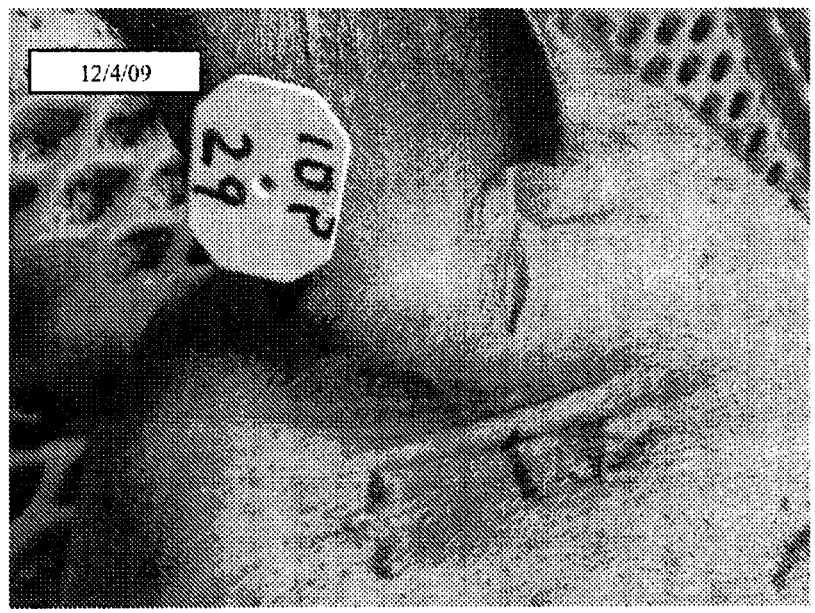
Figure 19G:
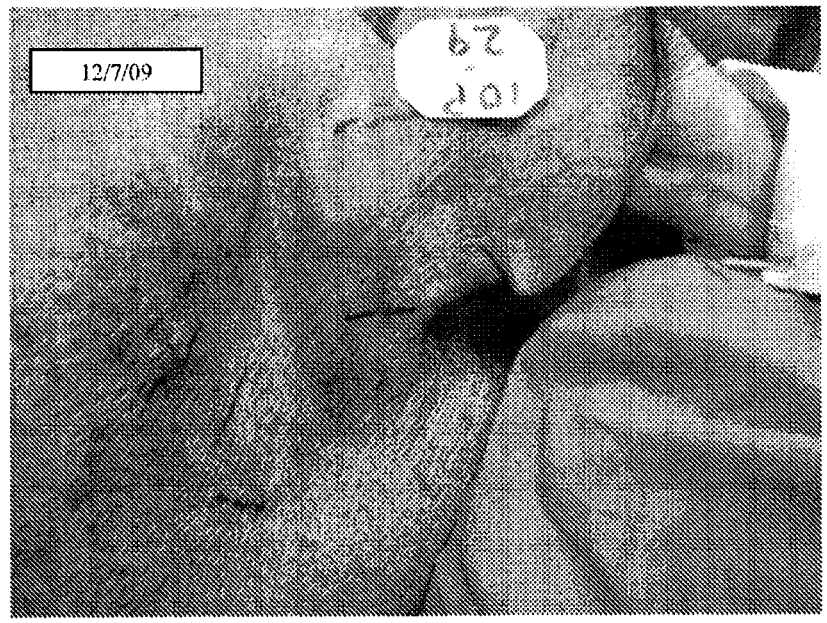
Figure 19H:
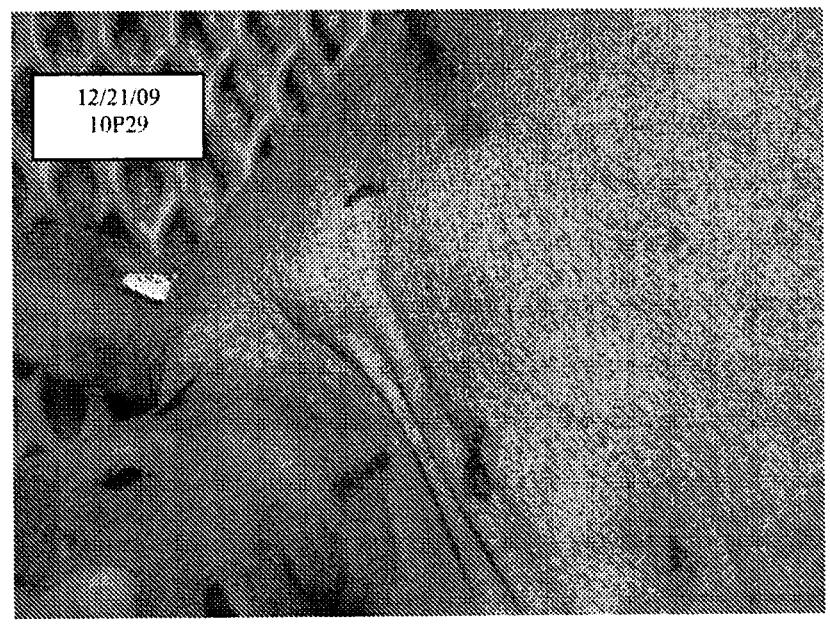
Figure 19I:
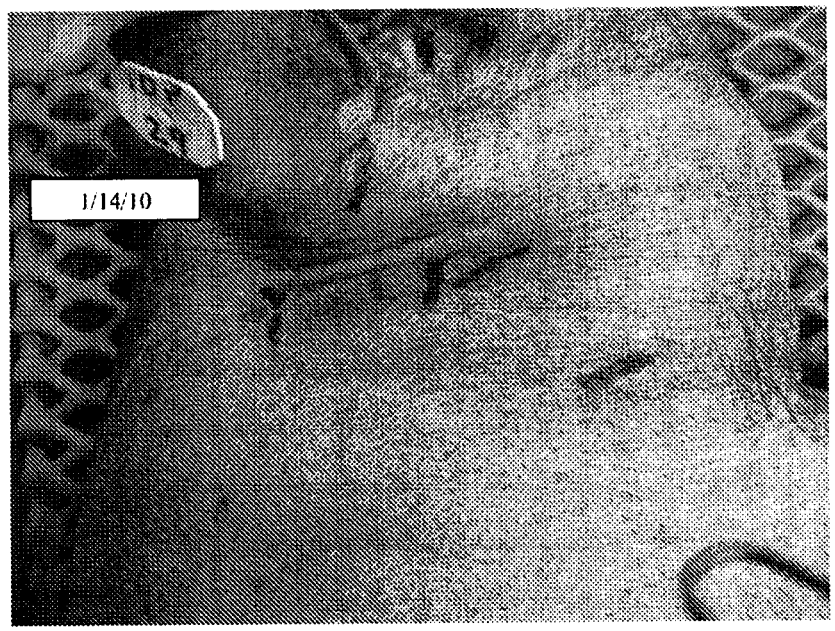
Figure 19J:
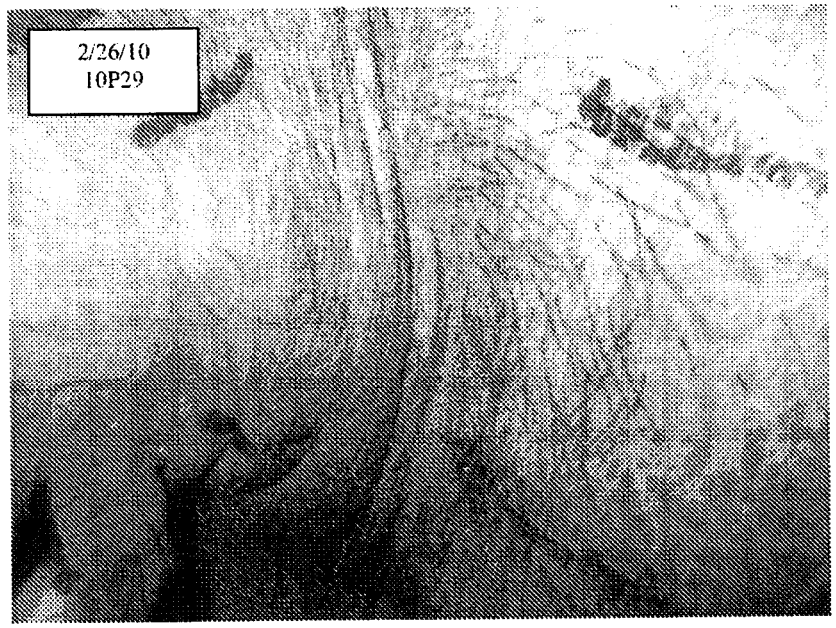
Figure 19K:
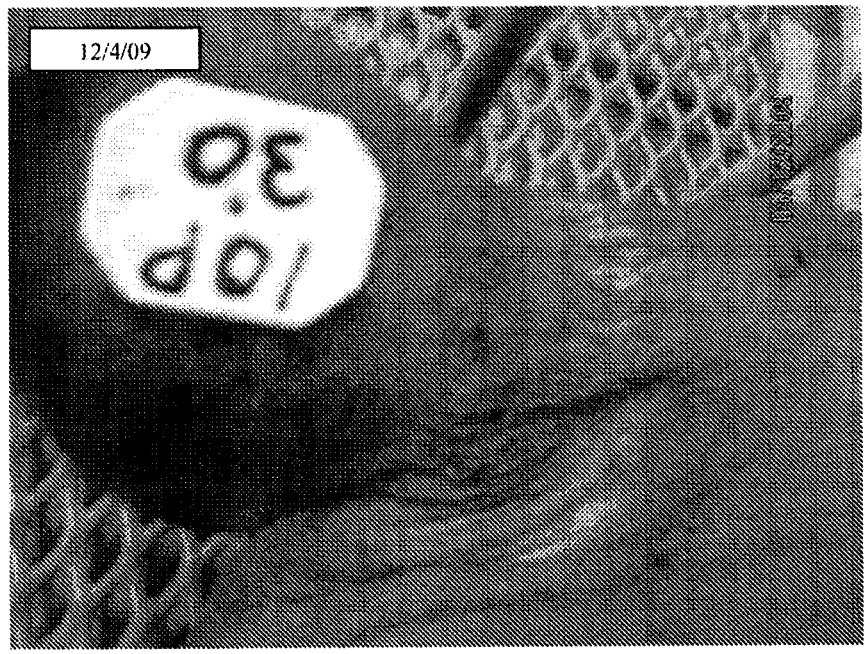
Figure 19L:
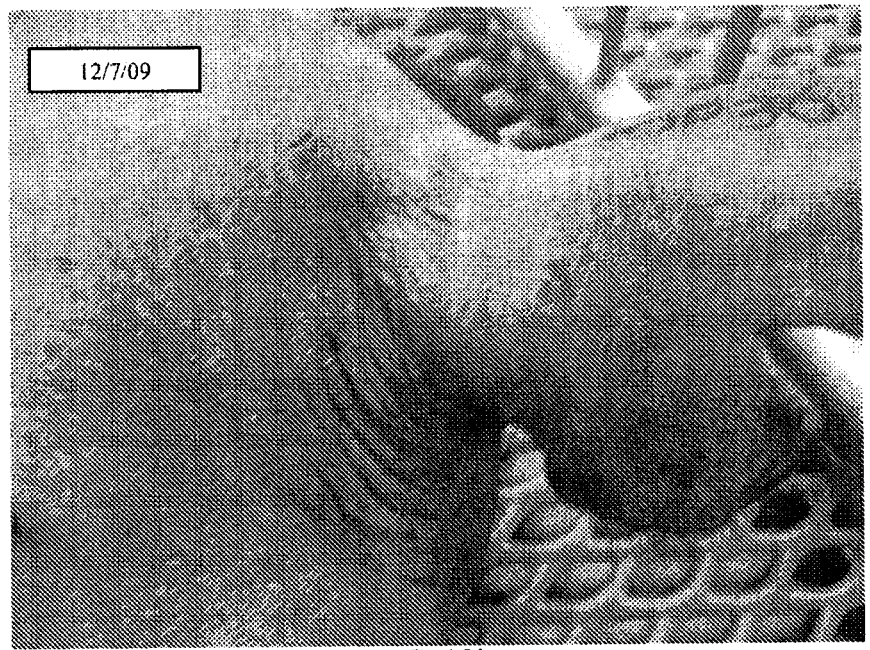
Figure 19M:
Figure 19N:
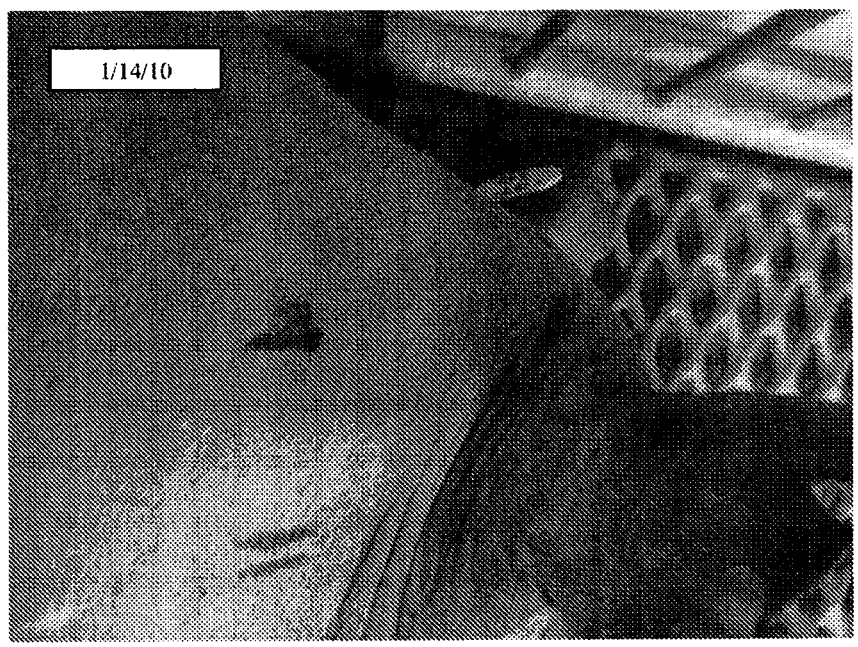
Figure 19O:
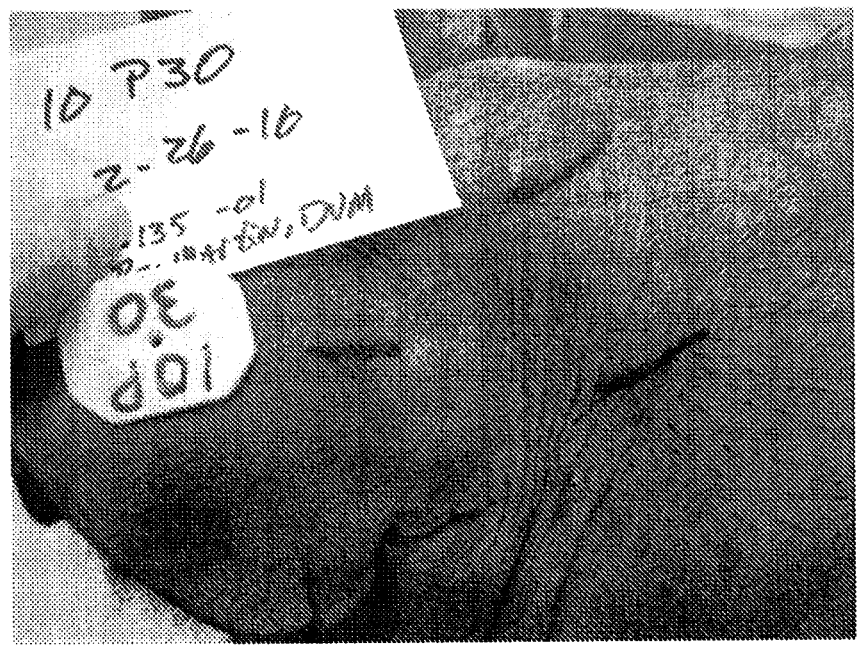

All implants were photographed at intervals throughout the study, and are illustrated in FIGS. 19a-o. These photographs document the rapid healing and benign reaction to all the implants.

9.7 Gross Necropsy Findings

All implants were completely healed. In general, the cervical base implants were neither seen nor felt. The ear implants were all seen and felt. In future studies ear implantation may be the preferred testing location. Dissection to the subdermal implant sites grossly showed almost no reaction to any of the implants. Visible capsules were not noted and capsule formation was very thin at the microscopic level. Generally the implants were almost invisible and fully integrated into the subdermal tissue. That is, they were not floating within a capsule but were adhered to the surrounding tissue and were difficult to dissect out. In general the implants were found as a change in resistance to the prosector's dissection knife.

9.8 Histology Findings

Histology sections were obtained by incising formalin fixed tissue blocks obtained during necropsy in a "bread loafing" serial manner. The implants were found by resistance to the incisions and a sample was submitted for H and E slide preparation. The slides are cross sections of the implants. Generally, a single anchor (half of the device) at each implantation site was sectioned for histology. All samples which were not cross sectioned for histology were dissected out en bloc and submitted to the sponsor for degradation analysis.

H and E histology slides were read by Roy Martin, DVM an attending veterinarian.

In general these implants were extremely biocompatible with a thin capsule and associated macrophages, multinucleate giant cells and fibroblasts typical of a benign foreign body reaction. Several sections did not have readable histology or implants seen. Two sections showed an additional focal lymphocytic response which is associated with inflammation and lesser biocompatibility.

Figure 20A:
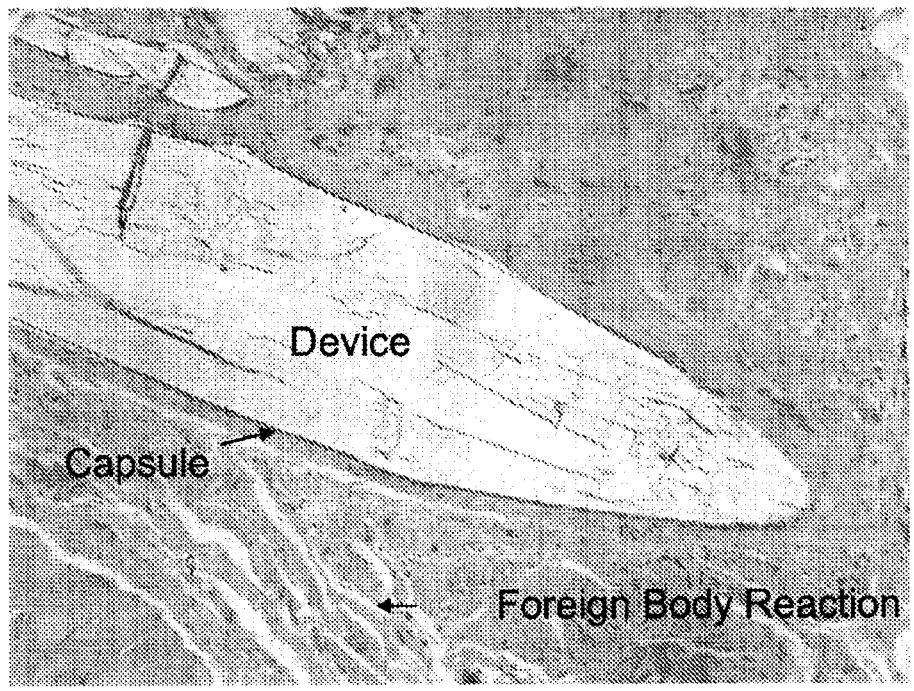
FIGS. 20a-d illustrate histological images according to the experiments of Example 1.

An example of the significant biocompatibility of the Juvence device is seen in the photomicrograph of 10P28 right ear base implant, in FIG. 20a. It shows the thin capsule, biointegration and benign foreign body response that would be hoped for.

Figure 20B:
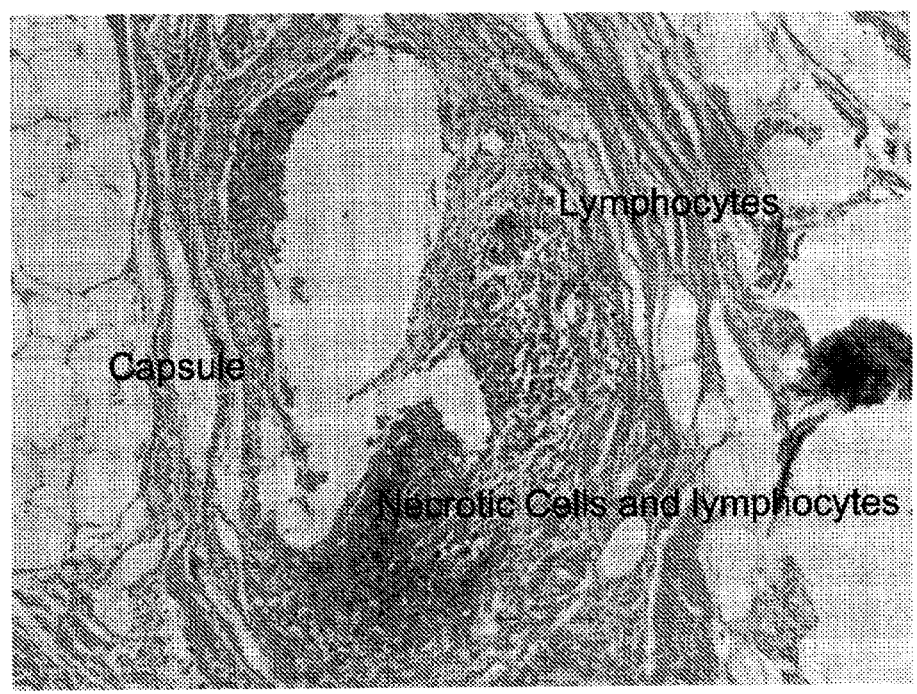

A section of polypropylene implant showed some inflammation with a lymphocytic response to the implantation, and is illustrated in FIG. 20b. Such a response is generally less desirable even though in this instance it appears very mild.

Figure 20C:
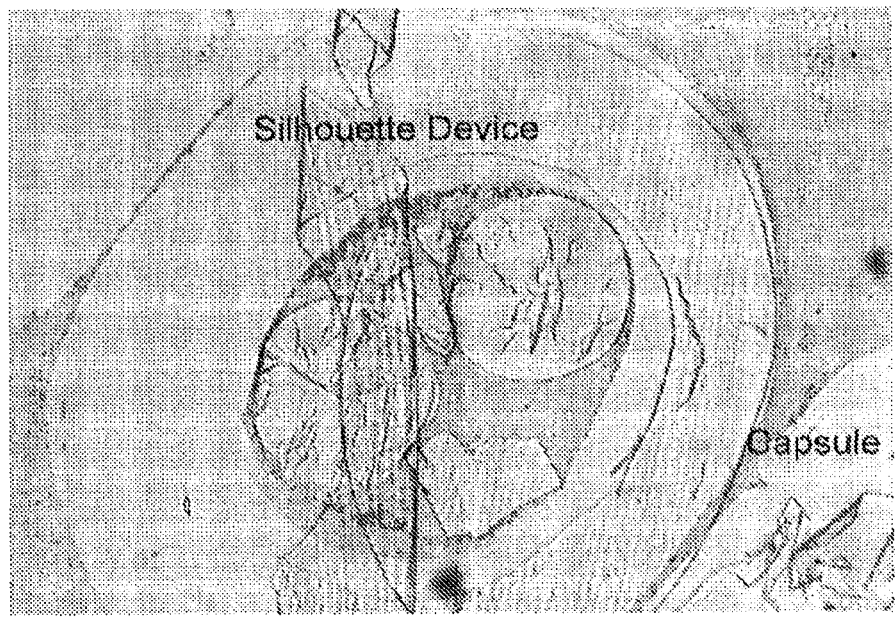
Figure 20D:
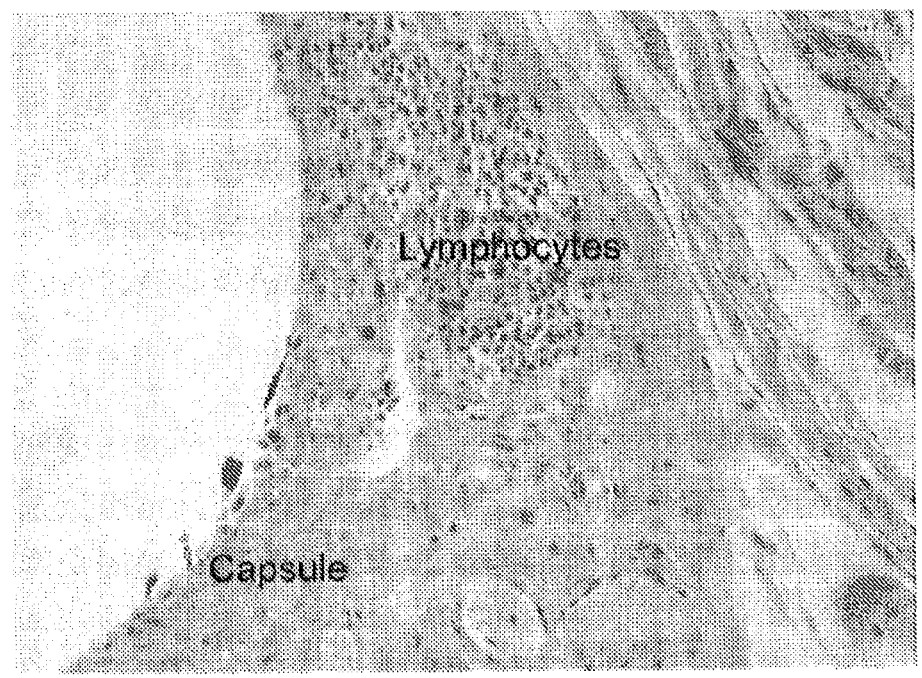
Figure 21A:
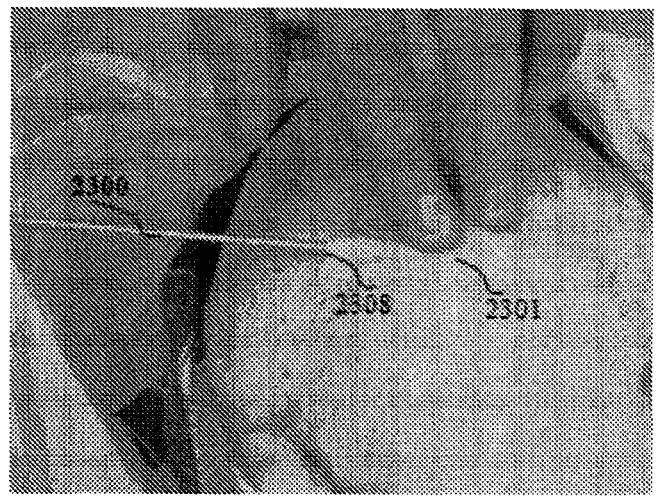
FIGS. 21a-c illustrate trials which were undertaken by using the device of the present invention in a chicken breast.
Figure 21B:
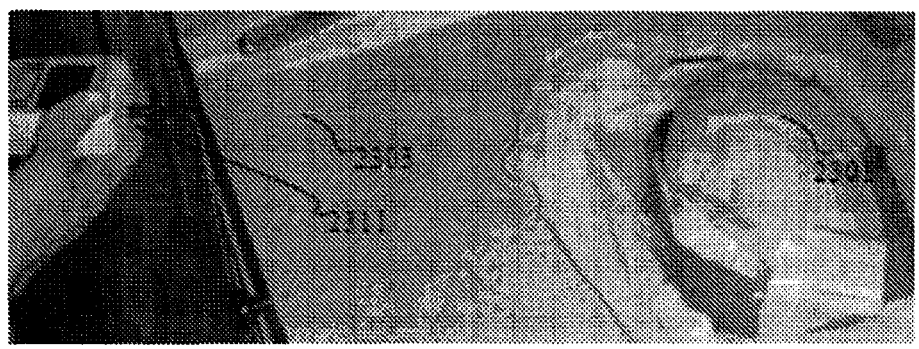
Figure 21C:
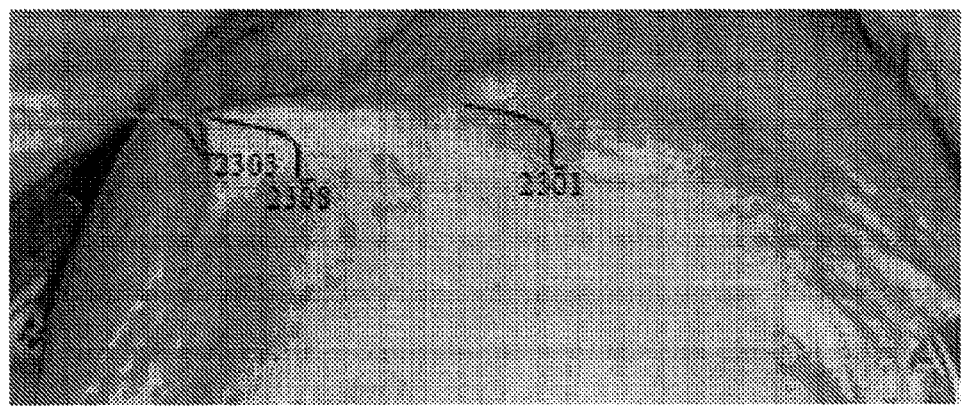
Figure 22:
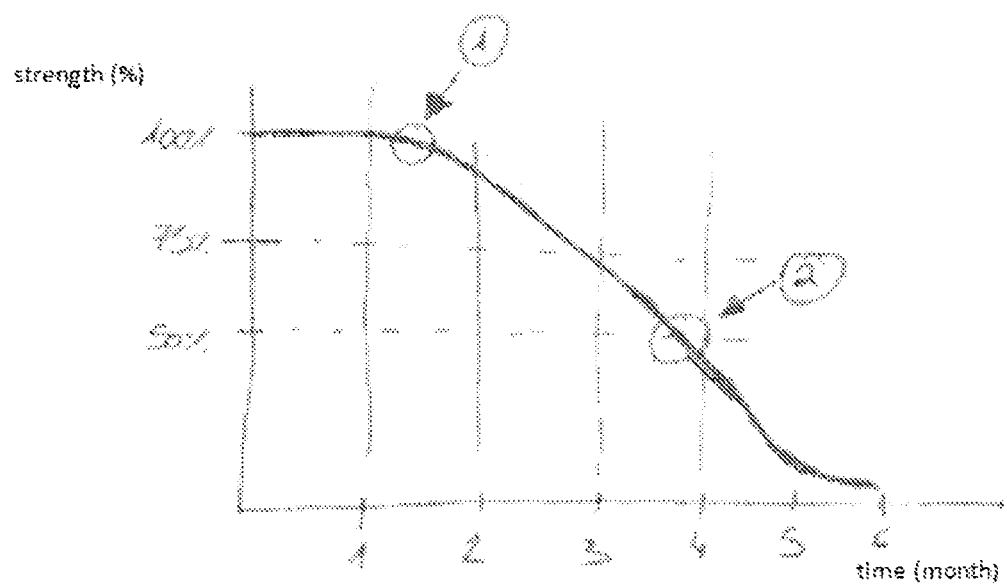
FIG. 22 illustrates Stress Vs. time results graph.
Figure 23:
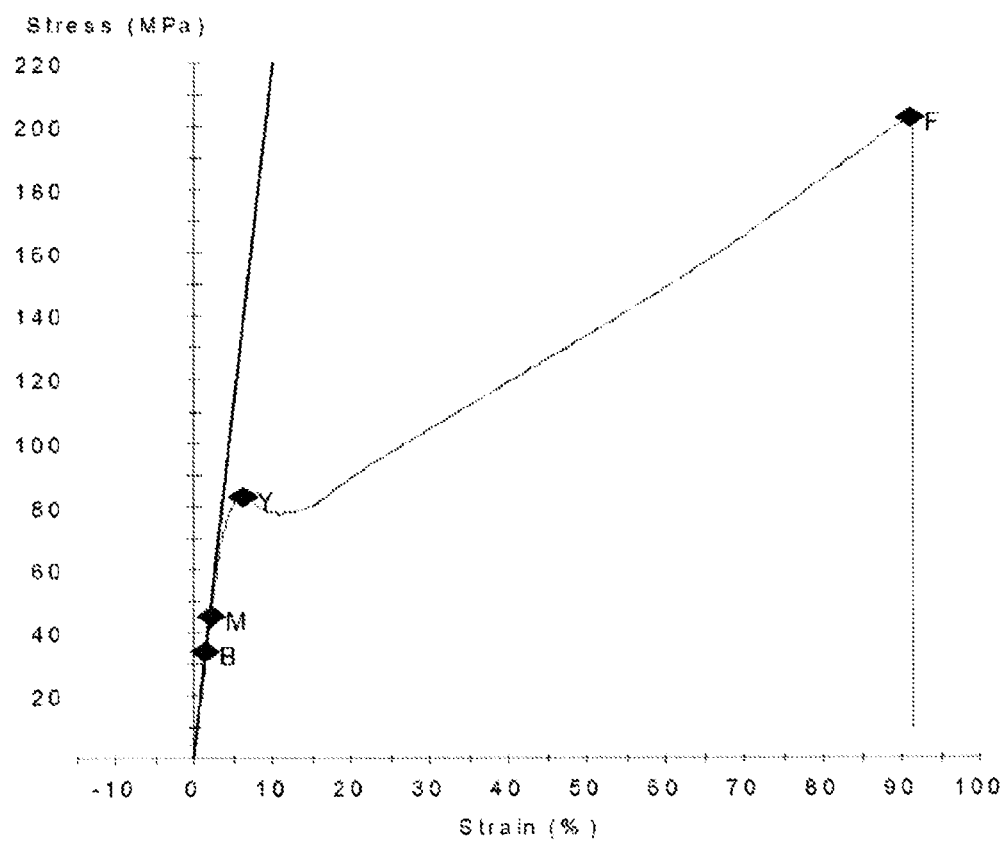
FIG. 23 illustrates Stress Vs. Strain results graph.

FIGS. 20c-d illustrate sections from the Silhouette implanted devices. They show a capsule formation, normal multinucleate giant cell foreign body reaction and a focal area of lymphoid cells showing a mild response.

The following table summarizes the histology responses seen:

TABLE 4

Histologic Response

| Response | Implant | Site | Animal |
|---|---|---|---|
| Thin capsule with multinucleate giant cells of a foreign body reaction. A focal area of lymphocytic response of mild irritation | Juvence | Right ear | 10P28 |
| Thin capsule with multinucleate giant cells of a foreign body reaction. Very biocompatible | Juvence | Right Base | 10P28 |
| Thin capsule with multinucleate giant cells of a foreign body reaction. Very biocompatible | Silhouette | Left ear | 10P28 |
| Thin capsule with multinucleate giant cells of a foreign body reaction. Very biocompatible | Juvence | Left Base | 10P28 |
| A thin focal area of capsule is seen. Response indeterminate | Juvence | Right ear base | 10P29 |
| Thin capsule with multinucleate giant cells of a foreign body reaction. Very biocompatible | Polypropylene | Right ear | 10P29 |
| Thin capsule with multinucleate giant cells of a foreign body reaction. Very biocompatible | Juvence | Left ear | 10P29 |
| Sample inadequate to read | Juvence | Left Base | 10P29 |
| Thin capsule with multinucleate giant cells of a foreign body reaction. Very biocompatible | Juvence | Right ear | 10P30 |
| Thin capsule with multinucleate giant cells of a foreign body reaction. A focal area of lymphocytic response of mild irritation | Polypropylene | Right Base | 10P30 |
| Thin capsule with multinucleate giant cells of a foreign body reaction. Very biocompatible | Juvence | Left ear | 10P30 |

TABLE 4-continued

| Histologic Response | | | |
|---|---|---|---|
| Response | Implant | Site | Animal |
| Thin capsule with multinucleate giant cells of a foreign body reaction. Very biocompatible | Silhouette | Left Base | 10P30 |

9.9 Degradation Analysis

The remaining en bloc sections of formalin fixated skin, subcutaneous tissue and implanted devices were carefully dissected in an attempt to retrieve implanted device sections. In general these were extremely difficult as the implants were very biocompatible and visible capsules or tissue reactions were not seen. The fibers were often white or clear and so were completely camouflaged to the prosector.

In general the base portions of the devices were found and any filaments traced from there. Often, the device had been damaged and disassembled, likely caused by the in vivo degradation, in growth of tissue or weight damage from the pig subjects. In no case was an entire Juvence device found. In several cases no implant material was retrieved. All implant sections harvested were placed in a formalin solution and shipped to Medical Murray for further degradation analysis. Upon receipt, Medical Murray removed the samples from solution and allowed them to dry for 24 hours before weighing.

A summary of the sections retrieved and their weights is listed in the table below. The recorded weights display an increase is the weight of the retrieved sections relative to the non-implanted device. This is an indication of tissue fusing with the retrieved device space as this would otherwise not occur with absorbable materials. With the difficult task of separating tissue from the devices and without retrieval of a complete absorbable anchor, the degradation analysis is inconclusive.

TABLE 2

| Device Explants | | | | |
|---|---|---|---|---|
| Weight of Sections (grams) | Sections Retrieved | Implant | Site | Animal |
| 0.042 | 1 base, portion of wing, 1 joint | Juvence | Right ear | 10P28 |
| 0.038 | 1 base, 1 head, 1 tube, portion of wing | Juvence | Right Base | 10P28 |
| N/A | None | Silhouette | Left ear | 10P28 |
| N/A | None | Juvence | Left Base | 10P28 |
| 0.069 | 1 base, 1 tube, 2 wings, 2 joints, 1 head (1 complete device) | Polypropylene | Right ear base | 10P29 |
| 0.040 | 1 base, 1 head, 1 tube | Juvence | Right ear | 10P29 |
| 0.013 | 1 base, 1 tube | Juvence | Left ear | 10P29 |
| 0.022 | 1 base, 1 tube | Juvence | Left Base | 10P29 |
| 0.056 | 1 base, 1 tube, portion of wing | Juvence | Right ear | 10P30 |
| 0.043 | 1 tube, 1 base, 1 head, 1 wing | Polypropylene | Right Base | 10P30 |
| 0.033 | 1 base, 1 tube, portion of wing | Juvence | Left ear | 10P30 |
| N/A | None | Silhouette | Left Base | 10P30 |

TABLE 2-continued

| Device Explants | | | | |
|---|---|---|---|---|
| Weight of Sections (grams) | Sections Retrieved | Implant | Site | Animal |
| 0.032 | 1 base, 1 tube, 2 wings, 2 joints, 1 head (1 complete anchor) | Juvence | Not Implanted | Control Device |

10 Discussion

This study was performed to describe the implantability, performance, safety and degradation of the Juvence and control subdermal implant devices in the porcine model. In general, these implanted devices performed well.

All of the devices implanted quite easily and totally healed within a couple of weeks. By the last twelve week follow-ups, all the skin incisions were completely healed and the devices integrated into the subdermal tissue with little tissue reaction and no gross capsules seen visibly.

Measurements of the distance between the implant ends were basically inconclusive. Following implantation, stretching was mostly detected. The observed and recorded data appears generally stable throughout the follow-up period with only two exceptions. The Juvence device implanted in the right ear of animal 10P28 appeared to lengthen slightly as did the polypropylene device implanted in the right ear of 10P29.

This investigation supports the safety of the implanted Juvence devices. All of these implants healed very quickly with no evidence of irritation or inflammation seen either upon the skin of living animals or in the subdermal tissues during necropsy. In fact, the implanted devices were very difficult to find and explant during necropsy because little if any capsule or tissue response formed around the implants and the tissue generally fused into the device space. The filaments of the implants were not able to be pulled out as they adhered and seemed to be biointegrated within the surrounding tissue. These implants were grossly invisible and only found through a change in friction by palpation or with the necropsy knife. Histology supported the safe biocompatibility of these implants with the formation of thin microscopic fibrous capsules maintained by fibroblasts and a typical multinucleate giant cell foreign body reaction. One polypropylene implant demonstrated a mild lymphocytic response to implantation suggesting mild irritation.

Degradation analysis by weight was inconclusive. The weight of the sections retrieved displayed an increase relative to the non-implanted control Juvence device. This is an indication that tissue or fluid had incorporated itself with the devices.

This study demonstrated the efficacy of the implantation procedure, generally showing stretching following implantation. Furthermore, this stretching was maintained throughout the study, although could not be corroborated by analytical data.

Lessons learned from this animal model for future studies suggest that weekly ear markings with a marker are preferable to tattooing. In addition, ear implants above the auricular musculature associated with ear movements may be the preferred implant site. In this model, a domestic Yorkshire cross may be a cost effective alternative to the Sinclair mini pig.

11 Conclusion

Within the limitations of this animal study, the Juvence device performed at least as good as the control devices in implantation ease and skin retraction distance measurements.

| Requirement | Feature |
|---|---|
| Bioabsorbable polymer to maintain at least 50% of starting flexural strength for 6 months after implanting. Complete mass loss in 12 months. No colorant or filler, transparent preferred. | Multi point anchors and clamp |
| Bioabsorbable polymer to maintain at least 50% of starting flexural strength for 6 months after implanting. Complete mass loss in 12 months. No colorant or filler, transparent preferred. Requires elasticity of 10% of its length at nominal load during installation. | Tensioning suture |
| 304 stainless steel, passivated | Introducer tube Packaging |

The values $N_1$-$N_6$ have been varied to optimize the performance of the device.

| Tolerance | Requirement | Feature |
|---|---|---|
| Minimum | Embed in skin tissue of a pig belly such that the skin between two anchors can be compressed 20%. Load without pulling free $N_1$ grams. Must hold load without moving more than $N_2$ mm for $N_3$ hours. Must be able to be sterilized and still meet strength requirements. | Multipoint anchor |
| Minimum | Must have ultimate breaking strength of $N_4$. Modulus of elasticity to be $N_5$ | Tensioning suture |
| Maximum | Stiffness and tip to allow insertion between the skin layers at a maximum load $N_6$ | Introducer |
| Maximum | Installation of both anchors, tensioning, clamping suture and cutting suture must be accomplished in 10 minutes | Procedure |
| | Must pass packaging distribution testing per ISO 11607 | Packaging |

All these devices appeared quite safe with rapid healing, lack of gross lesions and very benign histologic responses.

Example 2

Testing and Standards

ANSI testing procedure "ANSI/AAMI/ISO 10993-1: 1997 Biological Evaluation of Medical Devices—Part 1: Evaluation and Testing" was followed to evaluate one embodiment of the device, which had the dimensions shown in the following table.

The materials of the device were as according to the following table.

| Notes | Overall Length (mm) | ID (Inches) (Extrusion) | OD (mm) | Description |
|---|---|---|---|---|
| Size based on meeting holding load functional requirements | 9 | | 1.9 max | Multipoint Anchors |
| Must reach from distal anchor to handle position | | | | Tensioning suture |
| | | 2.0 max. | 2.3 max. | conducting tool |

A list of test design requirements was drawn up as detailed in the following table.

A required curve of strength loss vs. time was determined based on the desired degradation of the elements of the device during and after the body has formed permanent structures (i.e., fibrotic tissue and/or internal scar) around them (see FIG. 23a).

FIG. 23a illustrates the variation of the strength vs. time. Point 1 represents the time in which the device starts to lose its strength. The device can lose from its strength but it has to have enough strength to maintain the desired esthetic outcome. In other words, the mechanical strength of the device plus the biological strength must equal the desired esthetic outcome strength. The tolerance should be in the range of 0/−14 days.

Point 2 represents the time in which the device loses 50% of its strength. The tolerance should be in the range of 0/+60 days.

In one embodiment of the device, the material osteoprene was selected to provide this curve of strength loss versus time. Mixtures were determined for use in injection molding to form the anchor parts. These create a crystalline structure after molding to give significant increases in tensile strength and slower reduction of strength over time. For example a 40% strength retention after 4 months for this material can be achieved.

For the suture material, SMC 7 (Glycoprene II) can for example be used, which would have a similar strength retention versus time. The stress strain curve for this material is shown in FIG. 23b, which includes a comparison of stress vs. strain data between injection molded and monafilment SMC 7.

Other materials that can be used as the suture material can be for example Co-Polylactide Yarn, Co-Polylactide Braid I, Lactide copolymer, Lactocarbonate Braid, Lactocarbonate polymer, Trimethylenecarbonate or any combination thereof.

If one uses a small enough filament and load it above the yield strength one can see it has considerable elasticity. (Section Y-F on the stress-strain curve of FIG. 23b). Of course to work in this range for the material, one would need to know the expected nominal load as placed in the tissue and expected maximum load to avoid failure.

I claim:

1. A minimally invasive multipoint fixation device adapted to laparoscopically reposition body tissues, said device comprising:
    a. at least one distal anchor connectable to a first tissue location;
    b. at least one proximal anchor connectable to a second tissue location;
    c. an elongated connecting element, having a main longitudinal axis, adapted to interconnect between said at least one distal anchor and said at least one proximal anchor; and,
    d. deployment means connected to said at least one distal anchor or said at least one proximal anchor or both;
    said distal and proximal anchors are characterized by at least two configurations: (i) a folded configuration, in which said distal and proximal anchors are substantially parallel to said main longitudinal axis; and, (ii) a deployed configuration, in which said distal anchor is positioned at an angle A with respect to said main longitudinal axis, and said proximal anchor is positioned at an angle B with respect to said main longitudinal axis;
    wherein application of a mechanical force by means of said deployment means is adapted to reversibly reconfigure at least one of said distal anchor, said proximal anchor and any combination thereof from said folded configuration to said deployed configuration;
    further wherein said distal and said proximal anchors comprise at least one attachment element selected from a group consisting of: barbs, cogs, spikes, and any combination thereof; said attachment elements are adapted to reversibly connect said distal and said proximal anchors to said first and second tissue locations.

2. The fixation device of claim 1, wherein said fixation device further comprises tension varying means connectable to said distal and proximal anchors, adapted to alter parameters selected from a group consisting of: the length of said elongated connecting element; and, the tension applied on said elongated connecting element, such that said first and said second tissue locations are repositioned with respect to each other according to said parameters.

3. The fixation device of claim 2, wherein said tension varying means is further adapted to alter said parameters by a locking means adapted to affix said proximal anchor to said elongated connecting element.

4. The fixation device of claim 1, wherein said deployment means is at least two hinged wings; each of said hinged wings being characterized by at least two configurations: (i) a folded configuration, in which said wings are substantially parallel to said main longitudinal axis, such that said anchor is folded and, (ii) a deployed configuration, in which said wings are positioned at angles selected from a group consisting of said angles A or B, such that said anchor is deployed.

5. The fixation device of claim 4, wherein at least one deployment tool is reversibly coupled to at least one of said wings, such that application of a mechanical force by said at least one deployment tool to said wings is adapted to reversibly reconfigure at least one of said wings from said folded configuration to said deployed configuration.

6. The fixation device of claim 5, wherein at least one of the following is being held true (a) said deployment tool is adapted to be coupled to at least one of said wings, when said wings are in said deployed configuration, so as to increase the mechanical strength of the same; (b) said at least one deployment tool is selected from a group consisting of: a rod, a stick, a shaft, a needle, a pin, a wire, a thread, a suture, a string, a cord, a fiber, a rope, and any combination thereof.

7. The fixation device of claim 1, wherein at least one of the following is being held true (a) said distal and said proximal anchors comprise at least one groove adapted to incorporate said deployment means; (b) said mechanical force is selected from a group consisting of: pushing forces, pulling forces, shearing forces, bending forces, torque, and any combination thereof.

8. The fixation device of claim 1, wherein said elongated connecting element is selected from a group consisting of: a rigid element or a non-rigid element; further wherein said elongated connecting element is selected from a group consisting of: a thread, a suture, a string, a cord, a fiber, a rope, a wire, a rod, a stick, a shaft, and any combination thereof.

9. The fixation device of claim 1, wherein each of said distal and said proximal anchors are reversibly convertible from said folded configuration to said deployed configuration by rotation of the same relative to said longitudinal axis.

10. The fixation device of claim 1, wherein said fixation device further comprises a conducting tool adapted to keep said distal and proximal anchors in said folded configuration, and to facilitate the conduction of said distal and proximal anchors to said first and second tissue locations.

11. The fixation device of claim 10, wherein at least one of a group consisting of: at least one said distal anchor, at least one said proximal anchor, said elongated connecting element, and said conducting tool comprise bioactive coatings selected from a group consisting of: proteins, growth factors, antigens, carbon-like diamond, carbon, hyaluronic acid, collagen, silver, gold, and any combination thereof.

12. The fixation device of claim 1, wherein said angles A and B are in a range of about 0.1 degrees and about 180 degrees.

13. The fixation device of claim 12, wherein said angles A and B are about 90 degrees.

14. The fixation device of claim 1, wherein at least one of the following is being held true (a) said elongated connecting element is adapted to deploy at least one of said distal anchor or said proximal anchor; (b) said first and second tissue locations are located between the dermis and the muscle; and any combination thereof.

15. The fixation device of claim 1, wherein said distal and proximal anchors are comprised of materials selected from the group consisting of: polyethylene, polypropylene, polyurethanes, poly(methyl methacrylate), polycarbonates, silicone rubber, biodegradable polymers, synthetic and natural occurring materials including polyalkylene esters, polylactic acid and its co-polymers, polyvinyl esters, polyvinyl alcohol, polyanhydrides, and polycarbonates, Polydioxanone (PDO), Polycaprolactone (PCL), Polylactic acid (PLA), Polyglycolic acid (PGA), Adipic acid, PEG, glutamic acid, polymers, metals, metal alloys, ceramics, shape memory alloys, hydroxyapatite, and glass.

16. The fixation device of claim 1, wherein at least one of the following is being held true (a) said elongated connecting element is made of an elastic material; (b) said fixation device is adapted to create a network of anchors; and any combination thereof.

17. A minimally invasive multipoint fixation method for laparoscopically repositioning body tissues, said method comprising steps of:
   a. providing a minimally invasive multipoint fixation device adapted to laparoscopically locally reposition body tissues, said device comprising: (i) at least one distal anchor connectable to a first tissue location; (ii) at least one proximal anchor connectable to a second tissue location; (iii) an elongated connecting element, having a main longitudinal axis, adapted to interconnect between said distal anchor and said proximal anchor; and (iv) deployment means connected to said distal anchor or said proximal anchor or both;
   b. connecting said distal anchor to said proximal anchor via said elongated connecting element;
   c. anchoring said distal anchor at said first tissue location;
   d. anchoring said proximal anchor at said second tissue location;
   said step (a) is performed by providing a fixation device with distal and proximal anchors which are characterized by at least two configurations: (i) a folded configuration, in which said distal and proximal anchors are substantially parallel to said main longitudinal axis; and, (ii) a deployed configuration, in which said distal anchor is positioned at an angle A with respect to said main longitudinal axis, and said proximal anchor is positioned at an angle B with respect to said main longitudinal axis;
   wherein said steps (c)-(d) comprise additional steps of applying a mechanical force by means of said deployment means thereby reversibly reconfiguring at least one of said distal or proximal anchors from said folded configuration to said deployed configuration;
   further wherein said distal and said proximal anchors comprise at least one attachment element selected from a group consisting of: barbs, cogs, spikes, and any combination thereof; said attachment elements are adapted to reversibly connect said distal and said proximal anchors to said first and second tissue locations.

18. The method of claim 17, further comprising steps of: (e) providing said fixation device with tension varying means connectable to said distal and proximal anchors; (f) altering parameters selected from a group consisting of: the length of said elongated connecting element; and, the tension applied on said elongated connecting element; (g) repositioning said first and said second tissue locations with respect to each other according to said parameters; (h) securing said proximal anchor to said elongated connecting element.

19. The method of claim 18, further comprising at least one step selected from (a) repeating said steps (a)-(f) for creating a network of anchors interconnected between each other by a plurality of elongated connecting elements, and thereby setting the tension of said elongated connecting elements independently; (b) providing said elongated connecting element comprising an elastic material; and, (c) sensing said tension of said elongated connecting element via a sensing means.

20. The method of claim 18, wherein at least one of the following is held true: (a) said step (f) of altering said parameters is performed by affixing said proximal anchor to said elongated connecting element via a locking means; and, (b) said steps (c) and (e) are performed such that said first and second tissue locations are located between the dermis and the muscle.

21. The method of claim 17, further comprising steps of: (e) providing said deployment means in the form of at least two hinged wings; each of said hinged wings being characterized by at least two configurations: (i) a folded configuration, in which said wings are substantially parallel to said main longitudinal axis, such that said anchor is folded and, (ii) a deployed configuration, in which said wings are positioned at angles selected from a group consisting of said angles A or B, such that said anchor is deployed.

22. The method of claim 17, further comprising at least one step selected from (a) deploying said distal and proximal anchors by deploying said wings; (b) coupling at least one deployment tool to at least one of said wings; and, applying a mechanical force by said at least one deployment tool to said wings, and thereby reversibly reconfiguring said at least one of said wings from said folded configuration into said deployed configuration; (c) coupling said deployment tool to at least one of said wings, when said wings are in said deployed configuration, and thereby increasing the mechanical strength of said wings; (d) incorporating said deployment means in at least one groove located within at least one of said distal and said proximal anchors; and any combination thereof.

23. The method of claim 22, further comprising at least one step selected from: (a) removing at least part of said deployment mechanism from said fixation device; and, leaving said distal and proximal anchors in said deployed configuration with a predetermined tension in said elongated connecting element therebetween; (b) cutting at least one unused part of said elongated connecting element; and, (c) implanting said distal and proximal anchors at said first and second tissue locations; and any combination thereof.

24. The method of claim 17, further comprising at least one of the following steps (a) selecting said elongated connecting element from a group consisting of: a rigid element or a non-rigid element; (b) selecting said elongated connecting element from a group consisting of: a thread, a suture, a string, a cord, a fiber, a rope, a wire, a rod, a stick, a shaft, and any combination thereof.

25. The method of claim 17, further comprising at least one step selected from (a) providing said fixation device with a conducting tool for keeping said distal and proximal anchors in said folded configuration; and, facilitating the insertion of said distal and proximal anchors to said first and second tissue locations via said conducting tool while performing said steps (c)-(d); (b) inserting said distal and proximal anchors to said conducting tool before said steps (c)-(d); (c) deploying at least one of said distal anchor or said proximal anchor via said elongated connecting element.

26. The method of claim 25, further comprising the step of coating at least one of a group consisting of: said distal and proximal anchors, said elongated connecting element, and said conducting tool with a material selected from a group consisting of: proteins, growth factors, antigens, carbon-like diamond, carbon, hyaluronic acid, collagen, silver, gold, and any combination thereof.

27. The method of claim 17, wherein at least one of the following is being held true (a) said angles A and B are in a range of about 0.1 degrees and about 180 degrees; (b) said steps (c) and (d) are performed by reversibly rotating said distal and proximal anchors relative to said longitudinal axis; and any combination thereof.

28. The method of claim 17, further comprising the step of selecting the materials of said distal and proximal anchors from the group consisting of: polyethylene, polypropylene, polyurethanes, poly(methyl methacrylate), polycarbonates, silicone rubber, biodegradable polymers, synthetic and natural occurring materials including polyalkylene esters, polylactic acid and its co-polymers, polyvinyl esters, polyvinyl alcohol, polyanhydrides, and polycarbonates, Polydioxanone (PDO), Polycaprolactone (PCL), Polylactic acid (PLA), Polyglycolic acid (PGA), Adipic acid, PEG, glutamic acid, polymers, metals, metal alloys, ceramics, shape memory alloys, hydroxyapatite, and glass.

* * * * *